US008383820B2

(12) United States Patent
Ebdrup

(10) Patent No.: US 8,383,820 B2
(45) Date of Patent: Feb. 26, 2013

(54) N-ADAMANTYL BENZAMIDES AS INHIBITORS OF 11-β-HYDROXYSTEROID DEHYDROGENASE

(75) Inventor: Soren Ebdrup, Roskilde (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 276 days.

(21) Appl. No.: 12/528,229

(22) PCT Filed: Feb. 19, 2008

(86) PCT No.: PCT/EP2008/051971
§ 371 (c)(1),
(2), (4) Date: Nov. 1, 2010

(87) PCT Pub. No.: WO2008/101914
PCT Pub. Date: Aug. 28, 2008

(65) Prior Publication Data
US 2011/0039853 A1 Feb. 17, 2011

(30) Foreign Application Priority Data
Feb. 23, 2007 (EP) .................... 07102956

(51) Int. Cl.
A61K 31/44 (2006.01)
A61K 31/445 (2006.01)
A61K 31/40 (2006.01)
C07D 211/68 (2006.01)
C07D 207/00 (2006.01)

(52) U.S. Cl. ........ 546/194; 546/285; 548/528; 514/325; 514/345; 514/424

(58) Field of Classification Search .................. None
See application file for complete search history.

(56) References Cited

U.S. PATENT DOCUMENTS

| 2,913,454 A | 11/1959 | Petersen et al. |
| 3,723,442 A | 3/1973 | Nakanishi et al. |
| 3,784,551 A | 1/1974 | Nakanishi et al. |
| 4,350,696 A | 9/1982 | Cross et al. |
| 4,482,555 A | 11/1984 | Doria et al. |
| 4,851,423 A | 7/1989 | Girijavallabhan et al. |
| 4,963,590 A | 10/1990 | Backstrom et al. |
| 5,001,133 A | 3/1991 | Richardson et al. |
| 5,049,695 A | 9/1991 | Abraham et al. |
| 5,112,861 A | 5/1992 | Backstrom et al. |
| 5,122,539 A | 6/1992 | Abraham et al. |
| 5,169,850 A | 12/1992 | Dusza et al. |
| 5,225,402 A | 7/1993 | Ogawa et al. |
| 5,258,407 A | 11/1993 | Washburn et al. |
| 5,260,325 A | 11/1993 | Markwalder et al. |
| 5,272,167 A | 12/1993 | Girijavallabhan et al. |
| 5,274,104 A | 12/1993 | Arnaud et al. |
| 5,290,803 A | 3/1994 | Abraham et al. |
| 5,314,880 A | 5/1994 | Whittaker et al. |
| 5,356,904 A | 10/1994 | Freidinger et al. |
| 5,382,680 A | 1/1995 | Abraham et al. |
| 5,426,105 A | 6/1995 | Manning et al. |
| 5,432,191 A | 7/1995 | Abraham et al. |
| 5,436,254 A | 7/1995 | Ogawa et al. |
| 5,446,194 A | 8/1995 | Backstrom et al. |
| 5,459,144 A | 10/1995 | Girijavallabhan et al. |
| 5,585,394 A | 12/1996 | Di Malta et al. |
| 5,591,892 A | 1/1997 | Abraham et al. |
| 5,596,020 A | 1/1997 | Morris et al. |
| 5,602,137 A | 2/1997 | Ruhter et al. |
| 5,648,375 A | 7/1997 | Abraham et al. |
| 5,650,513 A | 7/1997 | Langhals et al. |
| 5,652,247 A | 7/1997 | Ogawa et al. |
| 5,674,879 A | 10/1997 | Manning et al. |
| 5,677,330 A | 10/1997 | Abraham et al. |
| 5,705,521 A | 1/1998 | Abraham et al. |
| 5,731,454 A | 3/1998 | Abraham et al. |
| 5,750,532 A | 5/1998 | Girijavallabhan et al. |
| 5,786,379 A | 7/1998 | Bernardon |
| 5,795,907 A | 8/1998 | Kalindjian et al. |
| 5,872,282 A | 2/1999 | Abraham et al. |
| 5,912,260 A | 6/1999 | Kalindjian et al. |
| 5,919,829 A | 7/1999 | Kalindjian et al. |
| 5,927,283 A | 7/1999 | Abraham et al. |
| 5,932,569 A | 8/1999 | Janssens et al. |
| 5,939,437 A | 8/1999 | Kalindjian et al. |
| 6,001,879 A | 12/1999 | Seitz et al. |
| 6,096,736 A | 8/2000 | Ogawa et al. |
| 6,124,289 A | 9/2000 | He et al. |

(Continued)

FOREIGN PATENT DOCUMENTS

| CN | 1736485 | 2/2006 |
| DE | 4338784 | 5/1995 |

(Continued)

OTHER PUBLICATIONS

Andrew et al., J. Clin. Endocrinol. Metab. vol. 87, pp. 277-285 (2002).
Andrews et al., J. Clin. Endocrinol. Metab. vol. 88, pp. 285-291 (2003).
Barf T et al: "Recent progress in 11-[beta]-hydroxysteroid dehydrogenase type 1 (11-[beta]-HSD1) inhibitor development" Drugs of the Future 2006 Spain, vol. 31, No. 3, Mar. 2006, pp. 231-243.
Bird et al., J. Physiology vol. 585, pp. 187-201 (2007).
Brem et al., Hypertension vol. 31, pp. 459-462 (1998).
Brindley et al., Progress Lipid Res. vol. 30, pp. 349-360 (1991).
Bujalska et al., Endocrinology vol. 140, pp. 3188-3196 (1999).
Carruthers et al., J. Chem. Soc. Perkin Trans. 1 vol. 10, pp. 2854-2856 (1990).

(Continued)

Primary Examiner — Janet Andres
Assistant Examiner — Heidi Reese
(74) Attorney, Agent, or Firm — Samuel B. Rollins

(57) ABSTRACT

Novel substituted benzamide based inhibitors, their use in therapy, pharmaceutical compositions comprising the compounds, the use of said compounds in the manufacture of medicaments, and therapeutic methods comprising the administration of said compounds are described. The present compounds modulate the activity of 11β-hydroxysteroid dehydrogenase type 1 (11βHSD1) and are accordingly useful in the treatment of diseases in which such a modulation is beneficial, such as the metabolic syndrome.

46 Claims, No Drawings

U.S. PATENT DOCUMENTS

| | | |
|---|---|---|
| 6,458,803 B1 | 10/2002 | Sikorski et al. |
| 6,506,783 B1 | 1/2003 | Camden |
| 6,521,641 B1 | 2/2003 | Klein et al. |
| 6,548,549 B1 | 4/2003 | Seitz et al. |
| 6,613,803 B1 | 9/2003 | Wang et al. |
| 6,638,947 B2 | 10/2003 | Wang et al. |
| 6,696,442 B2 | 2/2004 | Wang et al. |
| 6,833,371 B2 | 12/2004 | Atkinson et al. |
| 7,129,242 B2 | 10/2006 | Satoh et al. |
| 7,157,490 B2 | 1/2007 | Colandrea et al. |
| 7,186,735 B2 | 3/2007 | Strobel et al. |
| 7,265,122 B2 | 9/2007 | Wu et al. |
| 7,358,238 B2 | 4/2008 | Andersen et al. |
| 7,501,405 B2 | 3/2009 | Kampen et al. |
| 7,557,110 B2 | 7/2009 | Kataoka et al. |
| 7,700,583 B2 | 4/2010 | Gundertofte et al. |
| 7,723,323 B2 | 5/2010 | Andersen et al. |
| 2002/0006932 A1 | 1/2002 | Galley et al. |
| 2002/0115671 A1 | 8/2002 | Goehring |
| 2003/0144256 A1 | 7/2003 | Klein et al. |
| 2004/0142922 A1 | 7/2004 | Alanine et al. |
| 2004/0186102 A1 | 9/2004 | Wu et al. |
| 2005/0009871 A1 | 1/2005 | Ramesh et al. |
| 2005/0054850 A1 | 3/2005 | Wu et al. |
| 2005/0080087 A1 | 4/2005 | Pendri et al. |
| 2005/0154202 A1 | 7/2005 | Hagmann et al. |
| 2005/0261302 A1 | 11/2005 | Hoff et al. |
| 2006/0009918 A1 | 1/2006 | Mallik et al. |
| 2006/0079506 A1 | 4/2006 | Linders et al. |
| 2006/0094699 A1 | 5/2006 | Kampen et al. |
| 2006/0111366 A1 | 5/2006 | Andersen et al. |
| 2006/0149070 A1 | 7/2006 | Rohde et al. |
| 2006/0281773 A1 | 12/2006 | Patel et al. |
| 2007/0054882 A1 | 3/2007 | Klein et al. |
| 2007/0270408 A1 | 11/2007 | Andersen et al. |
| 2008/0108598 A1 | 5/2008 | Andersen et al. |
| 2009/0105289 A1 | 4/2009 | Kilburn et al. |
| 2009/0118259 A1 | 5/2009 | Kilburn et al. |
| 2009/0124598 A1 | 5/2009 | Andersen et al. |
| 2009/0137574 A1 | 5/2009 | Kampen et al. |
| 2009/0264412 A1 | 10/2009 | Kampen et al. |
| 2009/0264414 A1 | 10/2009 | Andersen et al. |
| 2009/0306048 A1 | 12/2009 | Kilburn et al. |
| 2009/0325932 A1 | 12/2009 | Ebdrup et al. |
| 2010/0056600 A1 | 3/2010 | Ebdrup et al. |
| 2010/0076041 A1 | 3/2010 | Kilburn et al. |
| 2010/0087543 A1 | 4/2010 | Ebdrup et al. |
| 2010/0120743 A1 | 5/2010 | Gundertofte et al. |
| 2010/0137377 A1 | 6/2010 | Petersen et al. |
| 2010/0168083 A1 | 7/2010 | Ebdrup |
| 2010/0197658 A1 | 8/2010 | Andersen et al. |
| 2010/0292215 A1 | 11/2010 | Ebdrup et al. |
| 2010/0331366 A1 | 12/2010 | Ebdrup |
| 2011/0003852 A1 | 1/2011 | Ebdrup |
| 2011/0003856 A1 | 1/2011 | Ebdrup |
| 2011/0224244 A1 | 9/2011 | Polisetti et al. |

FOREIGN PATENT DOCUMENTS

| | | |
|---|---|---|
| FR | 2456731 | 12/1980 |
| GB | 825514 | 11/1956 |
| JP | 08-048662 | 2/1996 |
| JP | 09-221476 | 8/1997 |
| JP | 11-152269 | 6/1999 |
| JP | 2001 139574 | 5/2001 |
| JP | 2003-286171 | 10/2003 |
| JP | 2007-231005 | 9/2007 |
| WO | WO 94/01113 | 1/1994 |
| WO | WO 94/18193 | 8/1994 |
| WO | WO 97/07789 | 3/1997 |
| WO | WO 97/22588 | 6/1997 |
| WO | WO 97/24328 | 7/1997 |
| WO | WO 98/46559 | 10/1998 |
| WO | WO 99/30699 | 6/1999 |
| WO | WO 99/61013 | 12/1999 |
| WO | WO 00/12074 | 3/2000 |
| WO | WO 00/46197 | 8/2000 |
| WO | WO 00/47558 | 8/2000 |
| WO | WO 00/63165 | 10/2000 |
| WO | WO 00/73283 | 12/2000 |
| WO | WO 01/02385 | 1/2001 |
| WO | WO 01/22969 | 4/2001 |
| WO | WO 01/32621 | 5/2001 |
| WO | WO 01/44213 | 6/2001 |
| WO | WO 01/64676 | 9/2001 |
| WO | WO 01/90090 | 11/2001 |
| WO | WO 01/90091 | 11/2001 |
| WO | WO 01/90092 | 11/2001 |
| WO | WO 01/90093 | 11/2001 |
| WO | WO 01/90094 | 11/2001 |
| WO | WO 01/00626 | 1/2002 |
| WO | WO 02/02797 | 1/2002 |
| WO | WO 02/10191 | 2/2002 |
| WO | WO 02/072084 | 9/2002 |
| WO | WO 02/076435 | 10/2002 |
| WO | WO 02/089781 | 11/2002 |
| WO | WO 02/094799 | 11/2002 |
| WO | WO 02/100819 | 12/2002 |
| WO | WO 03/000649 | 1/2003 |
| WO | WO 03/028641 | 4/2003 |
| WO | WO 03/028730 | 4/2003 |
| WO | WO 03/029245 | 5/2003 |
| WO | WO 03/037274 | 5/2003 |
| WO | WO 03/037900 | 5/2003 |
| WO | WO 03/065983 | 8/2003 |
| WO | WO 03/070732 | 8/2003 |
| WO | WO 03/086410 | 10/2003 |
| WO | WO 2004/024896 | 3/2004 |
| WO | WO 2004/024897 | 3/2004 |
| WO | WO 2004/033427 | 4/2004 |
| WO | WO 2004/052461 | 6/2004 |
| WO | WO 2004/056744 | 7/2004 |
| WO | WO 2004/056745 | 7/2004 |
| WO | WO 2006/044645 | 7/2004 |
| WO | WO 2004/065351 | 8/2004 |
| WO | WO 2004/075823 | 9/2004 |
| WO | WO 2004/087159 | 10/2004 |
| WO | WO 2004/089380 | 10/2004 |
| WO | WO 2004/089415 | 10/2004 |
| WO | WO 2004/089416 | 10/2004 |
| WO | WO 2004/089470 | 10/2004 |
| WO | WO 2004/089471 | 10/2004 |
| WO | WO 2004/089896 | 10/2004 |
| WO | WO 2004/091610 | 10/2004 |
| WO | WO 2005/013950 | 2/2005 |
| WO | WO 2005/028438 | 3/2005 |
| WO | WO 2005/032484 | 4/2005 |
| WO | WO 2005/035534 | 4/2005 |
| WO | WO 2005/085202 | 9/2005 |
| WO | WO 2005/095397 | 10/2005 |
| WO | WO 2005/115975 | 12/2005 |
| WO | WO 2006/009835 | 1/2006 |
| WO | WO 2006/014012 | 2/2006 |
| WO | WO 2006/028958 | 3/2006 |
| WO | WO 2006/040329 | 4/2006 |
| WO | WO 2006/048330 | 5/2006 |
| WO | WO 2006/055752 | 5/2006 |
| WO | WO 2006/094633 | 9/2006 |
| WO | WO 2006/105127 | 10/2006 |
| WO | WO 2006/113261 | 10/2006 |
| WO | WO 2006/136402 | 12/2006 |
| WO | WO 2007/046001 | 4/2007 |
| WO | WO 2007/066784 | 4/2007 |
| WO | WO 2007/051810 | 5/2007 |
| WO | WO 2007/051811 | 5/2007 |
| WO | WO 2007/058960 | 5/2007 |
| WO | WO 2007/059905 | 5/2007 |
| WO | WO 2007/107550 | 9/2007 |
| WO | WO 2007/109160 | 9/2007 |
| WO | WO 2007/115935 | 10/2007 |
| WO | WO 2007/144394 | 12/2007 |
| WO | WO 2008/002244 | 1/2008 |
| WO | WO 2008/006702 | 1/2008 |
| WO | WO 2008/006703 | 1/2008 |
| WO | WO 2008/101885 | 8/2008 |
| WO | WO 2008/101886 | 8/2008 |
| WO | WO 2008/101907 | 8/2008 |

| WO | WO 2008/110196 | 9/2008 |
| WO | WO 2008/119017 | 10/2008 |
| WO | WO 2008/127924 | 10/2008 |
| WO | WO 2008/134221 | 11/2008 |
| WO | WO 2009/126863 | 10/2009 |
| WO | WO 2010/057126 | 5/2010 |
| WO | WO 2010/059618 | 5/2010 |

OTHER PUBLICATIONS

Cooper et al., Bone vol. 27, pp. 375-381 (2000).
Coppola, Gary M. et al., "Perhydroquinolylbenzamides as Novel Inhibitors of 11.beta-Hydroxysteroid Dehydrogenase Type 1" Journal of Medicinal Chemistry, 48 (21), 6696-6712 Coden: Jmcmar; ISSN: 0022-2623, 2005.
Davani et al., J. Biol. Chem. vol. 275, pp. 34841-34844 (2000).
Demchenko, Chem. Hetero. Comp. vol. 36, pp. 985-988 (2000).
Desai et al., Tetrahedron Lett. vol. 34, pp. 7685-7688 (1993).
Donohue et al., J. Comb. Chem. vol. 4, pp. 23-32 (2002).
Evans et al., J. Med. Chem. vol. 35, pp. 3919-3927 (1992).
Fotsch C. et al., "11 [beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303.
Ganguly A.K. et al.; "Sythesis of heterocyclic compounds using radical reactions" Tetrahedron Letters, Elsevier, Amsterdam, NL, vol. 43, No. 38, Sep. 16, 2002, pp. 6865-6868.
Giacomelli et al. Eur. J. Org. Chem. vol. 3, pp. 537-541 (2003).
Hashigaki et al., Chem. Pharm. Bull. vol. 32, pp. 3561-3568 (1984).
Hosfield et al., J. Biol. Chem. vol. 280, pp. 4639-4648 (2005).
Ignatova et al., American Journal of Physiology—Endocrinology and Metabolism, 296(2):E367-E377 (2009).
International Preliminary Report on Patentability and Written Opinion for Application No. PCT/EP2008/051971, mailed Sep. 3, 2009.
International Search Report for Application No. PCT/EP2008/051971, mailed Nov. 6, 2008.
Johnson et al., J. Org. Chem. vol. 35, pp. 622-626 (1970).
Kondo, Kazumi et al: "Characterization of Orally Active Nonpeptide Vasopressin V2 Receptor Agonist" Journal of Medicinal Chemistry, vol. 45, No. 17, 2002, pp. 3805-3808.
Kondo, Kazumi et al: "Novel Design of Nonpeptide AVP V2 Receptor Agonists: Structural Requirements for and Agonist Having 1-(4-Aminobenzoyl)-2,3,4,5,-tetrahydro-1H-1-benezazepine as a Template" Journal of Medicinal Chemistry, vol. 43, No. 23, 2000, pp. 4388-4397.
Koteletsev et al., Proc. Nat'l Acad. Sci. vol. 94, pp. 14924-14929 (1997).
Leyendecker et al., Nouveau J. de Chimie vol. 9, pp. 13-19 (1985).
Mariani et al., Farmaco vol. 38, pp. 653-663 (1983).
Massa et al., J. Heterocycl. Chem. vol. 27, pp. 1805-1808 (1990).
Masuzaki et al., J. Clin. Invest. vol. 112, pp. 83-90 (2003).
Masuzaki et al., Science vol. 294, pp. 2166-2170 (2001).
McCullough et al., J. Chem. Soc. Perkin Trans. 1 vol. 20, pp. 2553-2560 (1996).
Moisan et al., Endocrinology, vol. 127, pp. 1450-1455 (1990).
Morton et al., J. Biol. Chem. vol. 276, pp. 41293-41300 (2001).
Nankervis et al.: "Calcium sensitiziazion as a positive inotropic mechanism . . . " Journal of Cardiovascular Pharmacology, vol. 24, No. 4, 1994, pp. 612-617.
Nieczypor et al., Eu. J. Org. Chem. vol. 2004, pp. 812-819 (2004).

Pending Claims for U.S. Appl. No. 11/665,103, filed Mar. 24, 2011.
Pending Claims for U.S. Appl. No. 12/092,223, filed Mar. 24, 2011.
Pending Claims for U.S. Appl. No. 12/092,230, filed Mar. 25, 2011.
Pending Claims for U.S. Appl. No. 12/293,709, filed Mar. 25, 2011.
Pending Claims for U.S. Appl. No. 12/294,475, filed Jul. 18, 2011.
Pending Claims for U.S. Appl. No. 12/304,501, filed Mar. 25, 2011.
Pending Claims for U.S. Appl. No. 12/307,999, filed May 23, 2011.
Pending Claims for U.S. Appl. No. 12/308,000, filed Mar. 28, 2011.
Pending Claims for U.S. Appl. No. 12/528,227, filed Mar. 28, 2011.
Pending Claims for U.S. Appl. No. 12/528,231, filed Mar. 28, 2011.
Pending Claims for U.S. Appl. No. 12/528,233, filed Mar. 29, 2011.
Pending Claims for U.S. Appl. No. 12/529,956, filed Mar. 29, 2011.
Pending Claims for U.S. Appl. No. 12/593,456, filed Mar. 29, 2011.
Pending Claims for U.S. Appl. No. 12/595,310, filed Mar. 29, 2011.
Pending Claims for U.S. Appl. No. 12/597,129, filed Mar. 29, 2011.
Pending Claims for U.S. Appl. No. 13/078,221, filed Apr. 1, 2011.
Pending Claims for U.S. Appl. No. 13/220,843, filed Aug. 30, 2011.
Rauz et al., Invest. Opthalmol. Vis. Sci. vol. 42, pp. 2037-2042 (2001).
Reed et al., Scand. J. Gastroentreol. vol. 15, pp. 51-56 (1980).
Schwartz et al., Nature vol. 404, pp. 661-671 (2000).
Seefelter et al., Chemische Berichte vol. 96, pp. 3243-3253 (1963).
Skowronska-Ptasinska et al: "Effect of Different Dialkylamino Groups on the Regioselectivity of Lithiation of 0-Protected 3-(Dialkylamino)phenols" Journal of Organic Chemistry, vol. 50, No. 15, 1985, pp. 2690-2698.
Sohar R et al: "Conformational Analysis of N-Acylazabycyclooctanes," Magnetic Resonance in Chemistry, John Wiley, Chichester, GB, vol. 23, No. 7, Jan. 1, 1985, pp. 506-513.
Souness et al., Steroids vol. 67, pp. 195-201 (2002).
Tabuchi, S. et al.: "Novel Potent Antagonists of Human Neuropeptide Y Y5 Receptor. Part 1: 2-Oxobenzothiazolin-3-acetic Acid Derivatives" Bioorganic & Medicinal Chemistry Letters, vol. 12, 2002, pp. 1171-1175.
Tannin et al., J. Biol. Chem. vol. 266, pp. 16653-16658 (1991).
Tomlinson et al., J. Clin. Endocrinol. Metab. vol. 87, pp. 57-62 (2002).
Villani, F.J. et al.; "Derivatives of 2-Azabicyclo[2.2.2]octane" Journal of Medicinal Chemistry, 1966, pp. 264-265.
Walker et al., J. Clin. Endocrinol. Metab. vol. 80, pp. 3155-3159 (1995).
Whitworth et al., J. Hypertens. vol. 20, pp. 1035-1043 (2002).
Whorwood et al., J. Clin. Endocrinol. Metab. vol. 86, pp. 2296-2308 (2001).
Willoughby C A et al: "Solid Phase Synthesis of Aryl Amines" Tetrahedron Letters, Elsevier, Amsterdam, NL, vol. 37, No. 40, Sep. 30, 1996, pp. 7181-7184 XP004030858 ISSN: 0040-4039 table 2; compound 1.
Wu et al., Toxicology vol. 236, pp. 1-6 (2007).
Yang et al., Bioorg. Med. Chem. Lett. vol. 8, pp. 107-112 (1998).
Yau et al., Proc. Nat'l Acad. Sci. vol. 98, pp. 4716-4721 (2001).
Yudt et al., Mol. Endocrinol. vol. 16, pp. 1719-1726 (2002).
Office Action for U.S. Appl. No. 13/128,045 dated Sep. 26, 2012.
Rauz et al., "Inhibition of 11beta-hydroxysteroid dehydrogenase type 1 lowers intraocular pressure in patients with ocular hypertension" Q. J. Med., 96:481-490 (2003).
Tomlinson, et al., "11beta-Hydroxysteroid Dehydrogenase Type 1: A Tissue-Specific Regulator of Glucocorticoid Response," Endocrine Reviews, 25(5):831-866 (2004).

N-ADAMANTYL BENZAMIDES AS INHIBITORS OF 11-β-HYDROXYSTEROID DEHYDROGENASE

CROSS-REFERENCE TO RELATED APPLICATIONS

This application is the United States national stage application, pursuant to 35 U.S.C. §371, of PCT/EP2008/051971, filed Feb. 19, 2008 which claims benefit of European Patent Application No. 07102956.5, filed Feb. 23, 2007.

The present invention relates to novel substituted benzamide based inhibitors, to their use in therapy, to pharmaceutical compositions comprising the compounds, to the use of said compounds in the manufacture of medicaments, and to therapeutic methods comprising the administration of said compounds. The present compounds modulate the activity of 11β-hydroxysteroid dehydrogenase type 1 (11βHSD1) and are accordingly useful in the treatment of diseases in which such a modulation is beneficial, such as the metabolic syndrome.

BACKGROUND OF THE INVENTION

The metabolic syndrome is a major global health problem. In the US, the prevalence in the adult population is currently estimated to be approximately 25%, and it continues to increase both in the US and worldwide. The metabolic syndrome is characterised by a combination of insulin resistance, dyslipidemia, obesity and hypertension leading to increased morbidity and mortality of cardiovascular diseases. People with the metabolic syndrome are at increased risk of developing frank type 2 diabetes, the prevalence of which is equally escalating.

In type 2 diabetes, obesity and dyslipidemia are also highly prevalent and around 70% of people with type 2 diabetes additionally have hypertension once again leading to increased mortality of cardiovascular diseases.

In the clinical setting, it has long been known that glucocorticoids are able to induce all of the cardinal features of the metabolic syndrome and type 2 diabetes.

11β-hydroxysteroid dehydrogenase type 1 (11βHSD1) catalyses the local generation of active glucocorticoid in several tissues and organs including predominantly the liver and adipose tissue, but also e.g. skeletal muscle, bone, pancreas, endothelium, ocular tissue and certain parts of the central nervous system. Thus, 11βHSD1 serves as a local regulator of gluco-corticoid actions in the tissues and organs where it is expressed (Tannin et al., *J. Biol. Chem.*, 266, 16653 (1991); Bujalska et al., *Endocrinology*, 140, 3188 (1999); Whorwood et al., *J Clin Endocrinol Metab.*, 86, 2296 (2001); Cooper et al., *Bone*, 27, 375 (2000); Davani et al., *J. Biol. Chem.*, 275, 34841 (2000); Brem et al., *Hypertension*, 31, 459 (1998); Rauz et al., *Invest. Opthalmol. Vis. Sci.*, 42, 2037 (2001); Moisan et al., *Endocrinology*, 127, 1450 (1990)).

The role of 11βHSD1 in the metabolic syndrome and type 2 diabetes is supported by several lines of evidence. In humans, treatment with the non-specific 11βHSD1 inhibitor carbenoxolone improves insulin sensitivity in lean healthy volunteers and people with type 2 diabetes. Likewise, 11βHSD1 knock-out mice are resistant to insulin resistance induced by obesity and stress. Additionally, the knock-out mice present with an anti-atherogenic lipid profile of decreased VLDL triglycerides and increased HDL-cholesterol. Conversely, mice that overexpress 11βHSD1 in adipocytes develop insulin resistance, hyperlipidemia and visceral obesity, a phenotype that resembles the human metabolic syndrome (Andrews et al., *J. Clin. Endocrinol. Metab.*, 88, 285 (2003); Walker et al., *J. Clin. Endocrinol. Metab.*, 80, 3155 (1995); Morton et al., *J. Biol. Chem.*, 276, 41293 (2001); Kotelevtsev et al., *Proc. Natl. Acad. Sci. USA*, 94, 14924 (1997); Masuzaki et al., *Science*, 294, 2166 (2001)).

The more mechanistic aspects of 11βHSD1 modulation and thereby modulation of intra-cellular levels of active glucocorticoid have been investigated in several rodent models and different cellular systems. 11βHSD1 promotes the features of the metabolic syndrome by increasing hepatic expression of the rate-limiting enzymes in gluconeogenesis, namely phosphoenolpyuvate carboxykinase and glucose-6-phosphatase, promoting the differentiation of preadipocytes into adipocytes thus facilitating obesity, directly and indirectly stimulating hepatic VLDL secretion, decreasing hepatic LDL uptake and increasing vessel contractility (Kotelevtsev et al., *Proc. Natl. Acad. Sci. USA*, 94, 14924 (1997); Morton et al., *J. Biol. Chem.* 276, 41293 (2001); Bujalska et al., *Endocrinology*, 140, 3188 (1999); Souness et al., *Steroids*, 67, 195 (2002), Brindley & Salter, *Prog. Lipid Res.*, 30, 349 (1991)).

WO 01/90090, WO 01/90091, WO 01/90092, WO 01/90093 and WO 01/90094 discloses various thiazol-sulfonamides as inhibitors of the human 11β-hydroxysteroid dehydrogenase type 1 enzyme, and further states that said compounds may be useful in treating diabetes, obesity, glaucoma, osteoporosis, cognitive disorders, immune disorders and depression. WO 2004/089470 discloses various substituted amides and the use thereof for stimulating 11β-hydroxysteroid dehydrogenase type 1. WO 2004/089415 and WO 2004/089416 discloses various combination therapies using an 11β-hydroxysteroid dehydrogenase type 1 inhibitor and respectively a glucocorticoid receptor agonist or an antihypertensive agent.

We have now found substituted benzamide based inhibitors that modulate the activity of 11βHSD1 leading to altered intracellular concentrations of active glucocorticoid. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g. the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

One object of the present invention is to provide compounds, pharmaceutical compositions and use of compounds that modulate the activity of 11βHSD1.

DEFINITIONS

The term "monovalent radical" shall mean a chemical group attached via a single bond.

The term "halogen" or "halo" means fluorine, chlorine, bromine or iodine.

The term "hydroxy" shall mean the radical —OH.

The term "carboxy" shall mean the radical —(C=O)OH.

The term "$C_1$-$C_6$alkyl" as used herein represents a saturated, branched or straight hydro-carbon group having from 1 to 6 carbon atoms, e.g. $C_1$-$C_2$alkyl, $C_1$-$C_3$alkyl, $C_1$-$C_4$alkyl, $C_1$-$C_6$alkyl, $C_2$-$C_6$alkyl, $C_3$-$C_6$alkyl, and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), and the like. The term "$C_1$-$C_4$alkyl" as used herein represents a saturated, branched or straight hydrocarbon group having from 1 to 4 carbon atoms, e.g. $C_1$-$C_2$alkyl, $C_1$-$C_3$alkyl, $C_1$-$C_4$alkyl, and the like. Representative examples are methyl, ethyl, propyl (e.g. prop-1-yl, prop-2-yl (or iso-propyl)), butyl (e.g. 2-methylprop-2-yl (or tert-butyl), but-2-yl), and the like.

The term "bridge" as used herein represents a connection in a saturated or partly saturated ring between two atoms of such ring that are not neighbors through a chain of 1 to 3 atoms selected from carbon, nitrogen, oxygen and sulfur. Representative examples of such connecting chains are —CH$_2$—, —CH$_2$CH$_2$—, —CH$_2$NHCH$_2$—, —CH$_2$CH$_2$CH$_2$—, —CH$_2$OCH$_2$—, and the like. In one embodiment according to the invention, the connecting chain is selected from the group consisting of —CH$_2$—, —CH$_2$CH$_2$—, or —CH$_2$OCH$_2$—.

The term "spiro atom" as used herein represents a carbon atom in a saturated or partly saturated ring that connects both ends of a chain of 3 to 7 atoms selected from carbon, nitrogen, oxygen and sulfur. Representative examples are —(CH$_2$)$_5$—, —(CH$_2$)$_3$—, —(CH$_2$)$_4$—, —CH$_2$NHCH$_2$CH$_2$—, —CH$_2$CH$_2$NHCH$_2$CH$_2$—, —CH$_2$NHCH$_2$CH$_2$CH$_2$—, —CH$_2$CH$_2$OCH$_2$—, —OCH$_2$CH$_2$O—, and the like.

The term "$C_3$-$C_{10}$cycloalkyl" as used herein represents a saturated monocyclic carbocyclic ring having from 3 to 10 carbon atoms, e.g. $C_{3-6}$-alkyl, $C_{3-8}$-alkyl, $C_{3-10}$-alkyl, and the like. Representative examples are cyclopropyl, cyclobutyl, cyclopentyl, cyclohexyl, cycloheptyl, cyclooctyl, and the like. $C_3$-$C_{10}$cycloalkyl is also intended to represent a saturated bicyclic carbocyclic ring having from 4 to 10 carbon atoms. Representative examples are decahydro-naphthalenyl, bicyclo[3.3.0]octanyl, and the like. $C_3$-$C_{10}$cycloalkyl is also intended to represent a saturated carbocyclic ring having from 3 to 10 carbon atoms and containing one or two carbon bridges. Representative examples are adamantyl, norbornanyl, nortricyclyl, bicyclo[3.2.1]octanyl, bicyclo[2.2.2]octanyl, tricyclo[5.2.1.0/2,6]decanyl, bicyclo[2.2.1]-heptyl, and the like. $C_3$-$C_{10}$cycloalkyl is also intended to represent a saturated carbocyclic ring having from 3 to 10 carbon atoms and containing one or more spiro atoms. Representative examples are spiro[2.5]octanyl, spiro[4.5]decanyl, and the like.

The term "aryl" as used herein is intended to include monocyclic, bicyclic or polycyclic carbocyclic aromatic rings. Representative examples are phenyl, naphthyl (e.g. naphth-1-yl, naphth-2-yl), anthryl (e.g. anthr-1-yl, anthr-9-yl), phenanthryl (e.g. phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g. biphenyl-2-yl, biphenyl-3-yl, biphenyl-4-yl), phenylnaphthyl (e.g. 1-phenylnaphth-2-yl, 2-phenylnaphth-1-yl), and the like. Aryl is also intended to include partially saturated bicyclic or polycyclic carbocyclic rings with at least one unsaturated moiety (e.g. a benzo moiety). Representative examples are, indanyl (e.g. indan-1-yl, indan-5-yl), indenyl (e.g. inden-1-yl, inden-5-yl), 1,2,3,4-tetrahydronaphtyl (e.g. 1,2,3,4-tetrahydronapht-1-yl, 1,2,3,4-tetrahydronapht-2-yl, 1,2,3,4-tetrahydronapht-6-yl), 1,2-dihydronaphtyl (e.g. 1,2-dihydronapht-1-yl, 1,2-dihydronapht-4-yl, 1,2-dihydronapht-6-yl), fluorenyl (e.g. fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g. benzonorborn-3-yl, benzonorborn-6-yl), 1,4-ethano-1,2,3,4-tetrahydronapthyl (e.g. 1,4-ethano-1,2,3,4-tetrahydronapth-2-yl, 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro[piperidine-4,2'-indane]-1-yl, spiro[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,2'-indane]-1-yl, spiro[piperidine-4,1'-indene]-1-yl, and the like.

The term "$C_3$-$C_{10}$heterocyclyl" as used herein represents a saturated 3 to 10 membered monocyclic ring, containing one or more heteroatoms selected from nitrogen, oxygen, sulfur, $S(=O)$ and $S(=O)_2$. Representative examples are aziridinyl (e.g. aziridin-1-yl), azetidinyl (e.g. azetidin-1-yl, azetidin-3-yl), oxetanyl, pyrrolidinyl (e.g. pyrrolidin-1-yl, pyrrolidin-2-yl, pyrrolidin-3-yl), imidazolidinyl (e.g. imidazolidin-1-yl, imidazolidin-2-yl, imidazolidin-4-yl), oxazolidinyl (e.g. oxazolidin-2-yl, oxazolidin-3-yl, oxazolidin-4-yl), thiazolidinyl (e.g. thiazolidin-2-yl, thiazolidin-3-yl, thiazolidin-4-yl), isothiazolidinyl, piperidinyl (e.g. piperidin-1-yl, piperidin-2-yl, piperidin-3-yl, piperidin-4-yl), homopiperidinyl (e.g. homopiperidin-1-yl, homopiperidin-2-yl, homopiperidin-3-yl, homopiperidin-4-yl), piperazinyl (e.g. piperazin-1-yl, piperazin-2-yl), morpholinyl (e.g. morpholin-2-yl, morpholin-3-yl, morpholin-4-yl), thiomorpholinyl (e.g. thiomorpholin-2-yl, thiomorpholin-3-yl, thiomorpholin-4-yl), 1-oxo-thiomorpholinyl, 1,1-dioxo-thiomorpholinyl, tetrahydrofuranyl (e.g. tetrahydrofuran-2-yl, tetrahydrofuran-3-yl), tetrahydrothienyl, tetrahydro-1,1-dioxothienyl, tetrahydropyranyl (e.g. 2-tetrahydropyranyl), tetrahydrothiopyranyl (e.g. 2-tetrahydrothiopyranyl), 1,4-dioxanyl, 1,3-dioxanyl, and the like. $C_3$-$C_{10}$heterocyclyl is also intended to represent a saturated 6 to 10 membered bicyclic ring containing one or more heteroatoms selected from nitrogen, oxygen, sulfur, $S(=O)$ and $S(=O)_2$. Representative examples are octahydroindolyl (e.g. octahydroindol-1-yl, octahydroindol-2-yl, octahydroindol-3-yl, octahydroindol-5-yl), decahydroquinolinyl (e.g. decahydroquinolin-1-yl, decahydroquinolin-2-yl, decahydroquinolin-3-yl, decahydroquinolin-4-yl, decahydroquinolin-6-yl), decahydroquinoxalinyl (e.g. decahydroquinoxalin-1-yl, decahydroquinoxalin-2-yl, decahydroquinoxalin-6-yl) and the like. $C_3$-$C_{10}$heterocyclyl is also intended to represent a saturated 6 to 10 membered ring containing one or more heteroatoms selected from nitrogen, oxygen, sulfur, $S(=O)$ and $S(=O)_2$ and having one or two bridges. Representative examples are 3-azabicyclo-[3.2.2]nonyl, 2-azabicyclo[2.2.1]heptyl, 3-azabicyclo[3.1.0]hexyl, 2,5-diazabicyclo-[2.2.1]heptyl, atropinyl, tropinyl, quinuclidinyl, 1,4-diazabicyclo[2.2.2]octanyl, and the like. $C_3$-$C_{10}$heterocyclyl is also intended to represent a 6 to 10 membered saturated ring containing one or more heteroatoms selected from nitrogen, oxygen, sulfur, $S(=O)$ and $S(=O)_2$ and containing one or more spiro atoms. Representative examples are 1,4-dioxaspiro[4.5]decanyl (e.g. 1,4-dioxaspiro[4.5]decan-2-yl, 1,4-dioxaspiro[4.5]decan-7-yl), 1,4-dioxa-8-azaspiro[4.5]decanyl (e.g. 1,4-dioxa-8-azaspiro[4.5]decan-2-yl, 1,4-dioxa-8-azaspiro[4.5]decan-8-yl), 8-azaspiro[4.5]decanyl (e.g. 8-azaspiro[4.5]decan-1-yl, 8-azaspiro[4.5]decan-8-yl), 2-azaspiro[5.5]undecanyl (e.g. 2-azaspiro[5.5]undecan-2-yl), 2,8-diazaspiro[4.5]decanyl (e.g. 2,8-diazaspiro[4.5]decan-2-yl, 2,8-diazaspiro[4.5]decan-8-yl), 2,8-diazaspiro[5.5]undecanyl (e.g. 2,8-diazaspiro[5.5]undecan-2-yl), 1,3,8-triazaspiro[4.5]decanyl (e.g. 1,3,8-triazaspiro[4.5]decan-1-yl, 1,3,8-triazaspiro[4.5]decan-3-yl, 1,3,8-triazaspiro[4.5]decan-8-yl), and the like.

The term "heteroaryl" as used herein is intended to include monocyclic heterocyclic aromatic rings containing one or more heteroatoms selected from nitrogen, oxygen, sulfur, SO and $S(=O)_2$. Representative examples are pyrrolyl (e.g. pyrrol-1-yl, pyrrol-2-yl, pyrrol-3-yl), furanyl (e.g. furan-2-yl, furan-3-yl), thienyl (e.g. thien-2-yl, thien-3-yl), oxazolyl (e.g. oxazol-2-yl, oxazol-4-yl, oxazol-5-yl), thiazolyl (e.g. thiazol-2-yl, thiazol-4-yl, thiazol-5-yl), imidazolyl (e.g. imidazol-2-yl, imidazol-4-yl, imidazol-5-yl), pyrazolyl (e.g. pyrazol-1-yl, pyrazol-3-yl, pyrazol-5-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), 1,2,3-triazolyl (e.g. 1,2,3-triazol-1-yl, 1,2,3-triazol-4-yl, 1,2,3-triazol-5-yl), 1,2,4-triazolyl (e.g. 1,2,4-triazol-1-yl, 1,2,4-triazol-3-yl, 1,2,4-triazol-5-yl), 1,2,3-oxadiazolyl (e.g. 1,2,3-oxadiazol-4-yl, 1,2,3-oxadiazol-5-yl), 1,2,4-oxadiazolyl (e.g. 1,2,4-oxadiazol-3-yl, 1,2,4-oxadiazol-5-yl), 1,2,5-oxadiazolyl (e.g. 1,2,5-oxadiazol-3-yl, 1,2,5-oxadiazol-4-yl), 1,3,4-oxadiazolyl (e.g. 1,3,4-oxadiazol-2-yl, 1,3,4-oxadiazol-5-yl), 1,2,3-thiadiazolyl (e.g. 1,2,3-thiadiazol-4-yl, 1,2,3-thiadiazol-5-yl), 1,2,4-thiadiazolyl (e.g. 1,2,4-thiadiazol-3-yl, 1,2,4-thiadiazol-5-yl), 1,2,5-thiadiazolyl (e.g. 1,2,5-thiadiazol-3-yl, 1,2,5-thiadiazol-4-yl), 1,3,4-thiadiazolyl (e.g. 1,3,4-thiadiazol-2-yl, 1,3,4-thiadiazol-5-yl), tetrazolyl (e.g. tetrazol-1-yl, tetrazol-5-yl), pyranyl (e.g. pyran-2-yl), pyridinyl (e.g. pyridine-2-yl, pyridine-3-yl, pyridine-4-yl), pyridazinyl (e.g. pyridazin-2-yl, pyridazin-3-yl), pyrimidinyl (e.g. pyrimidin-2-yl, pyrimidin-4-yl, pyrimidin-5-yl), pyrazinyl, 1,2,3-triazinyl, 1,2,4-triazinyl, 1,3,5-triazinyl, thiadiazinyl, azepinyl, azecinyl, and the like. Heteroaryl is also intended to include bicyclic heterocyclic aromatic rings containing one or more heteroatoms selected from nitrogen, oxygen, sulfur, $S(=O)$ and $S(=O)_2$. Representative examples are indolyl (e.g. indol-1-yl, indol-2-yl, indol-3-yl, indol-5-yl), isoindolyl, benzofuranyl (e.g. benzo[b]furan-2-yl, benzo[b]furan-3-yl, benzo[b]furan-5-yl, benzo[c]furan-2-yl, benzo[c]furan-3-yl, benzo[c]furan-5-yl), benzothienyl (e.g. benzo[b]thien-2-yl, benzo[b]thien-3-yl, benzo[b]thien-5-yl, benzo[c]thien-2-yl, benzo[c]thien-3-yl, benzo[c]thien-5-yl), indazolyl (e.g. indazol-1-yl, indazol-3-yl, indazol-5-yl), indolizinyl (e.g. indolizin-1-yl, indolizin-3-yl), benzopyranyl (e.g. benzo[b]pyran-3-yl, benzo[b]pyran-6-yl, benzo[c]pyran-1-yl, benzo[c]pyran-7-yl), benzimidazolyl (e.g. benzimidazol-1-yl, benzimidazol-2-yl, benzimidazol-5-yl), benzothiazolyl (e.g. benzothiazol-2-yl, benzothiazol-5-yl), benzisothiazolyl, benzoxazolyl, benzisoxazolyl, benzoxazinyl, benzotriazolyl, naphthyridinyl (e.g. 1,8-naphthyridin-2-yl, 1,7-naphthyridin-2-yl, 1,6-naphthyridin-2-yl), phthalazinyl (e.g. phthalazin-1-yl, phthalazin-5-yl), pteridinyl, purinyl (e.g. purin-2-yl, purin-6-yl, purin-7-yl, purin-8-yl, purin-9-yl), quinazolinyl (e.g. quinazolin-2-yl, quinazolin-4-yl, quinazolin-6-yl), cinnolinyl, quinoliny (e.g. quinolin-2-yl, quinolin-3-yl, quinolin-4-yl, quinolin-6-yl), isoquinolinyl (e.g. isoquinolin-1-yl, isoquinolin-3-yl, isoquinolin-4-yl), quinoxalinyl (e.g. quinoxalin-2-yl, quinoxalin-5-yl), pyrrolopyridinyl (e.g. pyrrolo[2,3-b]pyridinyl, pyrrolo[2,3-c]pyridinyl, pyrrolo[3,2-c]pyridinyl), furopyridinyl (e.g. furo[2,3-b]pyridinyl, furo[2,3-c]pyridinyl, furo[3,2-c]pyridinyl), thienopyridinyl (e.g. thieno[2,3-b]pyridinyl, thieno[2,3-c]pyridinyl, thieno[3,2-c]pyridinyl), imidazopyridinyl (e.g. imidazo[4,5-b]pyridinyl, imidazo[4,5-c]pyridinyl, imidazo[1,5-a]pyridinyl, imidazo[1,2-a]pyridinyl), imidazopyrimidinyl (e.g. imidazo[1,2-a]pyrimidinyl, imidazo[3,4-a]pyrimidinyl), pyrazolopyridinyl (e.g. pyrazolo[3,4-b]pyridinyl, pyrazolo[3,4-c]pyridinyl, pyrazolo[1,5-a]pyridinyl), pyrazolopyrimidinyl (e.g. pyrazolo[1,5-a]pyrimidinyl, pyrazolo[3,4-d]pyrimidinyl), thiazolopyridinyl (e.g. thiazolo[3,2-d]pyridinyl), thiazolopyrimidinyl (e.g. thiazolo[5,4-d]pyrimidinyl), imdazothiazolyl (e.g. imidazo[2,1-b]thiazolyl), triazolopyridinyl (e.g. triazolo[4,5-b]pyridinyl), triazolopyrimidinyl (e.g. 8-azapurinyl), and the like. Heteroaryl is also intended to include polycyclic heterocyclic aromatic rings containing one or more heteroatoms selected from nitrogen, oxygen, sulfur, $S(=O)$ and $S(=O)_2$. Representative examples are carbazolyl (e.g. carbazol-2-yl, carbazol-3-yl, carbazol-9-yl), phenoxazinyl (e.g. phenoxazin-10-yl), phenazinyl (e.g. phenazin-5-yl), acridinyl (e.g. acridin-9-yl, acridin-10-yl), phenothiazinyl (e.g. phenothiazin-10-yl), carbolinyl (e.g. pyrido[3,4-b]indol-1-yl, pyrido[3,4-b]indol-3-yl), phenanthrolinyl (e.g. phenanthrolin-5-yl), and the like. Heteroaryl is also intended to include partially saturated monocyclic, bicyclic or polycyclic heterocyclic rings containing one or more heteroatoms selected from nitrogen, oxygen, sulfur, $S(=O)$ and $S(=O)_2$. Representative examples are pyrrolinyl, pyrazolinyl, imidazolinyl (e.g. 4,5-dihydroimidazol-2-yl, 4,5-dihydroimidazol-1-yl), indolinyl (e.g. 2,3-dihydroindol-1-yl, 2,3-dihydroindol-5-yl), dihydrobenzofuranyl (e.g. 2,3-dihydrobenzo[b]furan-2-yl, 2,3-dihydrobenzo[b]furan-4-yl), dihydrobenzothienyl (e.g. 2,3-dihydrobenzo[b]thien-2-yl, 2,3-dihydrobenzo[b]thien-5-yl), 4,5,6,7-tetrahydrobenzo[b]furan-5-yl), dihydrobenzopyranyl (e.g. 3,4-dihydrobenzo[b]pyran-3-yl, 3,4-dihydrobenzo[b]pyran-6-yl, 3,4-dihydrobenzo-[c]pyran-1-yl, dihydrobenzo[c]pyran-7-yl), oxazolinyl (e.g. 4,5-dihydrooxazol-2-yl, 4,5-dihydrooxazol-4-yl, 4,5-dihydrooxazol-5-yl), isoxazolinyl, oxazepinyl, tetrahydroindazolyl (e.g. 4,5,6,7-tetrahydroindazol-1-yl, 4,5,6,7-tetrahydroindazol-3-yl, 4,5,6,7-tetrahydroindazol-4-yl, 4,5,6,7-tetrahydroindazol-6-yl), tetrahydrobenzimidazolyl (e.g. 4,5,6,7-tetrahydrobenzimidazol-1-yl, 4,5,6,7-tetrahydrobenzimidazol-5-yl), tetrahydroimidazo[4,5-c]pyridyl (e.g. 4,5,6,7-tetrahydroimidazo[4,5-c]pyrid-1-yl, 4,5,6,7-tetrahydroimidazo[4,5-c]pyrid-5-yl, 4,5,6,7-tetrahydroimidazo[4,5-c]pyrid-6-yl), tetrahydroquinolinyl (e.g. 1,2,3,4-tetrahydroquinolinyl, 5,6,7,8-tetrahydroquinolinyl), tetrahydroisoquinolinyl (e.g. 1,2,3,4-tetrahydroisoquinolinyl, 5,6,7,8-tetrahydroisoquinolinyl), tetrahydroquinoxalinyl (e.g. 1,2,3,4-tetrahydroquinoxalinyl, 5,6,7,8-tetrahydroquinoxalinyl), and the like. Heteroaryl is also intended to include partially saturated bicyclic or polycyclic heterocyclic rings containing one or more spiro atoms. Representative examples are spiro[isoquinoline-3,1'-cyclohexan]-1-yl, spiro[piperidine-4,1'-benzo[c]thiophen]-1-yl, spiro[piperidine-4,1'-benzo[c]furan]-1-yl, spiro[piperidine-4,3'-benzo[b]furan]-1-yl, spiro[piperidine-4,3'-coumarin]-1-yl, and the like.

The term "monocyclic heteroaryl" as used herein is intended to include monocyclic heterocyclic aromatic rings as defined above.

The term "bicyclic heteroaryl" as used herein is intended to include bicyclic heterocyclic aromatic rings as defined above.

The term "4 to 6 membered ring" as used herein represents a saturated 3 to 6 membered monocyclic ring, containing one nitrogen and it might contain a further heteroatom selected from oxygen, sulfur, S(=O) and S(=O)$_2$ and it is intended to include pyrrolidinyl (e.g. pyrrolidin-1-yl, pyrrolidin-2-yl, pyrrolidin-3-yl), piperidinyl (e.g. piperidin-1-yl, piperidin-2-yl, piperidin-3-yl, piperidin-4-yl), morpholinyl (e.g. morpholin-2-yl, morpholin-3-yl, morpholin-4-yl), thiomorpholinyl (e.g. thiomorpholin-2-yl, thiomorpholin-3-yl, thiomorpholin-4-yl), 1-oxo-thiomorpholinyl, 1,1-dioxo-thiomorpholinyl, aziridinyl (e.g. aziridin-1-yl), azetidinyl (e.g. azetidin-1-yl, azetidin-3-yl), azetidine and the like.

The term $C_1$-$C_4$alkylcarbonyl as used herein refers to the radical $C_1$-$C_4$alkyl-C(=O)—.

Certain of the defined terms may occur more than once in the structural formulae, and upon such occurrence each term shall be defined independently of the other.

Certain of the defined terms may occur in combinations, and it is to be understood that the first mentioned radical is a substituent on the subsequently mentioned radical, where the point of substitution, i.e. the point of attachment to another part of the molecule, is on the last mentioned of the radicals.

The term "treatment" is defined as the management and care of a patient for the purpose of combating or alleviating the disease, condition or disorder, and the term includes the administration of the active compound to prevent the onset of the symptoms or complications, or alleviating the symptoms or complications, or eliminating the disease, condition, or disorder.

The term "pharmaceutically acceptable" is defined as being suitable for administration to humans without adverse events.

The term "prodrug" is defined as a chemically modified form of the active drug, said prodrug being administered to the patient and subsequently being converted to the active drug. Techniques for development of prodrugs are well known in the art.

SUMMARY OF THE INVENTION

In one aspect of the invention substituted benzamide based inhibitors that modulate the activity of 11βHSD1 leading to altered intracellular concentrations of active glucocorticoid are provided. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g. the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

One object of the present invention is to provide compounds, pharmaceutical compositions and use of compounds that modulate the activity of 11βHSD1.

The present invention furthermore relates to the use in therapy of the compounds according to the invention, to pharmaceutical compositions comprising the compounds, to the use of said compounds in the manufacture of medicaments, and to therapeutic methods comprising the administration of said compounds.

DETAILED DESCRIPTION OF THE INVENTION

The invention provides for a compound of the general formula (I):

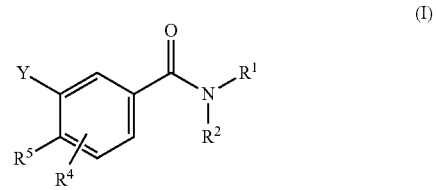

wherein $R^1$ is selected from the group consisting of hydrogen, methyl, ethyl, isopropyl and cyclopropyl and $R^2$ is selected from the group consisting of a monovalent radical having one of the following formulae, wherein the symbol * denotes the point of attachment:

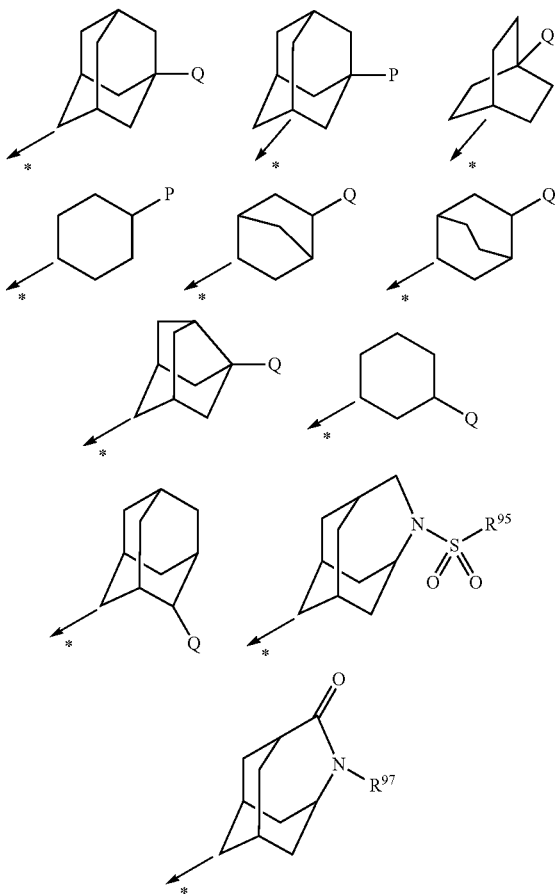

or $R^1$ and $R^2$ together with the nitrogen to which they are attached is selected from the group consisting of one of the following formulae wherein the symbol * denotes the point of attachment:

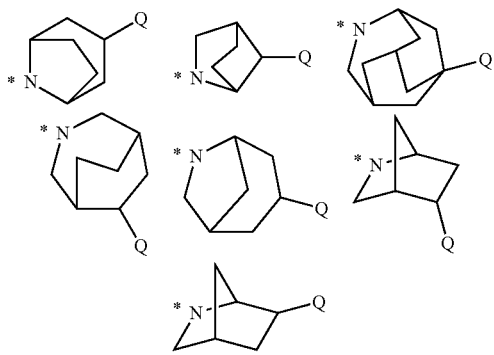

Q is selected is selected from the group consisting of hydroxy, carboxy, —S(=O)$_2$R$^6$, and S(=O)$_2$NH$_2$;

P is selected from the group consisting of —S(=O)$_2$R$^6$, carboxy and —S(=O)$_2$NH$_2$;

R$^6$ is selected from the group consisting of C$_1$-C$_4$alkyl, phenyl, pyridine and C$_3$-C$_{10}$cycloalkyl, wherein said C$_1$-C$_4$alkyl, phenyl, pyridine and C$_3$-C$_{10}$cycloalkyl are optionally substituted with one or two independently selected R$^7$;

R$^7$ is selected from the group consisting of hydrogen, methyl, ethyl, cyclopropyl, —O—CH$_3$, —O-cyclopropyl, —O-isopropyl, hydroxy, and halogen, wherein said methyl, ethyl, cyclopropyl, —O—CH$_3$, —O-cyclopropyl and —O-isopropyl is optionally substituted with one substituent selected from the group consisting of hydroxy and halogen;

R$^4$ is selected from the group consisting of hydrogen, C$_1$-C$_4$alkyl substituted with R$^{12}$ and R$^{13}$, —O—(C$_1$-C$_4$alkyl) substituted with R$^{12}$ and R$^{13}$, trifluoromethyl, —CN, halogen, —S(=O)$_2$methyl, —S(=O)$_2$ethyl, —S(=O)$_2$cyclopropyl, —S(=O)$_2$NR$^{10}$R$^{11}$ and —C(=O)NR$^{10}$R$^{11}$;

R$^{95}$ is selected from the group consisting of C$_1$-C$_6$alkyl, phenyl, pyridine, pyrimidine, cyclopropyl, cyclobutyl and cyclohexyl, wherein said C$_1$-C$_6$alkyl, phenyl, pyridine, pyrimidine, cyclopropyl, cyclobutyl and cyclohexyl are optionally substituted with one or two independently selected R$^{96}$;

R$^{96}$ is selected from the group consisting of halogen, hydroxy, oxo, trifluoromethyl, C$_1$-C$_6$alkyl, and —S(=O)$_2$methyl;

R$^{97}$ is selected from the group consisting of hydrogen and C$_1$-C$_6$alkyl;

R$^{12}$ and R$^{13}$ are each independently selected from the group consisting of hydrogen, —O—(C$_1$-C$_4$alkyl), halogen, carboxy and hydroxy;

R$^5$ is selected from the group consisting of hydrogen, C$_1$-C$_4$alkyl substituted with R$^{16}$, trifluoromethyl, —CN, halogen, C$_1$-C$_4$alkylcarbonyl substituted with R$^{18}$, —S(=O)$_2$R$^{17}$, —S(=O)$_2$NR$^{14}$R$^{15}$, and —S—R$^{17}$;

R$^{10}$ and R$^{11}$ are each independently selected from the group consisting of hydrogen, and C$_1$-C$_4$alkyl; or R$^{10}$ and R$^{11}$ together with the nitrogen to which they are attached form a 4 to 6 membered ring, wherein said C$_1$-C$_4$alkyl and each carbon atom in said 4 to 6 membered ring optionally is substituted with one or two substituents independently selected from the group consisting of hydroxy and halogen;

R$^{14}$ and R$^{15}$ are each independently selected from the group consisting of hydrogen, and C$_1$-C$_4$alkyl; or R$^{14}$ and R$^{15}$ together with the nitrogen to which they are attached form a 4 to 6 membered ring, wherein said C$_1$-C$_4$alkyl and each carbon atom in said 4 to 6 membered ring optionally is substituted with one or two substituents independently selected from the group consisting of hydroxy and halogen;

R$^{16}$ and R$^{18}$ are each independently selected from the group consisting of hydrogen, —O-methyl, methyl, cyclopropyl, halogen, —S(=O)$_2$-methyl, —S(=O)$_2$-ethyl, —C(=O)NH$_2$, —C(=O)N—CH$_3$CH$_3$, carboxy, and hydroxy;

R$^{17}$ is selected from the group consisting of hydrogen and C$_1$-C$_6$alkyl, wherein said C$_1$-C$_6$alkyl is optionally substituted with one or two substituents selected from the group consisting of hydroxy and halogen;

Y is selected from the group consisting of —X$^1$—X$^2$—X$^3$—R$^3$, —X$^{10}$, —CR$^{72}$R$^{73}$—O—CR$^{70}$R$^{71}$—R$^3$, —CR$^{72}$R$^{73}$—S—CR$^{70}$R$^{71}$—R$^3$, —CR$^{72}$R$^{73}$—S(=O)$_2$—CR$^{70}$R$^{71}$—R$^3$, —CR$^{72}$R$^{73}$—NR$^{25}$—S(=O)$_2$—R$^3$, —CR$^{72}$R$^{73}$—CR$^{70}$R$^{71}$—S(=O)$_2$—R$^3$, —CR$^{72}$R$^{73}$—CR$^{70}$R$^{71}$—O—R$^3$, —CR$^{72}$R$^{73}$—CR$^{70}$R$^{71}$—S—R$^3$, —CR$^{72}$R$^{73}$—CR$^{70}$R$^{71}$—NR$^{25}$—R$^3$, —O—CR$^{44}$R$^{45}$—S(=O)$_2$—R$^3$, —CR$^{72}$R$^{73}$—O—R$^3$, —CR$^{72}$R$^{73}$—S—R$^3$, —CR$^{72}$R$^{73}$—S(=O)$_2$—R$^3$, —CR$^{72}$R$^{73}$—NR$^{25}$—R$^3$, —CR$^{72}$R$^{73}$—S(=O)$_2$—R$^3$, —O—R$^{103}$, —O—CR$^{44}$R$^{45}$—, —O—CR$^{44}$R$^{45}$—R$^{103}$, —CR$^{72}$R$^{73}$—CR$^{44}$R$^{45}$—R$^{103}$, —O—CR$^{44}$R$^{45}$—CR$^{70}$R$^{71}$—R$^{103}$, —CR$^{72}$R$^{73}$—CR$^{44}$R$^{45}$—CR$^{70}$R$^{71}$—R$^{103}$, and —CH$_2$R$^{103}$;

X$^1$ is selected from the group consisting of —S—, —S(=O)—, and —S(=O)$_2$—;

X$^2$ is absent or is selected from the group consisting of —O—, —CR$^{44}$R$^{45}$—, —S—, —S(=O)—, —S(=O)$_2$— and —NR$^{25}$—;

X$^3$ is absent or is selected from the group consisting of —O—, —CR$^{70}$R$^{71}$—, —S—, —S(=O)—, —S(=O)$_2$—, and —NR$^{125}$—;

X$^{10}$ is selected from the group consisting of C$_3$-C$_{10}$cycloalkyl substituted with R$^{19}$ and phenyl substituted with R$^{22}$;

each R$^{19}$ is independently selected from the group consisting of —CN, —C(=O)R$^{46}$, —CH(OH)—R$^{47}$, —(CR$^{44}$R$^{45}$)$_m$—C(=O)—NR$^{48}$R$^{49}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{50}$, —(CR$^{44}$R$^{45}$)$_m$—NR$^{48}$C(=O)—NR$^{48}$R$^{49}$, —(CR$^{44}$R$^{45}$)$_m$—C=C—R$^{51}$R$^{52}$, —(CR$^{44}$R$^{45}$)$_m$—C≡C—R$^{53}$, —(CR$^{44}$R$^{45}$)$_m$—C$_3$-C$_{10}$cycloalkyl substituted with R$^{55}$, and —(CR$^{44}$R$^{45}$)$_m$-aryl substituted with R$^{56}$ and R$^{57}$.

each R$^{22}$ is independently selected from the group consisting of halogen, —CN, hydroxy, —C(=O)OH, —C(=O)R$^{46}$, —CH(OH)—R$^{47}$, hydroxy, —(CR$^{44}$R$^{45}$)$_m$—C(=O)—NR$^{48}$R$^{49}$, —(CR$^{44}$R$^{45}$)$_m$—NR$^{48}$C(=O)R$^{46}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{59}$, —(CR$^{44}$R$^{45}$)$_m$—NR$^{48}$R$^{49}$, —(CR$^{44}$R$^{45}$)$_m$—NR$^{48}$C(=O)—NR$^{48}$R$^{49}$, —(CR$^{44}$R$^{45}$)$_m$—C=C—R$^{51}$R$^{52}$, —(CR$^{44}$R$^{45}$)$_m$—C≡C—R$^{53}$, —(CR$^{44}$R$^{45}$)$_m$—C$_3$-C$_{10}$heterocyclyl substituted with R$^{54}$, —(CR$^{44}$R$^{45}$)$_m$—C$_3$-C$_{10}$cycloalkyl substituted with R$^{55}$, —(CR$^{44}$R$^{45}$)$_m$-aryl substituted with R$^{56}$ and R$^{57}$ and —(CR$^{44}$R$^{45}$)$_m$-heteroaryl substituted with R$^{56}$ and R$^{57}$;

R$^{24}$ is selected from the group consisting of —C(=O)—R$^{26}$, —S(=O)$_2$—R$^{27}$, heteroaryl substituted with R$^{28}$, and aryl substituted with R$^{29}$;

R$^{25}$ is selected from the group consisting of hydrogen, methyl, ethyl, isobutyl, isopropyl and cyclopropyl;

R$^{125}$ is selected from the group consisting of hydrogen, methyl, ethyl, isobutyl, isopropyl and cyclopropyl;

$R^3$ is selected from the group consisting of $C_3$-$C_{10}$heterocyclyl substituted with $R^{30}$ and $R^{31}$, $C_3$-$C_{10}$cycloalkyl substituted with $R^{90}$ and $R^{91}$, aryl substituted with $R^{30}$ and $R^{31}$, heteroaryl substituted with $R^{90}$ and $R^{91}$, —C(=O)$R^{32}$, —CH(OH)—$R^{33}$, —$(CR^{44}R^{45})_n$—C(=O)—$NR^{34}R^{35}$, —$(CR^{44}R^{45})_n$—$NR^{36}C(=O)R^{37}$, —$(CR^{44}R^{45})OR^{35}$, —$(CR^{44}R^{45})_n$—$SR^{35}$, —$(CR^{44}R^{45})_n$—S(=O)$_2R^{39}$, —$(CR^{44}R^{45})_n$—S(=O)$_2NR^{34}R^{35}$, —$(CR^{44}R^{45})_n$—$NR^{34}S(=O)_2$—$R^{40}$, —$(CR^{44}R^{45})_n$—$NR^{34}R^{35}$, —$(CR^{44}R^{45})_n$—$NR^{34}C(=O)$—$NR^{34}R^{35}$, —$(CR^{44}R^{45})_n$—C=C—$R^{41}R^{42}$, and —$(CR^{44}R^{45})_n$—C≡C—$R^{43}$, n is selected from the group consisting of 0, 1 and 2;

$R^{44}$ and $R^{45}$ are each independently selected from the group consisting hydrogen, halogen, $C_1$-$C_6$alkyl and $C_3$-$C_{10}$cycloalkyl, wherein said $C_1$-$C_6$alkyl and $C_3$-$C_{10}$cycloalkyl are optionally substituted with one or two substituents selected independently from the group consisting halogen, hydroxy and oxo; or $R^{44}$ and $R^{45}$ together with the carbon atom to which they are attached form a cyclopropyl or cyclobutyl ring, wherein said ring are optionally substituted with hydroxy or halogen;

$R^{70}$ and $R^{71}$ are each independently selected from the group consisting hydrogen, halogen, $C_1$-$C_6$alkyl and $C_3$-$C_{10}$cycloalkyl, wherein said $C_1$-$C_6$alkyl and $C_3$-$C_{10}$cycloalkyl are optionally substituted with one or two substituents selected independently from the group consisting halogen, hydroxy and oxo; or $R^{44}$ and $R^{45}$ together with the carbon atom to which they are attached form a cyclopropyl or cyclobutyl ring, wherein said ring are optionally substituted with hydroxy or halogen;

$R^{72}$ and $R^{73}$ are each independently selected from the group consisting hydrogen, halogen, $C_1$-$C_6$alkyl and $C_3$-$C_{10}$cycloalkyl, wherein said $C_1$-$C_6$alkyl and $C_3$-$C_{10}$cycloalkyl are optionally substituted with one or two substituents selected independently from the group consisting halogen, hydroxy and oxo; or $R^{44}$ and $R^{45}$ together with the carbon atom to which they are attached form a cyclopropyl or cyclobutyl ring, wherein said ring are optionally substituted with hydroxy or halogen;

$R^{30}$, $R^{31}$, $R^{42}$ and $R^{43}$ are each independently selected from the group consisting of hydrogen, halogen, —CN, —C(=O)OH, —C(=O)$R^{46}$, —CH(OH)—$R^{47}$, trifluoromethyl, hydroxy, —$(CR^{44}R^{45})_m$—C(=O)—$NR^{48}R^{49}$, —$(CR^{44}R^{45})_m$—$NR^{48}C(=O)R^{46}$, —$(CR^{44}R^{45})_m$—$OR^{49}$, —$(CR^{44}R^{45})_m$—$SR^{49}$, —$(CR^{44}$—$R^{45})_m$—S(=O)$_2R^{50}$, —$(CR^{44}R^{45})_m$—S(=O)$_2NR^{48}R^{49}$, —$(CR^{44}R^{45})_m$—$NR^{48}S(=O)_2R^{50}$, —$(CR^{44}R^{45})_m$—$NR^{48}R^{49}$, —$(CR^{44}R^{45})_m$—$NR^{45}C(=O)$—$NR^{48}R^{49}$, —$(CR^{44}R^{45})_m$—C=$CR^{51}R^{52}$, —$(CR^{44}R^{45})_m$—C≡C—$R^{53}$, —$(CR^{44}R^{45})_m$—$C_3$-$C_{10}$heterocyclyl substituted with $R^{54}$, —$(CR^{44}R^{45})_m$—$C_3$-$C_{10}$cycloalkyl substituted with $R^{55}$, —$(CR^{44}R^{45})_m$-aryl substituted with $R^{56}$ and $R^{57}$ and —$(CR^{44}R^{45})_m$-heteroaryl substituted with $R^{56}$ and $R^{57}$;

$R^{90}$ and $R^{91}$ are each independently selected from the group consisting of hydrogen, halogen, =O, —CN, —C(=O)OH, —C(=O)$R^{46}$, —CH(OH)—$R^{47}$, hydroxy, trifluoromethyl, —$(CR^{44}R^{45})_m$—C(=O)—$NR^{48}R^{49}$, —$(CR^{44}R^{45})_m$—$NR^{45}C(=O)R^{46}$, —$(CR^{44}R^{45})_m$—$OR^{49}$, —$(CR^{44}R^{45})_m$—$SR^{49}$, —$(CR^{44}R^{45})_m$—S(=O)$_2R^{50}$, —$(CR^{44}R^{45})_m$—S(=O)$_2NR^{48}R^{49}$, —$(CR^{44}R^{45})_m$—$NR^{45}S(=O)_2R^{50}$, —$(CR^{44}R^{45})_m$—$NR^{48}R^{49}$, —$(CR^{44}R^{45})_m$—$NR^{45}C(=O)$—$NR^{48}R^{49}$, —$(CR^{44}R^{45})_m$—C=$CR^{51}R^{52}$, —$(CR^{44}R^{45})_m$—C≡C—$R^{53}$, —$(CR^{44}R^{45})_m$—$C_3$-$C_{10}$heterocyclyl substituted with $R^{54}$, —$(CR^{44}R^{45})_m$—$C_3$-$C_{10}$cycloalkyl substituted with $R^{55}$, —$(CR^{44}R^{45})_m$-aryl substituted with $R^{56}$ and $R^{57}$ and —$(CR^{44}R^{45})_m$-heteroaryl substituted with $R^{56}$ and $R^{57}$;

m is 0 or 1;

$R^{32}$, $R^{33}$, $R^{37}$, $R^{38}$, $R^{39}$, $R^{40}$ and $R^{41}$ are each independently selected from the group consisting of hydrogen, $C_1$-$C_6$alkyl, $C_3$-$C_{10}$heterocyclyl, $C_3$-$C_{10}$cycloalkyl, aryl and heteroaryl, wherein said $C_1$-$C_6$alkyl, $C_3$-$C_{10}$heterocyclyl, $C_3$-$C_{10}$cycloalkyl, aryl and heteroaryl are optionally substituted with one, two or three independently selected $R^{58}$;

$R^{34}$, $R^{35}$, and $R^{36}$ are each independently selected from the group consisting of hydrogen, $C_1$-$C_6$alkyl, $C_3$-$C_{10}$cycloalkyl and heteroaryl, wherein said $C_1$-$C_6$alkyl, $C_3$-$C_{10}$cycloalkyl and heteroaryl are optionally substituted with one, two or three substituents independently selected from the group consisting of halogen, methyl, ethyl and hydroxy; or $R^{34}$ and $R^{35}$ together with the nitrogen to which they are attached form a 4 to 6 membered ring, wherein said 4 to 6 membered ring optionally is substituted with one or two substituents independently selected from the group consisting of hydroxy or halogen;

$R^{26}$, $R^{27}$, $R^{46}$, $R^{47}$, $R^{49}$, $R^{50}$, $R^{51}$, $R^{52}$ and $R^{53}$ are each independently selected from the group consisting of hydrogen, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy;

$R^{54}$, $R^{55}$, $R^{56}$ and $R^{57}$ are each independently selected from the group consisting of hydrogen, halogen, —CN, trifluoromethyl, —OCH$_2$CH$_2$OH, hydroxyl, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy;

$R^{48}$ and $R^{49}$ are each independently selected from the group consisting of hydrogen, $C_1$-$C_6$alkyl, tetrahydropyrane, cyclohexyl and cyclopentyl, wherein said $C_1$-$C_6$alkyl, tetrahydropyrane, cyclohexyl and cyclopentyl are optionally substituted with one or two substituents independently selected from the group consisting of halogen and hydroxy; or $R^{48}$ and $R^{49}$ together with the nitrogen to which they are attached form a 4 to 6 membered ring, wherein said 4 to 6 membered ring optionally is substituted with one or two substituents independently selected from the group consisting of hydroxy and halogen;

$R^{58}$ are each independently selected from the group consisting of halogen, —CN, hydroxy, oxo, —C(=O)OH, —S(=O)$_2R^{59}$, —S—$NR^{60}R^{61}$, S(=O)$_2NR^{60}R^{61}$, cyclopropyl, —$OR^{59}$, —$SR^{59}$, $C_1$-$C_6$alkyl, —C(=O)$NR^{60}R^{61}$, —$NR^{60}C(=O)NR^{61}R^{60}$, —$NR^{60}S(=O)_2R^{59}$ and —NC(=O)$R^{59}$;

$R^{59}$ is selected from the group consisting of hydrogen, $C_1$-$C_6$alkyl, $C_3$-$C_{10}$cycloalkyl, aryl and heteroaryl, wherein said $C_1$-$C_6$alkyl, $C_3$-$C_{10}$cycloalkyl, aryl and heteroaryl are optionally substituted with one, two or three substituents independently selected from the group consisting of halogen, methyl, ethyl, methoxy, ethoxy, trifluoromethyl, —CN and hydroxy;

$R^{60}$ and $R^{61}$ are each independently selected from the group consisting of hydrogen, $C_1$-$C_6$alkyl, $C_3$-$C_{10}$heterocyclyl, $C_3$-$C_{10}$cycloalkyl and heteroaryl, wherein said $C_1$-$C_6$alkyl, $C_3$-$C_{10}$heterocyclyl, $C_3$-$C_{10}$cycloalkyl and heteroaryl are optionally substituted with one or two substituents independently selected from the group consisting of halogen and hydroxy; or $R^{60}$ and $R^{61}$ together with the nitrogen to which they are attached form a 4 to 6 membered ring, wherein said 4 to 6 membered ring optionally is substituted with one or two substituents independently selected from the group consisting of hydroxy and halogen;

$R^{103}$ is selected from the group consisting of $C_3$-$C_{10}$heterocyclyl substituted with two substituents independently selected from the group consisting of $R^{62}$ and $R^{63}$, $C_3$-$C_{10}$cycloalkyl substituted with $R^{30}$ and $R^{31}$, aryl substituted with $R^{30}$ and $R^{31}$, heteroaryl substituted with two substituents independently selected from the group consisting of $R^{62}$ and $R^{63}$, —C(=O)$R^{93}$, —CH(OH)—$R^{33}$, —C(=O)—NR$^{94}$R$^{95}$, —NR$^{36}$C(=O)R$^{37}$, —OR$^{35}$, —SR$^{35}$, —S(=O)$_2$R$^{39}$, —S(=O)$_2$NR$^{34}$R$^{35}$, —NR$^{34}$S(=O)$_2$—R$^{40}$, —NR$^{24}$R$^{25}$—, —NR$^{34}$C(=O)—NR$^{34}$R$^{35}$, —C=C substituted with $R^{41}$ and $R^{42}$, W and —C≡C substituted with $R^{43}$;

W is selected from the group consisting of pyrrolidinone, tetrahydropyrane, 1,4-dioxane, aziridinone, azetidinone, piperidinone, thiazole, imidazole, tetrahydrofurane and oxepane;

$R^{93}$ is selected from the group consisting of hydrogen, $C_3$-$C_{10}$heterocyclyl, $C_3$-$C_{10}$cycloalkyl, aryl and heteroaryl, wherein said $C_3$-$C_{10}$heterocyclyl, $C_3$-$C_{10}$cycloalkyl, aryl and heteroaryl are optionally substituted with one, two or three independently selected $R^{58}$;

$R^{94}$ and $R^{95}$ are each independently selected from the group consisting of hydrogen, $C_3$-$C_{10}$cycloalkyl and heteroaryl, wherein said $C_3$-$C_{10}$cycloalkyl and heteroaryl are optionally substituted with one, two or three substituents independently selected from the group consisting of halogen, methyl, ethyl and hydroxy; or $R^{94}$ and $R^{95}$ together with the nitrogen to which they are attached form a 4 to 6 membered ring, wherein said 4 to 6 membered ring optionally is substituted with one or two substituents independently selected from the group consisting of hydroxy or halogen;

$R^{62}$ is selected from the group consisting of halogen, $C_1$-$C_6$alkyl, —C(=O)OH, —CH(OH)—$R^{47}$, —C(=O)—NR$^{48}$R$^{49}$, —NR$^{48}$C(=O)R$^{46}$, —SR$^{49}$, —S(=O)$_2$R$^{50}$, —S(=O)$_2$NR$^{48}$R$^{49}$, —NR$^{48}$S(=O)$_2$R$^{50}$, —NR$^{48}$C(=O)—NR$^{48}$R$^{49}$, —C=C—R$^{51}$R$^{52}$, —C≡C—R$^{53}$, CH$_2$CH$_2$OH, —CH$_2$CH$_2$OH, $C_3$-$C_{10}$heterocyclyl substituted with $R^{54}$, $C_3$-$C_{10}$cycloalkyl substituted with $R^{55}$, aryl substituted with $R^{56}$ and $R^{57}$ and heteroaryl substituted with $R^{56}$ and $R^{57}$;

$R^{63}$ is selected from the group consisting of hydrogen, =O, halogen, hydroxy, trifluoromethyl, —CN, oxo, —C(=O)OH, —S(=O)$_2$R$^{59}$, —S(=O)NR$^{60}$R$^{61}$, —S(=O)NR$^{60}$R$^{61}$ cyclopropyl, —OR$^{59}$, —SR$^{59}$, —C$_1$-C$_6$alkyl, —C(=O)NR$^{60}$R$^{61}$, —NR$^{60}$C(=O)NR$^{61}$R$^{60}$; —NR$^{60}$S(=O)$_2$R$^{59}$, and —N(C=O)R$^{59}$;

a salt thereof with a pharmaceutically acceptable acid or base, or any optical isomer or mixture of optical isomers, including a racemic mixture, or any tautomeric forms.

The following aspects refer to compounds that fall within the scope of Formula I:

In one aspect, Y is —X$^1$—X$^2$—X$^3$—R$^3$.

In one aspect, X$^1$ is selected from the group consisting of —S— and —S(=O)$_2$—.

In one aspect, X$^1$ is —S(=O)$_2$—.

In one aspect, X$^2$ is absent or is selected from the group consisting of —CR$^{44}$R$^{45}$— and —NR$^{25}$—.

In one aspect, X$^2$ is absent or is —CR$^{44}$R$^{45}$.

In one aspect, X$^3$ is absent or is —CR$^{70}$R$^{71}$—.

In one aspect, —X$^1$—X$^2$—X$^3$—R$^3$ is selected from the group consisting of —S—R$^3$, —S(=O)$_2$—R$^3$, —S(=O)$_2$—NR$^{25}$R$^3$, —S(=O)$_2$—CR$^{44}$R$^{45}$—R$^3$.

In one aspect, —X$^1$—X$^2$—X$^3$—R$^3$ is selected from the group consisting of —S—R$^3$, —S(=O)$_2$—R$^3$.

In one aspect, —X$^1$—X$^2$—X$^3$—R$^3$ is selected from the group consisting of —S(=O)$_2$—NR$^{25}$R$^3$, —S(=O)$_2$—CR$^{44}$R$^{45}$—R$^3$.

In one aspect, Y is selected from the group consisting of —CR$^{72}$R$^{73}$—O—CR$^{70}$R$^{71}$—R$^3$, —CR$^{72}$R$^{73}$—S—CR$^{70}$R$^{71}$—R$^3$, —CR$^{72}$R$^{73}$—S(=O)$_2$—CR$^{70}$R$^{71}$—R$^3$, —CR$^{72}$R$^{73}$—NR$^{25}$—S(=O)$_2$—R$^3$, —CR$^{72}$R$^{73}$—CR$^{70}$R$^{71}$—S(=O)$_2$—R$^3$, —CR$^{72}$R$^{73}$—CR$^{70}$R$^{71}$—O—R$^3$, —CR$^{72}$R$^{73}$—CR$^{70}$R$^{71}$—S—R$^3$, —CR$^{72}$R$^{73}$—CR$^{70}$R$^{71}$—NR$^{25}$—R$^3$, —O—CR$^{44}$R$^{45}$—S(=O)$_2$—R$^3$, —CR$^{72}$R$^{73}$—O—R$^3$, —CR$^{72}$R$^{73}$—S—R$^3$, —CR$^{72}$R$^{73}$—S(=O)$_2$—R$^3$, —CR$^{72}$R$^{73}$—NR$^{25}$—R$^3$, —CR$^{72}$R$^{73}$—S(=O)$_2$—R$^3$, —O—R$^{103}$, —O—CR$^{44}$R$^{45}$, —O—CR$^{44}$R$^{45}$—R$^{103}$, —R$^{72}$R$^{73}$—CR$^{44}$R$^{45}$—R$^{103}$, —O—CR$^{44}$R$^{45}$—CR$^{70}$R$^{71}$—R$^{103}$, —CR$^{72}$R$^{73}$—CR$^{44}$R$^{45}$—CR$^{70}$R$^{71}$—R$^{103}$, and —CR$^{72}$R$^{73}$—R$^{103}$.

In one aspect, Y is selected from the group consisting of —CR$^{72}$R$^{73}$—O—CR$^{70}$R$^{71}$—R$^3$, —CR$^{72}$R$^{73}$—S—CR$^{70}$R$^{71}$—R$^3$, —CR$^{72}$R$^{73}$—S(=O)$_2$—CR$^{70}$R$^{71}$—R$^3$, —CR$^{72}$R$^{73}$—NR$^{25}$—S(=O)$_2$—R$^3$, —CR$^{72}$R$^{73}$—CR$^{70}$R$^{71}$—S(=O)$_2$—R$^3$, —CR$^{72}$R$^{73}$—CR$^{70}$R$^{71}$—O—R$^3$ and —CR$^{72}$R$^{73}$—CR$^{70}$R$^{71}$—NR$^{25}$—R$^3$.

In one aspect, Y is selected from the group consisting of —CR$^{72}$R$^{73}$—O—CR$^{70}$R$^{71}$—R$^3$, —CR$^{72}$R$^{73}$—S—CR$^{70}$R$^{71}$—R$^3$, —CR$^{72}$R$^{73}$—CR$^{70}$R$^{71}$—O—R$^3$ and —CR$^{72}$R$^{73}$—CR$^{70}$R$^{71}$—NR$^{25}$—R$^3$.

In one aspect, Y is selected from the group consisting of —CR$^{72}$R$^{73}$—S(=O)$_2$—CR$^{70}$R$^{71}$—R$^3$, —CR$^{72}$R$^{73}$—CR$^{70}$R$^{71}$—S(=O)$_2$—R$^3$ and —CR$^{72}$R$^{73}$—NR$^{25}$—S(=O)$_2$—R$^3$.

In one aspect, Y is selected from the group consisting of —CR$^{72}$R$^{73}$—O—CR$^{70}$R$^{71}$—R$^3$, —CR$^{72}$R$^{73}$—CR$^{70}$R$^{71}$—O—R$^3$ and —CR$^{72}$R$^{73}$—CR$^{70}$R$^{71}$—NR$^{25}$—R$^3$.

In one aspect, Y is selected from the group consisting of $C_3$-$C_{10}$cycloalkyl substituted with $R^{19}$ and phenyl substituted with $R^{22}$.

In one aspect, Y is $C_3$-$C_{10}$cycloalkyl substituted with $R^{19}$.

In one aspect, Y is phenyl substituted with $R^{22}$.

In one aspect, R$^3$ is selected from the group consisting of $C_3$-$C_{10}$heterocyclyl substituted with $R^{30}$ and $R^{31}$, $C_3$-$C_{10}$cycloalkyl substituted with $R^{90}$ and $R^{91}$, aryl substituted with $R^{30}$ and $R^{31}$, heteroaryl substituted with $R^{90}$ and $R^{91}$.

In one aspect, R$^3$ is selected from the group consisting of —C(=O)R$^{32}$, —CH(OH)—R$^{33}$, —(CR$^{44}$R$^{45}$)$_n$—C(=O)—NR$^{34}$R$^{35}$, —(CR$^{44}$R$^{45}$)$_n$—NR$^{36}$C(=O)R$^{37}$, —(CR$^{44}$R$^{45}$)$_n$—OR$^{38}$, —(CR$^{44}$R$^{45}$)$_n$—SR$^{38}$, —(CR$^{44}$R$^{45}$)$_n$—S(=O)$_2$R$^{39}$, —(CR$^{44}$R$^{45}$)$_n$—S(=O)$_2$NR$^{34}$R$^{35}$, —(CR$^{44}$R$^{45}$)$_n$—NR$^{34}$S(=O)$_2$NR$^{40}$, —(CR$^{44}$R$^{45}$)$_n$—NR$^{34}$R$^{35}$, —(CR$^{44}$R$^{45}$)$_n$—NR$^{34}$C(=O)—NR$^{34}$R$^{35}$, —(CR$^{44}$R$^{45}$)$_n$—C=C—R$^{41}$R$^{42}$ and —(CR$^{44}$R$^{45}$)$_n$—C≡C—R$^{43}$.

In one aspect, R$^3$ is selected from the group consisting of $C_3$-$C_{10}$heterocyclyl substituted with $R^{30}$, $C_3$-$C_{10}$cycloalkyl substituted with $R^{90}$, aryl substituted with $R^{30}$, heteroaryl substituted with $R^{90}$, —(CR$^{44}$R$^{45}$)C(=O)—NR$^{34}$R$^{35}$, —(CR$^{44}$R$^{45}$)$_n$—NR$^{38}$C(=O)R$^{37}$, —(CR$^{44}$R$^{45}$)OR$^{38}$, —(CR$^{44}$—R$^{45}$)$_n$—S(=O)$_2$R$^{39}$, —(CR$^{44}$R$^{45}$)$_n$—S(=O)$_2$NR$^{34}$R$^{35}$, —(CR$^{44}$R$^{45}$)$_n$—NR$^{34}$S(=O)$_2$—R$^{40}$, —(CR$^{44}$R$^{45}$)$_n$—NR$^{34}$C(=O)—NR$^{34}$R$^{35}$, —(CR$^{44}$R$^{45}$)$_n$—C=CR$^{41}$R$^{42}$ and —(CR$^{44}$R$^{45}$)$_n$—C≡C—R$^{43}$.

In one aspect, $R^3$ is selected from the group consisting of $C_3$-$C_{10}$heterocyclyl substituted with $R^{30}$, $C_3$-$C_{10}$cycloalkyl substituted with $R^{90}$, aryl substituted with $R^{30}$; heteroaryl substituted with $R^{90}$, —C(=O)—NR$^{34}$R$^{35}$, —NR$^{36}$C(=O)R$^{37}$, —OR$^{38}$, —S(=O)$_2$R$^{39}$, —S(=O)$_2$NR$^{34}$R$^{35}$, —NR$^{34}$S(=O)$_2$—R$^{40}$, —NR$^{34}$C(=O)—NR$^{34}$R$^{35}$, —C=CR$^{41}$R$^{42}$ and —C≡C—R$^{43}$.

In one aspect, $R^3$ is selected from the group consisting of $C_3$-$C_{10}$heterocyclyl substituted with $R^{30}$, $C_3$-$C_{10}$cycloalkyl substituted with $R^{90}$, heteroaryl substituted with $R^{30}$, —C(=O)—NR$^{34}$R$^{35}$, —NR$^{36}$C(=O)R$^{37}$, —OR$^{38}$, —S(=O)$_2$R$^{39}$, —S(=O)$_2$NR$^{34}$R$^{35}$, —NR$^{34}$S(=O)$_2$—R$^{40}$, —NR$^{34}$C(=O)—NR$^{34}$R$^{35}$, —C=CR$^{41}$R$^{42}$ and —C≡C—R$^{43}$.

In one aspect, $R^3$ is selected from the group consisting of piperidine substituted with $R^{30}$, pyrrolidine substituted with $R^{30}$, morpholine substituted with $R^{30}$, tetrahydropyranyl substituted with $R^{30}$, cyclohexyl substituted with $R^{30}$, cyclopropyl substituted with $R^{30}$, cyclobutyl substituted with $R^{30}$, cyclopentyl substituted with $R^{30}$, phenyl substituted with $R^{30}$; pyridazinyl substituted with $R^{30}$, pyrazinyl substituted with $R^{30}$, pyridine substituted with $R^{30}$, imidazolyl substituted with $R^{30}$, pyrazolyl substituted with $R^{30}$ and pyrimidinyl substituted with $R^{30}$, isoxazolyl substituted with $R^{30}$, pyridinyl substituted with $R^{30}$, —C(=O)—NR$^{34}$R$^{35}$, —NR$^{36}$C(=O)R$^{37}$, —OR$^{38}$, —S(=O)$_2$R$^{39}$, —S(=O)$_2$NR$^{34}$R$^{35}$, —NR$^{34}$S(=O)$_2$—R$^{40}$, —NR$^{34}$C(=O)—NR$^{34}$R$^{35}$ and —C≡C—R$^{43}$.

In one aspect, $R^3$ is selected from the group consisting of piperidine substituted with $R^{30}$, pyrrolidine substituted with $R^{30}$, morpholine substituted with $R^{30}$, tetrahydropyranyl substituted with $R^{30}$, cyclohexyl substituted with $R^{30}$, cyclopropyl substituted with $R^{30}$, cyclobutyl substituted with $R^{30}$, cyclopentyl substituted with $R^{30}$, phenyl substituted with $R^{30}$; pyridazinyl substituted with $R^{30}$, pyrazinyl substituted with $R^{30}$, pyridine substituted with $R^{30}$, imidazolyl substituted with $R^{30}$, pyrazolyl substituted with $R^{30}$ and pyrimidinyl substituted with $R^{30}$, isoxazolyl substituted with $R^{30}$, pyridinyl substituted with $R^{30}$.

In one aspect, $R^3$ is selected from the group consisting of —NR$^{36}$C(=O)R$^{37}$, —NR$^{34}$S(=O)$_2$—R$^{40}$ and —NR$^{34}$C(=O)—NR$^{34}$R$^{35}$.

In one aspect, $R^3$ is selected from the group consisting of —C(=O)—NR$^{34}$R$^{35}$, —OR$^{38}$, —S(=O)$_2$R$^{39}$, —S(=O)$_2$NR$^{34}$R$^{38}$ and —C≡C—R$^{43}$.

In one aspect, n is selected from the group consisting of 0 or 1.

In one aspect, n is 0.

In one aspect, $R^{103}$ is selected from the group consisting of —C(=O)R$^{93}$, —CH(OH)—R$^{33}$, —C(=O)—NR$^{94}$R$^{98}$, —NR$^{36}$C(=O)R$^{37}$, —OR$^{38}$, —SR$^{38}$, —S(=O)$_2$R$^{39}$, —S(=O)$_2$NR$^{34}$R$^{35}$, —NR$^{34}$S(=O)$_2$—R$^{40}$, —NR$^{24}$R$^{25}$—, —NR$^{34}$C(=O)—NR$^{34}$R$^{35}$, —C=C substituted with R$^{41}$ and R$^{42}$, W and —C≡C substituted with R$^{43}$.

In one aspect, $R^{103}$ is selected from the group consisting of $C_3$-$C_{10}$heterocyclyl substituted with two substitutions independently selected from the group consisting of R$^{62}$ and R$^{63}$, $C_3$-$C_{10}$cycloalkyl substituted with R$^{30}$ and R$^{31}$, aryl substituted with R$^{30}$ and R$^{31}$, heteroaryl substituted with two substitutions independently selected from the group consisting of R$^{62}$ and R$^{63}$.

In one aspect, $R^{103}$ is selected from the group consisting of $C_3$-$C_{10}$heterocyclyl substituted with one or two substitutions independently selected from the group consisting of R$^{62}$ and R$^{63}$ and heteroaryl substituted with two substitutions independently selected from the group consisting of R$^{62}$ and R$^{63}$.

In one aspect, $R^{103}$ is selected from the group consisting of cyclopropyl, cyclobutyl, cyclohexyl and cyclopentyl substituted with R$^{30}$ and R$^{31}$ and phenyl substituted with R$^{30}$ and R$^{31}$, tetrahydropyranyl, piperidinyl, pyrrolidinyl and morpholinyl substituted with two substitutions independently selected from the group consisting of R$^{62}$ and R$^{63}$ and imidazolyl, pyrazolyl, isoxazolyl, pyridazinyl, pyrazinyl pyrimidinyl and pyridinyl substituted with two substitutions independently selected from the group consisting of R$^{62}$ and R$^{63}$.

In one aspect, $R^{103}$ is selected from the group consisting of tetrahydropyranyl, piperidinyl, pyrrolidinyl and morpholinyl substituted with two substitutions independently selected from the group consisting of R$^{62}$ and R$^{63}$ and imidazolyl, pyrazolyl, isoxazolyl, pyridazinyl, pyrazinyl pyrimidinyl and pyridinyl substituted with two substitutions independently selected from the group consisting of R$^{62}$ and R$^{63}$.

In one aspect, $R^{103}$ comprises at least one R$^{62}$ group.

In one aspect, $R^{103}$ is selected from the group consisting of $C_3$-$C_{10}$cycloalkyl substituted with R$^{30}$ and R$^{31}$ and aryl substituted with R$^{30}$ and R$^{31}$;

In one aspect, $R^{103}$ is selected from the group consisting of cyclopropyl, cyclobutyl, cyclohexyl, phenyl and cyclopentyl substituted with R$^{30}$ and R$^{31}$;

In one aspect, $R^{103}$ is selected from the group consisting of —C(=O)—NR$^{94}$R$^{95}$, —NR$^{36}$C(=O)R$^{37}$, —OR$^{38}$, —SR$^{38}$, —S(=O)$_2$R$^{39}$, —S(=O)$_2$NR$^{34}$R$^{35}$, —NR$^{34}$S(=O)$_2$—R$^{40}$, —NR$^{34}$C(=O)—NR$^{34}$R$^{35}$, W and —C≡C substituted with R$^{43}$.

In one aspect, $R^{103}$ is selected from the group consisting of —C(=O)—NR$^{94}$R$^{95}$, —NR$^{36}$C(=O)R$^{37}$, —OR$^{38}$, —S(=O)$_2$R$^{39}$, —S(=O)$_2$NR$^{34}$R$^{35}$, —NR$^{34}$S(=O)$_2$—R$^{40}$, —NR$^{34}$C(=O)—NR$^{34}$R$^{35}$ and W.

In one aspect, $R^{103}$ is selected from the group consisting of —NR$^{36}$C(=O)R$^{37}$, —NR$^{34}$S(=O)$_2$—R$^{40}$ and —NR$^{34}$C(=O)—NR$^{34}$R$^{35}$.

In one aspect, $R^{103}$ is selected from the group consisting of —C(=O)—NR$^{94}$R$^{95}$, —OR$^{38}$, —S(=O)$_2$R$^{39}$, —S(=O)$_2$NR$^{34}$R$^{35}$ and W.

In one aspect, $R^{103}$ is W selected from the group consisting of pyrrolidinone, tetrahydropyrane, 1,4-dioxane, piperidinone, thiazole, imidazole and tetrahydrofurane.

In one aspect, $R^{103}$ is W selected from the group consisting of pyrrolidinone, tetrahydropyrane, piperidinone and imidazole.

In one aspect, $R^1$ is selected from the group consisting of hydrogen, methyl, ethyl, isopropyl and cyclopropyl and $R^2$ is selected from the group consisting of a monovalent radical having one of the following formulae, wherein the symbol * denotes the point of attachment:

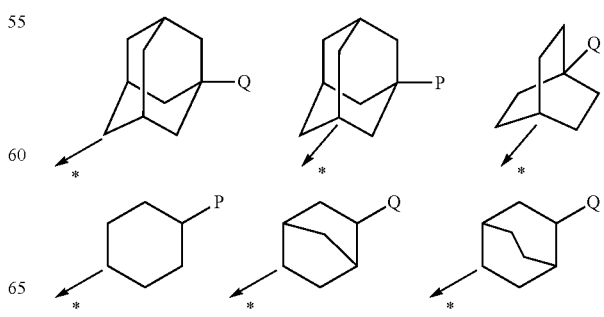

-continued
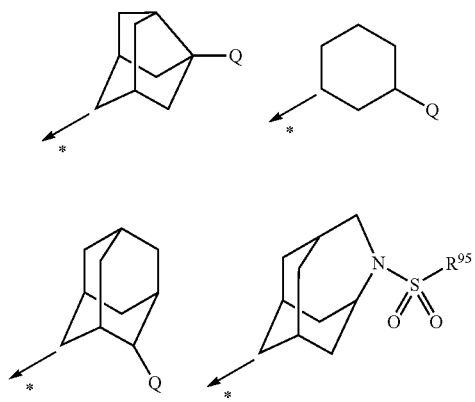
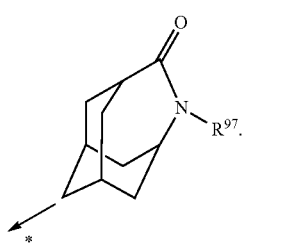
In one aspect, $R^1$ is selected from the group consisting of hydrogen and methyl.
In one aspect, $R^1$ is hydrogen.
In one aspect, $R^1$ is methyl.
In one aspect, $R^2$ is selected from the group consisting of:
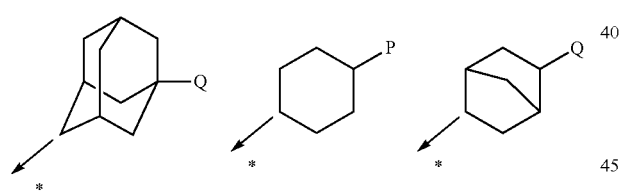
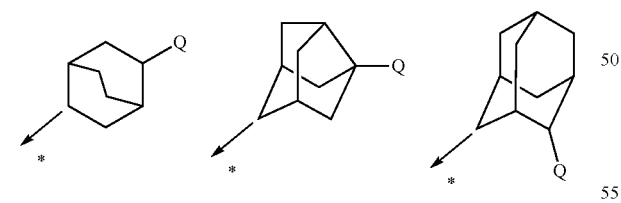
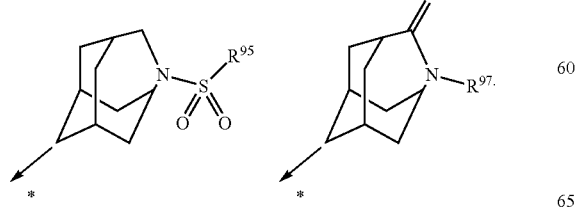
In one aspect, $R^2$ is selected from the group consisting of:
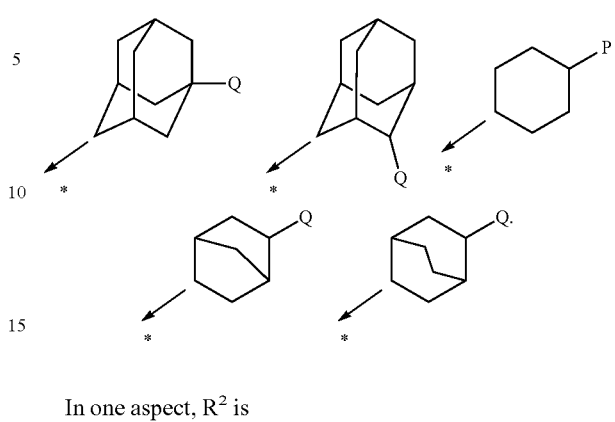
In one aspect, $R^2$ is
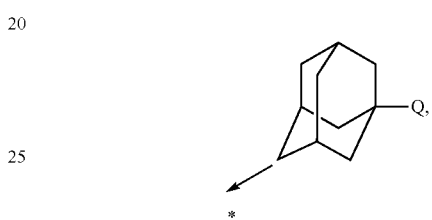
In one aspect, $R^2$ is
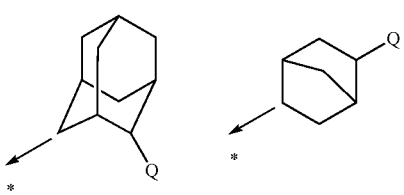
In one aspect, $R^2$ is
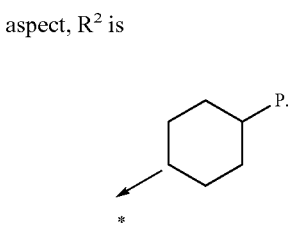
In one aspect, $R^2$ is
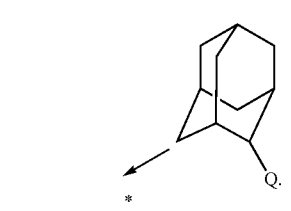

In one aspect, $R^2$ is

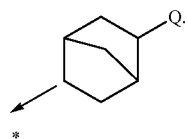

In one aspect, $R^2$ is

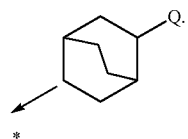

In one aspect, $R^1$ and $R^2$ together with the nitrogen to which they are attached is selected from the group consisting of:

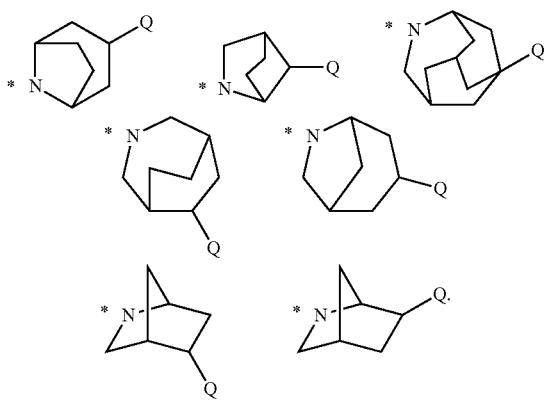

In one aspect, $R^1$ and $R^2$ together with the nitrogen to which they are attached is

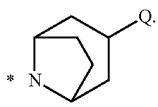

In one aspect, Q is a hydroxyl group.
In one aspect, Q is a carboxy group.
In one aspect, Q is a —S(=O)$_2$R$^6$ group.
In one aspect, Q is selected is a —S(=O)$_2$NH$_2$ group.
In one aspect, P is a —S(=O)$_2$R$^6$ group.
In one aspect, P is a carboxy group.
In one aspect, P is a —S(=O)$_2$NH$_2$ group.
In one aspect, $R^6$ is selected from the group consisting of methyl, isopropyl, ethyl, phenyl, pyridine, cyclopropyl, cyclobutyl, cyclohexyl and cyclopentyl, wherein said methyl, isopropyl, ethyl, phenyl, pyridine, cyclopropyl, cyclobutyl, cyclohexyl and cyclopentyl are optionally substituted with one or two independently selected $R^7$.
In one aspect, $R^6$ is selected from the group consisting of methyl, ethyl, isopropyl, phenyl, pyridine, cyclopropyl and cyclohexyl, wherein said methyl, isopropyl, phenyl, pyridine, cyclopropyl and cyclohexyl are optionally substituted with $R^7$.

In one aspect, $R^7$ is selected from the group consisting of hydrogen, methyl, cyclopropyl, —O—CH$_3$, —O-cyclopropyl, —O-isopropyl, hydroxy, fluoride and chloride, wherein said methyl, ethyl, cyclopropyl, —O—CH$_3$, —O-isopropyl and —O-cyclopropyl is optionally substituted with one substituent selected from the group consisting of hydroxy and halogen.

In one aspect, $R^7$ is selected from the group consisting of hydrogen, methyl, cyclopropyl, —O-cyclopropyl, —O-isopropyl, hydroxy, fluoride and chloride, wherein said ethyl, cyclopropyl and —O-cyclopropyl is optionally substituted with one substituent selected from the group consisting of hydroxy and halogen.

In one aspect, $R^4$ is selected from the group consisting of hydrogen, methyl, isopropyl, ethyl, —O-methyl, —O-isopropyl, —O-ethyl, wherein said, methyl, isopropyl, ethyl, —O-methyl, —O-isopropyl, —O-ethyl are substituted with $R^{12}$ and $R^{13}$, trifluoromethyl, CN, fluorine, chlorine, —S(=O)$_2$methyl, —S(=O)$_2$ethyl, —S(=O)$_2$cyclopropyl, —S(=O)$_2$NHR$^{11}$ and —C(=O)NHR$^{10}$.

In one aspect, $R^4$ is selected from the group consisting of hydrogen, methyl, isopropyl, ethyl, —O-methyl, —O-isopropyl, —O-ethyl, wherein said, methyl, isopropyl, ethyl, —O-methyl, —O-isopropyl, —O-ethyl are substituted with $R^{12}$, trifluoromethyl, fluorine, chlorine, —S(=O)$_2$(methyl)$_2$, —S(=O)$_2$methyl, —S(=O)$_2$ethyl, —S(=O)$_2$cyclopropyl, —S(=O)$_2$Nmethyl, —S(=O)$_2$Nisopropyl, —C(=O)Nisopropyl, —C(=O)N(methyl)$_2$ and —C(=O)Nmethyl.

In one aspect, $R^4$ is selected from the group consisting of hydrogen, methyl, isopropyl, —O-methyl, —O-isopropyl, —O-ethyl, trifluoromethyl, fluorine, chlorine, —S(=O)$_2$methyl, —S(=O)$_2$-ethyl, —S(=O)$_2$cyclopropyl, —S(=O)$_2$Nmethyl, —S(=O)$_2$Nisopropyl, —C(=O)Nisopropyl and —C(=O)Nmethyl.

In one aspect, $R^4$ is in the ortho position.
In one aspect, $R^4$ is in the meta position.

In one aspect, $R^{95}$ is selected from the group consisting of methyl, isopropyl, ethyl, phenyl, pyridine, pyrimidine, cyclopropyl, cyclobutyl and cyclohexyl, wherein said ethyl, phenyl, pyridine, pyrimidine, cyclopropyl, cyclobutyl and cyclohexyl are optionally substituted with one or two independently selected $R^{96}$.

In one aspect, $R^{95}$ is selected from the group consisting of methyl, isopropyl, phenyl, pyridine, pyrimidine, cyclopropyl and cyclohexyl, wherein said ethyl, phenyl, pyridine, pyrimidine, cyclopropyl and cyclohexyl are optionally substituted with one $R^{96}$.

In one aspect, $R^{96}$ is selected from the group consisting of fluorine, chlorine, hydroxy, oxo, trifluoromethyl, methyl, isopropyl, ethyl and —S(=O)$_2$methyl.

In one aspect, $R^{96}$ is selected from the group consisting of fluorine, chlorine, hydroxy, trifluoromethyl, methyl, isopropyl and —S(=O)$_2$methyl.

In one aspect, $R^{97}$ is selected from the group consisting of hydrogen, methyl, isopropyl and ethyl.

In one aspect, $R^{97}$ is selected from the group consisting of hydrogen, methyl and isopropyl.

In one aspect, $R^{12}$ is selected from the group consisting of hydrogen, —O-(methyl, isopropyl, ethyl), fluorine, chlorine, carboxy and hydroxy.

In one aspect, $R^{12}$ is selected from the group consisting of hydrogen, —O-methyl, —O-isopropyl, fluorine and hydroxy.

In one aspect, $R^{13}$ is selected from the group consisting of hydrogen, —O-(methyl, isopropyl, ethyl), fluorine, chlorine, carboxy and hydroxy.

In one aspect, $R^{13}$ is selected from the group consisting of hydrogen, —O-methyl, —O-isopropyl, fluorine and hydroxy.

In one aspect, $R^5$ is selected from the group consisting of hydrogen, methyl, isopropyl, ethyl, trifluoromethyl, CN, fluorine, chlorine, acetyl, ethy, carbonyl, —S(=O)$_2$R$^{17}$, S(=O)$_2$NR$^{14}$R$^{15}$, S-methyl, S-isopropyl, and S-ethyl; wherein said methyl, isopropyl, ethyl are substituted with $R^{16}$ and; wherein said ethyl and carbonyl are substituted with $R^{18}$.

In one aspect, $R^5$ is selected from the group consisting of hydrogen, methyl, isopropyl, ethyl, trifluoromethyl, fluorine, chlorine, acetyl, —S(=O)$_2$methyl, —S(=O)$_2$ isopropyl, S(=O)$_2$NH$_2$, S(=O)$_2$N(CH$_3$)$_2$, S-methyl, S-isopropyl, and S-ethyl; wherein said methyl, isopropyl, and ethyl are optionally substituted with fluorine or hydroxyl.

In one aspect, $R^5$ is selected from the group consisting of hydrogen, methyl, isopropyl, trifluoromethyl, fluorine, chlorine, acetyl, —S(=O)$_2$methyl and —S(=O)$_2$ isopropyl.

In one aspect, $R^{10}$ and $R^{11}$ are each independently selected from the group consisting of hydrogen, and $C_1$-$C_4$alkyl.

In one aspect, $R^{10}$ and $R^{11}$ are each independently selected from the group consisting of hydrogen, methyl, ethyl and isopropyl.

In one aspect, $R^{10}$ and $R^{11}$ together with the nitrogen to which they are attached form a piperidinyl, pyrrolidinyl and morpholinyl ring, wherein said ring optionally is substituted with one or two substituents independently selected from the group consisting of hydroxy and fluoride.

In one aspect, $R^{10}$ and $R^{11}$ together with the nitrogen to which they are attached form a piperidinyl, ring, wherein said ring optionally is substituted with one or two substituents independently selected from the group consisting of hydroxy and fluoride.

In one aspect, $R^{14}$ and $R^{15}$ are each independently selected from the group consisting of hydrogen, and $C_1$-$C_4$alkyl.

In one aspect, $R^{14}$ and $R^{15}$ are each independently selected from the group consisting of hydrogen, methyl, ethyl and isopropyl.

In one aspect, $R^{14}$ and $R^{15}$ together with the nitrogen to which they are attached form a piperidinyl, pyrrolidinyl and morpholinyl ring wherein said ring optionally is substituted with one or two substituents independently selected from the group consisting of hydroxy and fluoride.

In one aspect, $R^{14}$ and $R^{15}$ together with the nitrogen to which they are attached form a piperidinyl ring, wherein said ring optionally is substituted with one or two substituents independently selected from the group consisting of hydroxy and fluoride In one aspect, $R^{16}$ is selected from the group consisting of hydrogen —O-methyl, methyl, cyclopropyl, fluorine, chlorine, —S(=O)$_2$-methyl, —S(=O)$_2$-ethyl, —C(=O)NH$_2$, —C(=O)N—CH$_3$CH$_3$, carboxy, and hydroxy.

In one aspect, $R^{16}$ is selected from the group consisting of hydrogen, methyl, cyclopropyl, fluorine, —S(=O)$_2$-methyl, —C(=O)N—(CH$_3$)$_2$ and hydroxy.

In one aspect, $R^{18}$ is selected from the group consisting of hydrogen —O-methyl, methyl, cyclopropyl, fluorine, chlorine, —S(=O)$_2$-methyl, —S(=O)$_2$-ethyl, —C(=O)NH$_2$, —C(=O)N—CH$_3$CH$_3$, carboxy, and hydroxy.

In one aspect, $R^{18}$ is selected from the group consisting of hydrogen, methyl, cyclopropyl, fluoride, —S(=O)$_2$-methyl, —C(=O)N—(CH$_3$)$_2$ and hydroxy.

In one aspect, $R^{17}$ is selected from the group consisting of hydrogen, methyl, ethyl and isopropyl, wherein said ethyl and isopropyl is optionally substituted with one or two substituents selected from the group consisting of hydroxyl, fluorine and chlorine.

In one aspect, $R^{17}$ is selected from the group consisting of hydrogen, methyl, ethyl and isopropyl, wherein said ethyl is optionally substituted with one substituents selected from the group consisting of hydroxy and fluorine.

In one aspect, $R^{19}$ is selected from the group consisting of halogen, —CN, —C(=O)R$^{46}$, —CH(OH)—R$^{47}$, —(CR$^{44}$R$^{45}$)$_m$—C(=O)—NR$^{48}$R$^{49}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{59}$, —(CR$^{44}$R$^{45}$)$_m$—NR$^{48}$C(=O)—NR$^{48}$R$^{49}$, —(CR$^{44}$R$^{45}$)$_m$—C=C—R$^{51}$R$^{52}$, and —(CR$^{44}$R$^{45}$)$_m$—C≡C—R$^{53}$.

In one aspect, $R^{19}$ is selected from the group consisting of, —(CR$^{44}$R$^{45}$)$_m$—C$_3$-C$_{10}$cycloalkyl substituted with R$^{55}$, and —(CR$^{44}$R$^{45}$)$_m$-aryl substituted with R$^{56}$ and R$^{57}$.

In one aspect, $R^{19}$ is selected from the group consisting of —CN, —(CR$^{44}$R$^{45}$)$_m$—C(=O)—NR$^{48}$R$^{49}$, —(CR$^{44}$R$^{45}$)$_m$—OR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{59}$, —(CR$^{44}$R$^{45}$)$_m$—NR$^{48}$C(=O)—NR$^{48}$R$^{49}$.

In one aspect, $R^{19}$ is selected from the group consisting of, —C$_3$-C$_{10}$cycloalkyl substituted with R$^{55}$, and -phenyl substituted with R$^{56}$.

In one aspect, $R^{19}$ is selected from the group consisting of —CN, —C(=O)—NR$^{48}$R$^{49}$, —NR$^{48}$C(=O)R$^{46}$, —OR$^{49}$, —S(=O)$_2$R$^{50}$, —S(=O)$_2$NR$^{48}$R$^{49}$, —NR$^{48}$S(=O)$_2$R$^{50}$, —NR$^{48}$C(=O)—NR$^{48}$R$^{49}$.

In one aspect, $R^{22}$ is selected from the group consisting of halogen, —CN, hydroxy, —C(=O)OH, —C(=O)R$^{46}$, —CH(OH)—R$^{47}$, hydroxy, —(CR$^{44}$R$^{45}$)$_m$—C(=O)—NR$^{48}$R$^{49}$, —(CR$^{44}$R$^{45}$)$_m$—NR$^{48}$C(=O)R$^{46}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{50}$, —(CR$^{44}$R$^{45}$)$_m$—NR$^{48}$R$^{49}$, —(CR$^{44}$R$^{45}$)$_m$—NR$^{48}$C(=O)—NR$^{48}$R$^{49}$, —(CR$^{44}$—R$^{45}$)$_m$—C=C—R$^{51}$R$^{52}$, —(CR$^{44}$R$^{45}$)$_m$—C≡C—R$^{53}$.

In one aspect, $R^{22}$ is selected from the group consisting of —(CR$^{44}$R$^{45}$)$_m$—C$_3$-C$_{10}$heterocyclyl substituted with R$^{54}$, —(CR$^{44}$R$^{45}$)$_m$—C$_3$-C$_{10}$cycloalkyl substituted with R$^{55}$, —(CR$^{44}$R$^{45}$)$_m$-aryl substituted with R$^{56}$ and R$^{57}$ and —(CR$^{44}$R$^{45}$)$_m$-heteroaryl substituted with R$^{56}$ and R$^{57}$.

In one aspect, $R^{22}$ is selected from the group consisting of fluorine, chlorine, —CN, hydroxy, —C(=O)OH, —(CR$^{44}$R$^{45}$)$_m$—C(=O)—NR$^{48}$R$^{49}$, —(CR$^{44}$R$^{45}$)$_m$—NR$^{48}$C(=O)R$^{46}$, —(CR$^{44}$R$^{45}$)$_m$—OR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{50}$, —(CR$^{44}$—R$^{45}$)$_m$—NR$^{48}$C(=O)—NR$^{48}$R$^{49}$.

In one aspect, $R^{22}$ is selected from the group consisting of —C$_3$-C$_{10}$heterocyclyl substituted with R$^{54}$, —C$_3$-C$_{10}$cycloalkyl substituted with R$^{55}$, -phenyl substituted with R$^{56}$ and -heteroaryl substituted with R$^{58}$.

In one aspect, $R^{22}$ is selected from the group consisting of fluorine, chlorine, —CN, hydroxy, —C(=O)OH, —C(=O)—NR$^{48}$R$^{49}$, —NR$^{48}$C(=O)R$^{46}$, —OR$^{49}$, —S(=O)$_2$R$^{50}$, —S(=O)$_2$NR$^{48}$R$^{49}$, —NR$^{48}$S(=O)$_2$R$^{50}$, —NR$^{48}$C(=O)—NR$^{48}$R$^{49}$.

In one aspect, $R^{22}$ is selected from the group consisting of tetrahydropyranyl, piperidinyl, pyrrolidinyl and morpholinyl substituted with R$^{54}$, cyclopropyl, cyclobutyl, cyclohexyl and cyclopentyl substituted with R$^{55}$, -phenyl substituted with R$^{56}$ and imidazolyl, pyrazolyl, isoxazolyl, pyridazinyl, pyrazinyl pyrimidinyl and pyridinyl substituted with R$^{56}$.

In one aspect, $R^{22}$ is selected from the group consisting of tetrahydropyranyl, piperidinyl and morpholinyl substituted with R$^{54}$, cyclopropyl, cyclobutyl, cyclohexyl and cyclopentyl substituted with R$^{55}$, phenyl substituted with R$^{56}$ and pyridazinyl, pyrazinyl pyrimidinyl and pyridinyl substituted with R$^{56}$.

In one aspect, $R^{22}$ is selected from the group consisting of C≡C—$R^{51}R^{52}$, —C≡C—$R^{53}$ and —CH$_2$CH$_2$OH.

In one aspect, $R^{24}$ is selected from the group consisting of —C(=O)—$R^{26}$, —S(=O)$_2$—$R^{27}$, imidazolyl, pyrazolyl, isoxazolyl, pyridazinyl, pyrazinyl pyrimidinyl and pyridinyl substituted with $R^{28}$, and phenyl substituted with $R^{29}$.

In one aspect, $R^{24}$ is selected from the group consisting of —C(=O)—$R^{26}$, —S(=O)$_2$—$R^{27}$, pyridazinyl, pyrazinyl pyrimidinyl and pyridinyl substituted with $R^{28}$, and phenyl substituted with $R^{29}$.

In one aspect, $R^{25}$ is selected from the group consisting of hydrogen, methyl, ethyl, isopropyl and cyclopropyl.

In one aspect, $R^{25}$ is selected from the group consisting of hydrogen, methyl, isopropyl and cyclopropyl.

In one aspect, $R^{125}$ is selected from the group consisting of hydrogen, methyl, ethyl, isopropyl and cyclopropyl.

In one aspect, $R^{125}$ is selected from the group consisting of hydrogen, methyl, isopropyl and cyclopropyl.

In one aspect, $R^{44}$ and $R^{45}$ are each independently selected from the group consisting hydrogen, fluorine, chlorine, methyl, ethyl, isopropyl, cyclopropyl, cyclobutyl, cyclohexyl and cyclopentyl, wherein said ethyl, isopropyl, cyclopropyl, cyclobutyl, cyclohexyl and cyclopentyl are optionally substituted with one substituent selected independently from the group consisting of fluorine, chlorine, hydroxy and oxo.

In one aspect, $R^{44}$ and $R^{45}$ are each independently selected from the group consisting hydrogen, fluorine, chlorine, methyl, ethyl, isopropyl, cyclopropyl, cyclobutyl, cyclohexyl and cyclopentyl, wherein said ethyl, cyclopropyl, cyclobutyl, cyclohexyl and cyclopentyl are optionally substituted with one substituent selected independently from the group consisting of fluorine and hydroxyl.

In one aspect, $R^{44}$ and $R^{45}$ together with the carbon atom to which they are attached form a cyclopropyl ring, wherein said ring are optionally substituted with hydroxy or fluorine.

In one aspect, $R^{44}$ and $R^{45}$ together with the carbon atom to which they are attached form a cyclobutyl ring, wherein said ring are optionally substituted with hydroxy or fluorine.

In one aspect, $R^{79}$ and $R^{71}$ are each independently selected from the group consisting hydrogen, fluorine, chlorine, methyl, ethyl, isopropyl, cyclopropyl, cyclobutyl, cyclohexyl and cyclopentyl, wherein said ethyl, isopropyl, cyclopropyl, cyclobutyl, cyclohexyl and cyclopentyl are optionally substituted with one substituent selected independently from the group consisting of fluorine, chlorine, hydroxy and oxo.

In one aspect, $R^{70}$ and $R^{71}$ are each independently selected from the group consisting hydrogen, fluorine, chlorine, methyl, ethyl, isopropyl, cyclopropyl, cyclobutyl, cyclohexyl and cyclopentyl, wherein said ethyl, cyclopropyl, cyclobutyl, cyclohexyl and cyclopentyl are optionally substituted with one substituent selected independently from the group consisting of fluorine and hydroxyl.

In one aspect, $R^{70}$ and $R^{71}$ together with the carbon atom to which they are attached form a cyclopropyl ring, wherein said ring are optionally substituted with hydroxy or fluorine.

In one aspect, $R^{70}$ and $R^{71}$ together with the carbon atom to which they are attached form a cyclobutyl ring, wherein said ring are optionally substituted with hydroxy or fluorine.

In one aspect, $R^{72}$ and $R^{73}$ are each independently selected from the group consisting hydrogen, fluorine, chlorine, methyl, ethyl, isopropyl, cyclopropyl, cyclobutyl, cyclohexyl and cyclopentyl, wherein said ethyl, isopropyl, cyclopropyl, cyclobutyl, cyclohexyl and cyclopentyl are optionally substituted with one substituent selected independently from the group consisting of fluorine, chlorine, hydroxy and oxo.

In one aspect, $R^{72}$ and $R^{73}$ are each independently selected from the group consisting hydrogen, fluorine, chlorine, methyl, ethyl, isopropyl, cyclopropyl, cyclobutyl, cyclohexyl and cyclopentyl, wherein said ethyl, cyclopropyl, cyclobutyl, cyclohexyl and cyclopentyl are optionally substituted with one substituent selected independently from the group consisting of fluorine and hydroxyl.

In one aspect, $R^{72}$ and $R^{73}$ together with the carbon atom to which they are attached form a cyclopropyl ring, wherein said ring are optionally substituted with hydroxy or fluorine.

In one aspect, $R^{72}$ and $R^{73}$ together with the carbon atom to which they are attached form a cyclobutyl ring, wherein said ring are optionally substituted with hydroxy or fluorine.

In one aspect, $R^{30}$ and $R^{31}$ are each independently selected from the group consisting of hydrogen, halogen, CN, —C(=O)OH, —C(=O)$R^{46}$, —CH(OH)—$R^{47}$, hydroxy, —(CR$^{44}$R$^{45}$)$_m$—C(=O)—NR$^{48}$R$^{49}$, —(CR$^{44}$R$^{45}$)$_m$—NR$^{48}$C(=O)$R^{46}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{50}$, —(CR$^{44}$R$^{45}$)$_m$—NR$^{48}$R$^{49}$, —(CR$^{44}$R$^{45}$)$_m$—NR$^{48}$C(=O)—NR$^{48}$R$^{49}$, —(CR$^{44}$R$^{45}$)$_m$—C≡C—$R^{51}R^{52}$, and —(CR$^{44}$R$^{45}$)$_m$—C≡C—$R^{53}$. In one aspect, $R^{30}$ and $R^{31}$ are each independently selected from the group consisting of hydrogen, halogen, CN, —C(=O)OH, hydroxy, —(CR$^{44}$R$^{45}$)$_m$—C(=O)—NR$^{48}$R$^{49}$, —(CR$^{44}$R$^{45}$)$_m$—NR$^{48}$C(=O)R$^{46}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}$R$^{49}$, —(CR$^{44}$R$^{45}$)$_m$—NR$^{48}$S(=O)$_2$R$^{50}$, —(CR$^{44}$R$^{45}$)$_m$—NR$^{48}$C(=O)—NR$^{48}$R$^{49}$, and —(CR$^{44}$R$^{45}$)$_m$—C≡C—$R^{53}$.

In one aspect, $R^{30}$ ad $R^{31}$ are each independently selected from the group consisting of hydrogen, halogen, CN, —C(=O)OH, hydroxy, —C(=O)—NR$^{48}$R$^{49}$, —NR$^{48}$C(=O)R$^{46}$, —OR$^{49}$, —S(=O)$_2$R$^{50}$, —S(=O)$_2$NR$^{48}$R$^{49}$, —NR$^{48}$S(=O)$_2$R$^{50}$, —NR$^{48}$C(=O)—NR$^{48}$R$^{49}$ and —C≡C—$R^{53}$.

In one aspect, $R^{30}$ ad $R^{31}$ are each independently selected from the group consisting of hydrogen, halogen, CN, —C(=O)OH, hydroxy, —C(=O)—NR$^{48}$R$^{49}$, —S(=O)$_2$R$^{50}$ and —S(=O)$_2$NR$^{48}$R$^{49}$.

In one aspect, $R^{30}$ ad $R^{31}$ are each independently selected from the group consisting of hydrogen, halogen, CN, —C(=O)OH, hydroxy, —NR$^{48}$C(=O)R$^{46}$, —OR$^{49}$, —NR$^{48}$S(=O)$_2$R$^{50}$ and —NR$^{48}$C(=O)—NR$^{48}$R$^{49}$.

In one aspect, $R^{30}$ ad $R^{31}$ are each independently selected from the group consisting of hydrogen, chlorine, fluorine, CN, —C(=O)OH, hydroxy, —NHC(=O)C$_{1-4}$alkyl, —OC$_{1-4}$ alkyl, —OCH$_2$CH$_2$OH, —NHS(=O)$_2$C$_{1-4}$alkyl and —NHC(=O)—N(C$_{1-4}$alkyl)$_2$.

In one aspect, $R^{30}$, $R^{31}$, $R^{42}$ and $R^{43}$ are each independently selected from the group consisting of —(CR$^{44}$R$^{45}$)$_m$—C$_3$-C$_{10}$heterocyclyl substituted with $R^{54}$, —(CR$^{44}$R$^{45}$)$_m$—C$_3$-C$_{10}$-cycloalkyl substituted with $R^{55}$, —(CR$^{44}$R$^{45}$)$_m$-aryl substituted with $R^{56}$ and $R^{57}$ and —(CR$^{44}$R$^{45}$)$_m$-heteroaryl substituted with $R^{56}$ and $R^{57}$.

In one aspect, $R^{30}$, $R^{31}$, $R^{42}$ and $R^{43}$ are each independently selected from the group consisting of —C$_3$-C$_{10}$heterocyclyl substituted with $R^{54}$, —C$_3$-C$_{10}$cycloalkyl substituted with $R^{55}$, -phenyl substituted with $R^{56}$ and $R^{57}$ and -heteroaryl substituted with $R^{56}$ and $R^{57}$.

In one aspect, $R^{30}$, $R^{31}$, $R^{42}$ and $R^{43}$ are each independently selected from the group consisting of tetrahydropyranyl, piperidinyl, pyrrolidinyl and morpholinyl substituted with $R^{54}$, cyclopropyl, cyclobutyl, cyclohexyl and cyclopentyl substituted with $R^{55}$, phenyl substituted with $R^{56}$ and $R^{57}$ and imidazolyl, pyrazolyl, isoxazolyl, pyridazinyl, pyrazinyl pyrimidinyl and pyridinyl substituted with $R^{56}$ and $R^{57}$.

In one aspect, $R^{30}$, $R^{31}$, $R^{42}$ and $R^{43}$ are each independently selected from the group consisting of tetrahydropyranyl, piperidinyl, pyrrolidinyl and morpholinyl substituted with $R^{54}$, cyclopropyl, cyclobutyl, cyclohexyl and cyclopentyl substituted with $R^{55}$, phenyl substituted with $R^{56}$ and $R^{57}$ and pyridazinyl, pyrazinyl pyrimidinyl and pyridinyl substituted with $R^{56}$ and $R^{57}$.

In one aspect, $R^{90}$ and $R^{91}$ are each independently selected from the group consisting of hydrogen, halogen, =O, —CN, —C(=O)OH, —C(=O)$R^{46}$, —CH(OH)—$R^{47}$, hydroxy, trifluoromethyl, —(C$R^{44}R^{45}$)$_m$—C(=O)—N$R^{48}R^{49}$, —(C$R^{44}R^{45}$)$_m$—N$R^{45}$C(=O)$R^{46}$, —(C$R^{44}R^{45}$)$_m$—O$R^{49}$, —(C$R^{44}R^{45}$)$_m$—S$R^{49}$, —(C$R^{44}R^{45}$)$_m$—S(=O)$_2R^{50}$, —(C$R^{44}R^{45}$)$_m$—S(=O)$_2$N$R^{48}R^{49}$, —(C$R^{44}R^{45}$)$_m$—N$R^{45}$S(=O)$_2R^{50}$, —(C$R^{44}R^{45}$)$_m$—N$R^{48}R^{49}$, —(C$R^{44}R^{45}$)$_m$—N$R^{48}$C(=O)—N$R^{48}R^{49}$, —(C$R^{44}R^{45}$)$_m$—C=C$R^{51}R^{52}$, and —(C$R^{44}R^{45}$)$_m$—C≡C—$R^{53}$.

In one aspect, $R^{90}$ and $R^{91}$ are each independently selected from the group consisting of hydrogen, fluorine, chlorine, =O, —CN, —C(=O)OH, hydroxy, —(C$R^{44}R^{45}$)$_m$—C(=O)—N$R^{48}R^{49}$, —(C$R^{44}R^{45}$)$_m$—N$R^{48}$C(=O)$R^{46}$, —(C$R^{44}R^{45}$)$_m$—O$R^{49}$, —(C$R^{44}R^{45}$)$_m$—S$R^{49}$, —(C$R^{44}R^{45}$)$_m$—S(=O)$_2R^{50}$, —(C$R^{44}R^{45}$)$_m$—S(=O)$_2$N$R^{48}R^{49}$, —(C$R^{44}R^{45}$)$_m$—N$R^{45}$S(=O)$_2R^{50}$, —(C$R^{44}R^{45}$)$_m$—N$R^{48}$C(=O)—N$R^{48}R^{49}$, —(C$R^{44}R^{45}$)$_m$—C=C$R^{51}R^{52}$, and —(C$R^{44}R^{45}$)$_m$—C≡C—$R^{53}$.

In one aspect, $R^{90}$ and $R^{91}$ are each independently selected from the group consisting of hydrogen, fluorine, chlorine, —CN, —C(=O)OH, —N$R^{48}$C(=O)$R^{46}$, —N$R^{45}$S(=O)$_2R^{50}$ and —N$R^{45}$C(=O)—N$R^{48}R^{49}$.

In one aspect, $R^{90}$ and $R^{91}$ are each independently selected from the group consisting of hydrogen, fluorine, chlorine, =O, —CN, —C(=O)OH, —C(=O)—N$R^{48}R^{49}$, —O$R^{49}$, —S$R^{49}$, —S(=O)$_2R^{50}$, —S(=O)$_2$N$R^{48}R^{49}$, —C=C$R^{51}R^{52}$ and —C≡C—$R^{53}$.

In one aspect, $R^{90}$ and $R^{91}$ are each independently selected from the group consisting of hydrogen, —(C$R^{44}R^{45}$)$_m$—$C_3$-$C_{10}$heterocyclyl substituted with $R^{54}$, —(C$R^{44}R^{45}$)$_m$—$C_3$-$C_{10}$cycloalkyl substituted with $R^{55}$, —(C$R^{44}R^{45}$)$_m$-aryl substituted with $R^{56}$ and $R^{57}$ and —(C$R^{44}R^{45}$)$_m$-heteroaryl substituted with $R^{56}$ and $R^{57}$.

In one aspect, $R^{90}$ and $R^{91}$ are each independently selected from the group consisting of hydrogen, tetrahydropyranyl, piperidinyl, pyrrolidinyl and morpholinyl substituted with $R^{54}$, cyclopropyl, cyclobutyl, cyclohexyl and cyclopentyl substituted with $R^{55}$, phenyl substituted with $R^{56}$ and $R^{57}$ and imidazolyl, pyrazolyl, isoxazolyl, pyridazinyl, pyrazinyl pyrimidinyl and pyridinyl substituted with $R^{56}$ and $R^{57}$.

In one aspect, $R^{90}$ and $R^{91}$ are each independently selected from the group consisting of hydrogen, tetrahydropyranyl, piperidinyl and morpholinyl substituted with $R^{54}$, cyclopropyl, cyclobutyl and cyclohexyl substituted with $R^{55}$, phenyl substituted with $R^{56}$ and $R^{57}$ and pyridazinyl, pyrazinyl pyrimidinyl and pyridinyl substituted with $R^{56}$ and $R^{57}$.

In one aspect, m is 0.

In one aspect, m is 1.

In one aspect, $R^{32}$, $R^{33}$, $R^{37}$, $R^{38}$, $R^{39}$, $R^{40}$ and $R^{41}$ are each independently selected from the group consisting of hydrogen, $C_1$-$C_6$alkyl and $C_3$-$C_{10}$cycloalkyl, wherein said $C_1$-$C_6$alkyl and $C_3$-$C_{10}$cycloalkyl are optionally substituted with one or two independently selected $R^{58}$.

In one aspect, $R^{32}$, $R^{33}$, $R^{37}$, $R^{38}$, $R^{39}$, $R^{40}$ and $R^{41}$ are each independently selected from the group consisting of hydrogen, $C_1$-$C_6$alkyl and $C_3$-$C_{10}$cycloalkyl, wherein said $C_1$-$C_6$alkyl and $C_3$-$C_{10}$cycloalkyl are optionally substituted with one $R^{58}$.

In one aspect, $R^{32}$, $R^{33}$, $R^{37}$, $R^{38}$, $R^{39}$, $R^{40}$ and $R^{41}$ are each independently selected from the group consisting of hydrogen, methyl, ethyl and isopropyl, trifluoromethyl and cyclopropyl, cyclobutyl, cyclohexyl and cyclopentyl, wherein said methyl, ethyl and isopropyl, trifluoromethyl and cyclopropyl, cyclobutyl, cyclohexyl and cyclopentyl are optionally substituted with one $R^{58}$.

In one aspect, $R^{32}$, $R^{33}$, $R^{37}$, $R^{38}$, $R^{39}$, $R^{40}$ and $R^{41}$ are each independently selected from the group consisting of hydrogen, $C_3$-$C_{10}$heterocyclyl, aryl and heteroaryl, wherein said $C_3$-$C_{10}$heterocyclyl, aryl and heteroaryl are optionally substituted with one or two independently selected $R^{58}$.

In one aspect, $R^{32}$, $R^{33}$, $R^{37}$, $R^{38}$, $R^{39}$, $R^{40}$ and $R^{41}$ are each independently selected from the group consisting of hydrogen, $C_3$-$C_{10}$heterocyclyl, aryl and heteroaryl, wherein said $C_3$-$C_{10}$heterocyclyl, aryl and heteroaryl are optionally substituted with one or two independently selected $R^{58}$.

In one aspect, $R^{32}$, $R^{33}$, $R^{37}$, $R^{38}$, $R^{39}$, $R^{40}$ and $R^{41}$ are each independently selected from the group consisting of hydrogen, tetrahydropyranyl, piperidinyl, pyrrolidinyl, morpholinyl, phenyl, imidazolyl, pyrazolyl, isoxazolyl, pyridazinyl, pyrazinyl, pyrimidinyl and pyridinyl wherein said tetrahydropyranyl, piperidinyl, pyrrolidinyl, morpholinyl, phenyl, imidazolyl, pyrazolyl, isoxazolyl, pyridazinyl, pyrazinyl pyrimidinyl and pyridinyl are optionally substituted with one or two independently selected $R^{58}$.

In one aspect, $R^{32}$, $R^{33}$, $R^{37}$, $R^{38}$, $R^{39}$, $R^{40}$ and $R^{41}$ are each independently selected from the group consisting of hydrogen, tetrahydropyranyl, piperidinyl, morpholinyl, phenyl, pyridazinyl, pyrazinyl, pyrimidinyl and pyridinyl wherein said tetrahydropyranyl, piperidinyl, morpholinyl, phenyl, pyridazinyl, pyrazinyl, pyrimidinyl and pyridinyl are optionally substituted with one $R^{58}$.

In one aspect, $R^{34}$, $R^{35}$, and $R^{36}$ are each independently selected from the group consisting of hydrogen, $C_1$-$C_6$alkyl, $C_3$-$C_{10}$cycloalkyl and heteroaryl, wherein said $C_1$-$C_6$alkyl, $C_3$-$C_{10}$cycloalkyl and heteroaryl are optionally substituted with one, two or three substituents independently selected from the group consisting of halogen, methyl, ethyl and hydroxyl.

In one aspect, $R^{34}$ and $R^{35}$ together with the nitrogen to which they are attached form a piperidinyl, pyrrolidinyl and morpholinyl ring, wherein said ring optionally is substituted with one or two substituents independently selected from the group consisting of hydroxy or fluorine.

In one aspect, $R^{34}$, $R^{35}$, and $R^{36}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, methyl, ethyl and hydroxyl.

In one aspect, $R^{34}$, $R^{35}$, and $R^{36}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one substituent independently selected from the group consisting of fluorine, methyl, ethyl and hydroxyl.

In one aspect, $R^{26}$, $R^{27}$, $R^{46}$, $R^{47}$, $R^{49}$, $R^{50}$, $R^{51}$, $R^{53}$ and $R^{52}$ are each independently selected from the group consisting of hydrogen, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy.

In one aspect, $R^{54}$, $R^{55}$, $R^{56}$ and $R^{57}$ are each independently selected from the group consisting of hydrogen, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy.

In one aspect, $R^{26}$, $R^{27}$, $R^{46}$, $R^{47}$, $R^{49}$, $R^{50}$, $R^{51}$, $R^{53}$ and $R^{52}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine, methyl, ethyl, methoxy, ethoxy, —OCH$_2$CH$_2$OH, carboxy and hydroxy.

In one aspect, $R^{54}$, $R^{55}$, $R^{56}$ and $R^{57}$ are each independently selected from the group consisting of hydrogen, halogen, —CN, trifluoromethyl, —OCH$_2$CH$_2$OH, hydroxyl.

In one aspect, $R^{54}$, $R^{55}$, $R^{56}$ and $R^{57}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine methyl, ethyl, methoxy, ethoxy, —OCH$_2$CH$_2$OH, carboxy and hydroxy.

In one aspect, $R^{48}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

In one aspect, $R^{49}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

In one aspect, $R^{49}$ is H and $R^{48}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

In one aspect, $R^{48}$ is H and $R^{49}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

In one aspect, $R^{48}$ and $R^{49}$ together with the nitrogen to which they are attached form a piperidinyl, pyrrolidinyl and morpholinyl ring, wherein said ring optionally is substituted with one or two substituents independently selected from the group consisting of hydroxy and fluoride.

In one aspect, $R^{58}$ are each independently selected from selected from the group consisting of halogen, —CN, hydroxy, oxo, —C(=O)OH, —S(=O)$_2$R$^{59}$, —S—NR$^{60}$R$^{61}$, S(=O)$_2$NR$^{60}$R$^{61}$, cyclopropyl, —OR$^{59}$, —SR$^{59}$, $C_1$-$C_6$alkyl, —C(=O)NR$^{60}$R$^{61}$, —NR$^{60}$C(=O)NR$^{61}$R$^{60}$, —NR$^{60}$S(=O)$_2$R$^{59}$ and —NC(=O)R$^{59}$.

In one aspect, $R^{58}$ is selected from the group consisting of fluorine, chlorine, —CN, hydroxy, oxo, —C(=O)OH, —S(=O)$_2$R$^{59}$, —S(=O)$_2$NR$^{60}$R$^{61}$, cyclopropyl, —OR$^{59}$, —SR$^{59}$, methyl, ethyl, isopropyl, —C(=O)NR$^{60}$R$^{61}$, —NR$^{60}$C(=O)NR$^{61}$R$^{60}$, —NR$^{60}$S(=O)$_2$R$^{59}$ and —NC(=O)R$^{59}$.

In one aspect, $R^{58}$ are each independently selected from selected from the group consisting of fluorine, chlorine, —CN, hydroxy, oxo, —C(=O)OH, —S(=O)$_2$R$^{59}$, cyclopropyl, —OR$^{59}$, methyl, ethyl, isopropyl and —C(=O)NR$^{60}$R$^{61}$.

In one aspect, $R^{58}$ are each independently selected from selected from the group consisting of —S(=O)$_2$NR$^{60}$R$^{61}$, —SR$^{59}$, —NR$^{60}$C(=O)NR$^{61}$R$^{60}$, —NR$^{60}$S(=O)$_2$R$^{59}$ and —NC(=O)R$^{59}$.

In one aspect, $R^{59}$ is selected from the group consisting of hydrogen, $C_1$-$C_6$alkyl and $C_3$-$C_{10}$cycloalkyl wherein said —C$_6$alkyl, $C_3$-$C_{10}$cycloalkyl are optionally substituted with one, two or three substituents independently selected from the group consisting of halogen, methyl, ethyl, methoxy, ethoxy trifluoromethyl and hydroxy.

In one aspect, $R^{59}$ is selected from the group consisting of hydrogen, phenyl and heteroaryl, wherein said, phenyl and heteroaryl are optionally substituted with one, two or three substituents independently selected from the group consisting of halogen, methyl, ethyl, methoxy, ethoxy and hydroxy.

In one aspect, $R^{59}$ is selected from the group consisting of hydrogen, methyl, ethyl and isopropyl, cyclopropyl, cyclobutyl, cyclohexyl, cyclopentyl, phenyl, imidazolyl, pyrazolyl, isoxazolyl, pyridazinyl, pyrazinyl, pyrimidinyl and pyridinyl, wherein said methyl, ethyl and isopropyl, cyclopropyl, cyclobutyl, cyclohexyl, cyclopentyl, phenyl, imidazolyl, pyrazolyl, isoxazolyl, pyridazinyl, pyrazinyl, pyrimidinyl and pyridinyl are optionally substituted with one, two or three substituents independently selected from the group consisting of halogen, methyl, ethyl, methoxy, ethoxy and hydroxy.

In one aspect, $R^{60}$ are each independently selected from the group consisting of hydrogen, methyl, ethyl, isopropyl, tetrahydropyranyl, piperidinyl, pyrrolidinyl, morpholinyl, cyclopropyl, cyclobutyl, cyclohexyl, cyclopentyl, and heteroaryl, wherein said methyl, ethyl, isopropyl, tetrahydropyranyl, piperidinyl, pyrrolidinyl, morpholinyl, cyclopropyl, cyclobutyl, cyclohexyl, cyclopentyl, and heteroaryl are optionally substituted with one or two substituents independently selected from the group consisting of fluorine, chlorine and hydroxy.

In one aspect, $R^{60}$ are each independently selected from the group consisting of hydrogen, methyl, ethyl, isopropyl, cyclopropyl, wherein said methyl, ethyl, isopropyl and cyclopropyl are optionally substituted with one or two substituents independently selected from the group consisting of fluorine, chlorine and hydroxy.

In one aspect, $R^{61}$ are each independently selected from the group consisting of hydrogen, $C_1$-$C_6$alkyl, $C_3$-$C_{10}$heterocyclyl, $C_3$-$C_{10}$cycloalkyl and heteroaryl, wherein said $C_1$-$C_6$alkyl, $C_3$-$C_{10}$heterocyclyl, $C_3$-$C_{10}$cycloalkyl and heteroaryl are optionally substituted with one or two substituents independently selected from the group consisting of halogen and hydroxy.

In one aspect, $R^{61}$ are each independently selected from the group consisting of hydrogen, methyl, ethyl, isopropyl, tetrahydropyranyl, piperidinyl, pyrrolidinyl, morpholinyl, cyclopropyl, cyclobutyl, cyclohexyl, cyclopentyl, and heteroaryl, wherein said methyl, ethyl, isopropyl, tetrahydropyranyl, piperidinyl, pyrrolidinyl, morpholinyl, cyclopropyl, cyclobutyl, cyclohexyl, cyclopentyl, and heteroaryl are optionally substituted with one or two substituents independently selected from the group consisting of fluorine, chlorine and hydroxy.

In one aspect, $R^{93}$ is selected from the group consisting of hydrogen, methyl, ethyl, isopropyl, cyclopropyl, cyclobutyl, cyclohexyl, cyclopentyl, tetrahydropyranyl, piperidinyl, pyrrolidinyl, morpholinyl, phenyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, tetrahydropyranyl, piperidinyl, pyrrolidinyl, morpholinyl, phenyl, imidazolyl, pyrazolyl, isoxazolyl, pyridazinyl, pyrazinyl, pyrimidinyl and pyridinyl are optionally substituted with one, two or three independently selected $R^{58}$.

In one aspect, $R^{93}$ is selected from the group consisting of hydrogen, methyl, ethyl, isopropyl, cyclopropyl, cyclobutyl, cyclohexyl, cyclopentyl, tetrahydropyranyl, piperidinyl, morpholinyl, phenyl, pyrimidinyl and pyridinyl, wherein said methyl, ethyl, isopropyl, cyclopropyl, cyclobutyl, cyclohexyl, cyclopentyl, tetrahydropyranyl, piperidinyl, morpholinyl, phenyl, pyrimidinyl and pyridinyl are optionally substituted with one, two or three independently selected $R^{58}$.

In one aspect, $R^{94}$ and $R^{95}$ are each independently selected from the group consisting of hydrogen, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine, methyl, ethyl and hydroxy.

In one aspect, $R^{94}$ is hydrogen and $R^{95}$ are selected from the group consisting of hydrogen, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine, methyl, ethyl and hydroxy.

In one aspect, $R^{94}$ and $R^{95}$ together with the nitrogen to which they are attached form a piperidinyl, pyrrolidinyl and morpholinyl ring, wherein said ring optionally is substituted with one or two substituents independently selected from the group consisting of hydroxy or fluorine.

In one aspect, $R^{94}$ and $R^{95}$ together with the nitrogen to which they are attached form a piperidinyl and pyrrolidinyl ring, wherein said ring optionally is substituted with one or two substituents independently selected from the group consisting of hydroxy or fluorine.

In one aspect, $R^{62}$ is selected from the group consisting of fluoride, chloride, methyl, —C(=O)OH, —CH(OH)—$R^{47}$, —C(=O)—$NR^{48}R^{49}$, —$NR^{48}$C(=O)$R^{46}$, —$SR^{49}$, —S(=O)$_2R^{50}$, —S(=O)$_2NR^{48}R^{49}$, —$NR^{48}$S(=O)$_2R^{50}$, —$NR^{48}$C(=O)—$NR^{48}R^{49}$, —C=C—$R^{51}R^{52}$, —C≡C—$R^{53}$, and $CH_2CH_2OH$, —$CH_2CH_2OH$.

In one aspect, $R^{62}$ is selected from the group consisting of $C_3$-$C_{10}$heterocyclyl substituted with $R^{54}$, $C_3$-$C_{10}$cycloalkyl substituted with $R^{55}$, aryl substituted with $R^{56}$ and $R^{57}$ and heteroaryl substituted with $R^{56}$ and $R^{57}$.

In one aspect, $R^{62}$ is selected from the group consisting of fluorine, chlorine, methyl, —CH(OH)-cyclopropyl, —C(=O)—$NR^{48}R^{49}$, —$NR^{48}$C(=O)$R^{46}$, —S(=O)$_2R^{50}$, —S(=O)$_2NR^{48}R^{49}$, —$NR^{48}$S(=O)$_2R^{50}$, —$NR^{48}$C(=O)—$NR^{48}R^{49}$, $CH_2CH_2OH$, —$CH_2CH_2OH$.

In one aspect, $R^{62}$ is selected from the group consisting of tetrahydropyranyl, piperidinyl, pyrrolidinyl, morpholinyl substituted with $R^{54}$, cyclopropyl, cyclobutyl, cyclohexyl, cyclopentyl substituted with $R^{55}$, phenyl substituted with $R^{56}$ and $R^{57}$ and imidazolyl, pyrazolyl, isoxazolyl, pyridazinyl, pyrazinyl, pyrimidinyl and pyridinyl substituted with $R^{56}$ and $R^{57}$.

In one aspect, $R^{63}$ is selected from the group consisting of hydrogen, fluoride, chloride, hydroxy, oxo, —S(=O)$_2R^{59}$, —S(=O)$_2NR^{60}R^{61}$, —S(=O)$NR^{60}R^{61}$ cyclopropyl, —$OR^{59}$, methyl, ethyl, isopropyl, —C(=O)$NR^{60}R^{61}$, —$NR^{60}$C(=O)$NR^{61}R^{60}$; —$NR^{60}$S(=O)$_2R^{59}$, and —N(C=O)$R^{59}$.

In one aspect, $R^{63}$ is selected from the group consisting of hydrogen, fluoride, chloride, hydroxy, oxo, —S(=O)$_2R^{59}$, —S(=O)$_2NR^{60}R^{61}$, —S(=O)$NR^{60}R^{61}$ cyclopropyl, —$OR^{59}$, methyl, ethyl, isopropyl and —C(=O)$NR^{60}R^{61}$.

In one aspect, $R^{63}$ is selected from the group consisting of hydrogen, fluoride, chloride, trifluoromethyl, hydroxy, oxo, —S(=O)$_2$cyclopropyl, —S(=O)$_2$methyl, cyclopropyl, —$OR^{59}$, methyl, ethyl and isopropyl.

In one aspect, the compound of the invention is selected from the group consisting of N-(5-Hydroxy-adamantan-2-yl)-N-methyl-3-phenethyloxy-benzamide, N-(5-Hydroxy-adamantan-2-yl)-3-phenethyloxy-benzamide, 3-Cyclohexylmethoxy-N-(5-hydroxy-adamantan-2-yl)-N-methyl-benzamide, N-(5-Hydroxy-adamantan-2-yl)-N-methyl-3-(1-methyl-butoxy)-benzamide, N-(5-Hydroxy-adamantan-2-yl)-3-methoxy-N-methyl-benzamide, N-(5-Hydroxy-adamantan-2-yl)-N-methyl-3-(2-pyridin-2-yl-ethoxy)-benzamide, N-(5-Hydroxy-adamantan-2-yl)-3-(2-pyridin-2-yl-ethoxy)-benzamide, 3-Benzyloxy-N-(5-hydroxy-adamantan-2-yl)-benzamide, N-(5-Hydroxy-adamantan-2-yl)-3-(2-morpholin-4-yl-ethoxy)-benzamide, 4-{2-[3-(5-Hydroxy-adamantan-2-ylcarbamoyl)-phenoxy]-ethyl}-piperidine-1-carboxylic acid isopropylamide, 3-[2-(1-Cyclopropanesulfonyl-piperidin-4-yl)-ethoxy]-N-(5-hydroxy-adamantan-2-yl)-benzamide, 3-(6-Chloro-pyridin-3-ylmethoxy)-N-(5-hydroxy-adamantan-2-yl)-benzamide, N-(5-Hydroxy-adamantan-2-yl)-3-(tetrahydro-pyran-4-yl-methoxy)-benzamide, N-(5-Hydroxy-adamantan-2-yl)-3-[2-(tetrahydro-pyran-4-yl)-ethoxy]-benzamide, N-(5-Hydroxy-adamantan-2-yl)-3-[2-(2-oxo-pyrrolidin-1-yl)-ethoxy]-benzamide, N-(5-Hydroxy-adamantan-2-yl)-N-methyl-3-(tetrahydro-pyran-4-yloxy)-benzamide', (3-Hydroxy-8-aza-bicyclo[3.2.1]oct-8-yl)-[3-(tetrahydro-pyran-4-ylmethoxy)-phenyl]-methanone, (3-Hydroxy-8-aza-bicyclo[3.2.1]oct-8-yl)-{3-[2-(tetrahydro-pyran-4-yl)-ethoxy]-phenyl}-methanone, (3-Hydroxy-8-aza-bicyclo[3.2.1]oct-8-yl)-[3-(4-hydroxy-cyclohexylmethoxy)-phenyl]-methanone.

In one embodiment the compound of the invention is an agent useful for the treatment, prevention and/or prophylaxis of any conditions, disorders and diseases wherein a modulation or an inhibition of the activity of 11βHSD1 is beneficial.

In one embodiment the compound of the invention is an agent useful for the treatment, prevention and/or prophylaxis of any conditions, disorders and diseases that are influenced by intracellular glucocorticoid levels.

In one embodiment the compound of the invention is an agent useful for the treatment, prevention and/or prophylaxis of conditions, disorders or diseases selected from the group consisting of the metabolic syndrome, insulin resistance, dyslipidemia, hypertension and obesity.

In one embodiment the compound of the invention is an agent useful for the treatment, prevention and/or prophylaxis of type 2 diabetes, impaired glucose tolerance (IGT), impaired fasting glucose (IFG).

In one embodiment the compound of the invention is an agent useful for the delaying or prevention of the progression from IGT into type 2 diabetes.

In one embodiment the compound of the invention is an agent useful for delaying or prevention of the progression of the metabolic syndrome into type 2 diabetes.

In one embodiment the compound of the invention is an agent useful for the treatment, prevention and/or prophylaxis of adverse effects of glucocorticoid receptor agonist treatment or therapy.

In one aspect of the invention, the compounds according to the invention have a $IC_{50}$ value as tested as described under the heading "PHARMACOLOGICAL METHODS" below 1000 nM, in a further aspect below 500 nM, in yet a further aspect below 300 nM and in yet a further aspect below 200 nM.

The compounds of the present invention have asymmetric centers and may occur as racemates, racemic mixtures, and as individual enantiomers or diastereoisomers, with all isomeric forms being included in the present invention as well as mixtures thereof.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxyl-naphthoates, glycerophosphates, ketoglutarates and the like. Further examples of pharmaceutically acceptable inorganic or organic acid addition salts include the pharmaceutically acceptable salts listed in J. Pharm. Sci., 66, 2 (1977), which is incorporated herein by reference. Examples of metal salts include lithium, sodium, potassium, barium, calcium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

Further, some of the compounds of the present invention may form solvates with water or common organic solvents. Such solvates are encompassed within the scope of the invention. The pharmaceutically acceptable salts are prepared by reacting a compound of the present invention with 1 to 4 equivalents of a base such as sodium hydroxide, sodium methoxide, sodium hydride, potassium tert-butoxide, calcium hydroxide, magnesium hydroxide and the like, in solvents like ether, THF, methanol, tert-butanol, dioxane, isopropanol, ethanol etc. Mixtures of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al. in "Enantiomers, Racemates and Resolution" (Wiley Interscience, 1981). More specifically the compound of the present invention may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of the compounds forming part of this invention may be prepared by crystallization of said compounds under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, it spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in "Design of Prodrugs", ed. H. Bundgaard, Elsevier, 1985.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver and/or poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active.

It is within the scope of the invention to modify the compounds of the present invention, termed the 'original compound', by attaching chemical groups that will improve the bioavailability of said compounds in such a way that the uptake in cells or mammals is facilitated.

Examples of said modifications, which are not intended in any way to limit the scope of the invention, include changing of one or more carboxy groups to esters (for instance methyl esters, ethyl esters, tert-butyl, acetoxymethyl, pivaloyloxymethyl esters or other acyloxymethyl esters). Compounds of the invention, original compounds, such modified by attaching chemical groups are termed 'modified compounds'.

The invention also encompasses active metabolites of the present compounds.

The compounds according to the invention alter, and more specifically, reduce the level of active intracellular glucocorticoid and are accordingly useful for the treatment, prevention and/or prophylaxis of disorders and diseases in which such a modulation or reduction is beneficial.

Accordingly, the present compounds may be applicable for the treatment, prevention and/or prophylaxis of the metabolic syndrome, insulin resistance, dyslipidemia, hypertension, obesity, type 2 diabetes, impaired glucose tolerance (IGT), impaired fasting glucose (IFG), Latent Autoimmune Diabetes in the Adult (LADA), type 1 diabetes, diabetic late complications including cardiovascular diseases, cardiovascular disorders, disorders of lipid metabolism, neurodegenerative and psychiatric disorders, dysregulation of intraocular pressure including glaucoma, immune disorders, inappropriate immune responses, musculo-skeletal disorders, gastrointestinal disorders, polycystic ovarie syndrome (PCOS), reduced hair growth or other diseases, disorders or conditions that are influenced by intracellular glucocorticoid levels, adverse effects of increased blood levels of active endogenous or exogenous glucocorticoid, and any combination thereof, adverse effects of increased plasma levels of endogenous active glucocorticoid, Cushing's disease, Cushing's syndrome, adverse effects of glucocorticoid receptor agonist treatment of autoimmune diseases, adverse effects of glucocorticoid receptor agonist treatment of inflammatory diseases, adverse effects of glucocorticoid receptor agonist treatment of diseases with an inflammatory component, adverse effects of glucocorticoid receptor agonist treatment as a part of cancer chemotherapy, adverse effects of glucocorticoid receptor agonist treatment for surgical/post-surgical or other trauma, adverse effects of glucocorticoid receptor agonist therapy in the context of organ or tissue transplantation or adverse effects of glucocorticoid receptor agonist treatment in other diseases, disorders or conditions where glucocorticoid receptor agonists provide clinically beneficial effects.

More specifically the present compounds may be applicable for the treatment, prevention and/or prophylaxis of the metabolic syndrome, type 2 diabetes, diabetes as a consequence of obesity, insulin resistance, hyperglycemia, prandial hyperglycemia, hyperinsulinemia, inappropriately low insulin secretion, impaired glucose tolerance (IGT), impaired fasting glucose (IFG), increased hepatic glucose production, type 1 diabetes, LADA, pediatric diabetes, dyslipidemia, diabetic dyslipidemia, hyperlipidemia, hypertriglyceridemia, hyperlipoproteinemia, hypercholesterolemia, decreased HDL cholesterol, impaired LDL/HDL ratio, other disorders of lipid metabolism, obesity, visceral obesity, obesity as a consequence of diabetes, increased food intake, hypertension, diabetic late complications, micro-/macroalbuminuria, nephropathy, retinopathy, neuropathy, diabetic ulcers, cardiovascular diseases, arteriosclerosis, atherosclerosis, coronary artery disease, cardiac hypertrophy, myocardial ischemia, heart insufficiency, congestional heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsy, addiction to chemical substances, disorders of intraocular pressure, glaucoma, polycystic ovary syndrome (PCOS), inappropriate immune responses, inappropriate T helper-1/T helper-2 polarisation, bacterial infections, mycobacterial infections, fungal infections, viral infections, parasitic infestations, suboptimal responses to immunizations, immune dysfunction, partial or complete baldness, or other diseases, disorders or conditions that are influenced by intracellular glucocorticoid levels and any combination thereof, adverse effects of glucocorticoid receptor agonist treatment of allergic-inflammatory diseases such as asthma and atopic dermatitis, adverse effects of glucocorticoid receptor agonist treatment of disorders of the respiratory system e.g. asthma, cystic fibrosis, emphysema, bronchitis, hypersensitivity, pneumonitis, eosinophilic pneumonias, pulmonary fibrosis, adverse effects of glucocorticoid receptor agonist treatment of inflammatory bowel disease such as Crohn's disease and ulcerative colitis; adverse effects of glucocorticoid receptor agonist treatment of disorders of the immune system, connective tissue and joints e.g. reactive arthritis, rheumatoid arthritis, Sjögren's syndrome, systemic lupus erythematosus, lupus nephritis, Henoch-Schönlein purpura, Wegener's granulomatosis, temporal arteritis, systemic sclerosis, vasculitis, sarcoidosis, dermatomyositis-polymyositis, pemphigus vulgaris; adverse effects of glucocorticoid receptor agonist treatment of endocrinological diseases such as hyperthyroidism, hypoaldosteronism, hypopituitarism; adverse effects of glucocorticoid receptor agonist treatment of hematological diseases e.g. hemolytic anemia, thrombocytopenia, paroxysmal nocturnal hemoglobinuria; adverse effects of glucocorticoid receptor agonist treatment of cancer such as spinal cord diseases, neoplastic compression of the spinal cord, brain tumours, acute lymphoblastic leukemia, Hodgkin's disease, chemotherapy-induced nausea, adverse effects of glucocorticoid receptor agonist treatment of diseases of muscle and at the neuro-muscular joint e.g. myasthenia gravis and heriditary myopathies (e.g. Duchenne muscular dystrophy), adverse effects of glucocorticoid receptor agonist treatment in the context of surgery & transplantation e.g. trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, tracheal transplantation, intestinal transplantation, corneal transplantation, skin grafting, keratoplasty, lens implantation and other procedures where immunosuppression with glucocorticoid receptor agonists is beneficial; adverse effects of glucocorticoid receptor agonist treatment of brain absess, nausea/vomiting, infections, hypercalcemia, adrenal hyperplasia, autoimmune hepatitis, spinal cord diseases, saccular aneurysms or adverse effects to glucocorticoid receptor agonist treatment in other diseases, disorders and conditions where glucocorticoid receptor agonists provide clinically beneficial effects.

Accordingly, in a further aspect the invention relates to a compound according to the invention for use as a pharmaceutical composition.

The invention also relates to pharmaceutical compositions comprising, as an active ingredient, at least one compound according to the invention together with one or more pharmaceutically acceptable carriers or diluents.

The pharmaceutical composition is preferably in unit dosage form, comprising from about 0.05 mg/day to about 2000 mg/day, preferably from about 1 mg/day to about 500 mg/day of a compound according to the invention.

In another embodiment, the patient is treated with a compound according to the invention for at least about 1 week, for at least about 2 weeks, for at least about 4 weeks, for at least about 2 months or for at least about 4 months.

In yet another embodiment, the pharmaceutical composition is for oral, nasal, transdermal, pulmonal or parenteral administration.

Furthermore, the invention relates to the use of a compound according to the invention for the preparation of a pharmaceutical composition for the treatment, prevention and/or prophylaxis of disorders and diseases wherein a modulation or an inhibition of the activity of 11βHSD1 is beneficial.

The invention also relates to a method for the treatment, prevention and/or prophylaxis of disorders and diseases wherein a modulation or an inhibition of the activity of 11βHSD1 is beneficial, the method comprising administering to a subject in need thereof an effective amount of a compound according to the invention.

In a preferred embodiment of the invention the present compounds are used for the preparation of a medicament for the treatment, prevention and/or prophylaxis of any diseases and conditions that are influenced by intracellular glucocorticoid levels as mentioned above.

Thus, in a preferred embodiment of the invention the present compounds are used for the preparation of a medicament for the treatment, prevention and/or prophylaxis of conditions and disorders where a decreased level of active intracellular glucocorticoid is desirable, such as the conditions and diseases mentioned above.

In yet a preferred embodiment of the invention the present compounds are used for the preparation of a medicament for the treatment, prevention and/or prophylaxis of the metabolic syndrome including insulin resistance, dyslipidemia, hypertension and obesity.

In yet another preferred embodiment of the invention the present compounds are used for the preparation of a medicament for the treatment, prevention and/or prophylaxis of type 2 diabetes, impaired glucose tolerance (IGT), impaired fasting glucose (IFG).

In yet another preferred embodiment of the invention the present compounds are used for the preparation of a pharmaceutical composition for the delaying or prevention of the progression from IGT to type 2 diabetes.

In yet another preferred embodiment of the invention the present compounds are used for the preparation of a pharmaceutical composition for the delaying or prevention of the progression of the metabolic syndrome into type 2 diabetes.

In still another preferred embodiment of the invention the present compounds are used for the preparation of a pharmaceutical composition for the treatment, prevention and/or prophylaxis of diabetic late complications including cardiovascular diseases; arteriosclerosis; atherosclerosis.

In a further preferred embodiment of the invention the present compounds are used for the preparation of a pharmaceutical composition for the treatment, prevention and/or prophylaxis of neurodegenerative and psychiatric disorders.

In yet a further preferred embodiment of the invention the present compounds are used for the preparation of a pharmaceutical composition for the treatment, prevention and/or prophylaxis of adverse effects of glucocorticoid receptor agonist treatment or therapy.

In another embodiment of the present invention, the route of administration may be any route which effectively transports a compound according to the invention to the appropriate or desired site of action, such as oral, nasal, buccal, transdermal, pulmonal, or parenteral.

In still a further aspect of the invention the present compounds are administered in combination with one or more further active substances in any suitable ratios. Such further active substances may e.g. be selected from antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin; dexamphetamine or amphetamine; fenfluramine or dexfenfluramine; sibutramine; orlistat; mazindol or phentermine.

Suitable antidiabetic agents include insulin, insulin analogues and derivatives such as those disclosed in EP 792 290 (Novo Nordisk A/S), e.g. $N^{\epsilon B29}$-tetradecanoyl des (B30) human insulin, EP 214 826 and EP 705 275 (Novo Nordisk A/S), e.g. $Asp^{B28}$ human insulin, U.S. Pat. No. 5,504,188 (Eli Lilly), e.g. $Lys^{B28}$ $Pro^{B29}$ human insulin, EP 368 187 (Aventis), eg Lantus, which are all incorporated herein by reference, GLP-1 (glucagon like peptide-1) and GLP-1 derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In one embodiment, the present compounds are administered in combination with insulin or an insulin analogue or derivative, such as $N^{\epsilon B29}$-tetradecanoyl des (B30) human insulin, Asp$^{B28}$ human insulin, Lys$^{B28}$ Pro$^{B29}$ human insulin, Lantus®, or a mix-preparation comprising one or more of these.

In a further embodiment the present compounds are administered in combination with a sulphonylurea e.g. tolbutamide, glibenclamide, glipizide or glicazide.

In another embodiment the present compounds are administered in combination with a biguanide e.g. metformin.

In yet another embodiment the present compounds are administered in combination with a meglitinide e.g. repaglinide or senaglinide.

In still another embodiment the present compounds are administered in combination with a thiazolidinedione e.g. troglitazone, ciglitazone, pioglitazone, rosiglitazone or compounds disclosed in WO 97/41097 such as 5-[[4-[3-Methyl-4-oxo-3,4-dihydro-2-quinazolinyl]-methoxy]phenyl-methyl]thiazolidine-2,4-dione or a pharmaceutically acceptable salt thereof, preferably the potassium salt.

In yet another embodiment the present compounds may be administered in combination with the insulin sensitizers disclosed in WO 99/19313 such as (−)3-[4-[2-Phenoxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor e.g. miglitol or acarbose.

In another embodiment the present compounds are administered in combination with an agent acting on the ATP-dependent potassium channel of the β-cells e.g. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g. cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment the present compounds are administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Further, the present compounds may be administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxpre-
nolol, amusolalul, carvedilol, labetalol, β2-receptor blockers e.g. S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g. bendroflumetazide, chlorothalidone, hydrochlorothiazide and clopamide), loop-diuretics (e.g. bumetanide, furosemide and torasemide) and potassium sparing diuretics (e.g. amiloride, spironolactone), endothelin ET-A antagonists such as ABT-546, ambrisetan, atrasentan, SB-234551, CI-1034, S-0139 and YM-598, endothelin antagonists e.g. bosentan and J-104133, renin inhibitors such as aliskiren, vasopressin V1 antagonists e.g. OPC-21268, vasopressinV2 antagonists such as tolvaptan, SR-121463 and OPC-31260, B-type natriuretic peptide agonists e.g. Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g. fenoldopam and ketanserin, adenosine A1 antagonists such as naftopidil, N-0861 and FK-352, thromboxane A2 antagonists such as KT2-962, endopeptidase inhibitors e.g. ecadotril, nitric oxide agonists such as LP-805, dopamine D1 antagonists e.g. MYD-37, dopamine D2 agonists such as nolomirole, n-3 fatty acids e.g. omacor, prostacyclin agonists such as treprostinil, beraprost, PGE1 agonists e.g. ecraprost, Na+/K+ ATPase modulators e.g. PST-2238, Potassium channel activators e.g. KR-30450, vaccines such as PMD-3117, Indapamides, CGRP-unigene, guanylate cyclase stimulators, hydralazines, methyldopa, docarpamine, moxonidine, CoAprovel, MondoBiotech-811.

Further reference can be made to Remington: The Science and Practice of Pharmacy, 19$^{th}$ Edition, Gennaro, Ed., Mack Publishing Co., Easton, Pa., 1995.

Furthermore, the present compounds may be administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), mometasone, triamcinolonacetonide, triamcinolonhexacetonide GW-685698, NXC-1015, NXC-1020, NXC-1021, NS-126, P-4112, P-4114, RU-24858 and T-25 series.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, crèmes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 2000 mg, e.g. from about 0.1 to about 1000 mg, from about 0.5 mg to about 500 mg., from about 1 mg to about 200 mg, e.g. about 100 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, contains a free base such salts are prepared in a conventional manner by treating a solution or suspension of the compound with a chemical equivalent of a pharmaceutically acceptable acid. When a compounds for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, syrup, phosphor-lipids, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |

| -continued | |
|---|---|
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

The compounds of the invention may be administered to a patient which is a mammal, especially a human in need thereof. Such mammals include also animals, both domestic animals, e.g. household pets, and non-domestic animals such as wildlife.

The present invention also relate to the below methods of preparing the compounds of the invention.

The features disclosed in the foregoing description may, both separately and in any combination thereof, be material for realising the invention in diverse forms thereof.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a formulation described herein as comprising a particular element should be understood as also describing a formulation consisting of that element, unless otherwise stated or clearly contradicted by context).

This invention includes all modifications and equivalents of the subject matter recited in the aspects or claims presented herein to the maximum extent permitted by applicable law.

The present invention is further illustrated in the following representative examples which are, however, not intended to limit the scope of the invention in any way.

The following examples and general procedures refer to intermediate compounds and final products for general formula (I)

EXAMPLES

The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions.

Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed by either elemental analysis or nuclear magnetic resonance (NMR), where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). HPLC analyses are performed using 5 μm C18 4×250 mm column eluted with various mixtures of water and acetonitrile, flow=1 ml/min, as described in the experimental section.

Preparative HPLC: Column: 1.9×15 cm Waters XTerra RP-18. Buffer: linear gradient 5-95% MeCN in water over 15 min, 0.1% TFA, flow rate of 15 ml/min. The pooled fractions are either evaporated to dryness in vacuo, or evaporated in vacuo until the MeCN is removed, and then frozen and freeze dried.

The abbreviations as used in the examples have the following meaning:
ADDP: 1,1'-(Azodicarbonyl)dipiperidine
CDCl$_3$: Deuterio chloroform
DCM: Dichloromethane
DEAD: 1,1'-Diethyl azodicarboxylate
DIAD: 1,1'-Disopropyl azodicarboxylate
DIC: N,N'-Diisopropylcarbodiimide
DMAP: 4-Dimethylaminopyridine
DMF: N,N-Dimethylformamide
DMSO-d$_6$: Hexadeuterio dimethylsulfoxide
DMSO: Dimethylsulfoxide
DIPEA: Diisopropylethylamine EDC: 1-(3-Dimethylaminopropyl)-3-ethylcarbodiimide hydrochloride
EtOAc: Ethyl acetate
HOBT: 1-Hydroxy-benzotriazole
hrs: hours
MeCN: Acetonitrile
min: minutes
NMP: N-Methylpyrrolidinone
TBAF: Tetrabutyl ammoniumfluoride
TEA: Triethylamine
TFA: Trifluoroacetic acid
THF: Tetrahydrofuran
TLC: Thin layer chromatography General Method A:

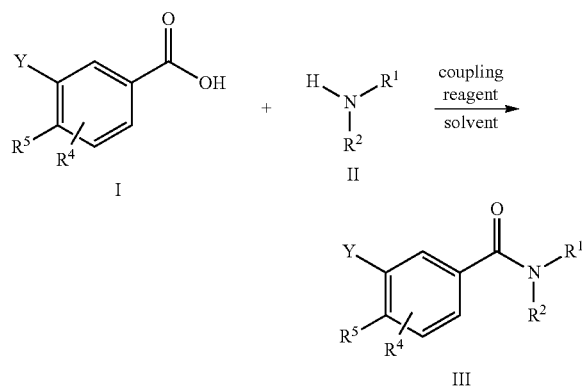

By allowing an acid (I) wherein $R^4$, $R^5$, and Y are defined as above to be coupled with an amine (II) wherein $R^1$ and $R^2$ are defined as above under standard amide bond forming conditions using a coupling reagent (e.g. HOBT, EDC and DIPEA in dry DMF) affording amide (III) wherein $R^1$, $R^2$, $R^4$, $R^5$, and Y are defined as above. Amines (II) are used as single isomers of as mixtures of two isomer, therefore amides (III) are isolated as mixtures of two isomers or as single isomers.

General Method B:

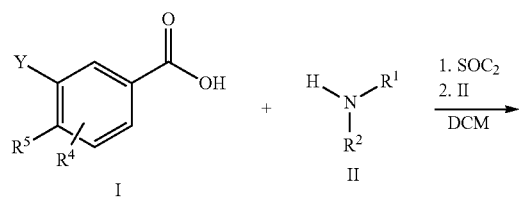

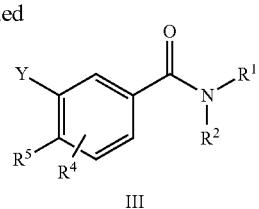

By allowing an acid (I) wherein $R^4$, $R^5$, and Y are defined as above to form the corresponding acid chloride by reaction with thionyl chloride, and then reacting the acid chloride with an amine (II) wherein $R^1$ and $R^2$ are defined as above under basic conditions (eg. triethyl amine, DIPEA, $K_2CO_3$ and the like) in a solvent (DCM, DMF, THF, NMP and the like) affording amide (III) wherein $R^1$, $R^2$, $R^4$, $R^5$, and Y are defined as above. Amines (II) are used as single isomers of as mixtures of two isomer, therefore amides (III) are isolated as mixtures of two isomers or as single isomers.

Alternatively, the acid chloride corresponding to acid (I) wherein $R^4$, $R^5$, and Y are defined as above can be used directly to react with amine (II) wherein $R^1$ and $R^2$ are defined as above under similar basic conditions.

General Method C:

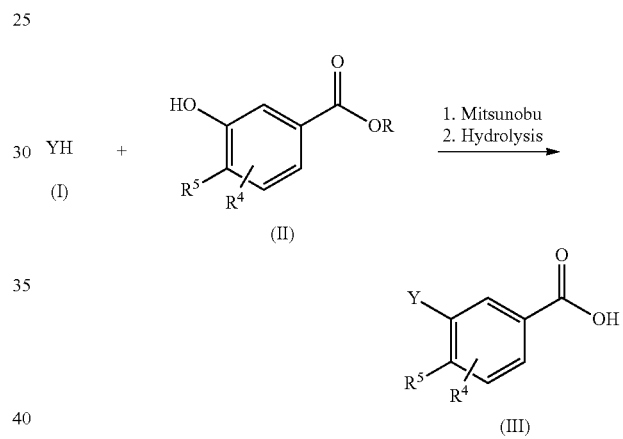

By allowing an alcohol (I) wherein Y is defined as above to be coupled with an benzoic acid ester (II) wherein R is a $C_1$-$C_4$alkyl and $R^4$ and $R^5$ are defined as above under standard Mitsunobu conditions using a phosphine reagent (e.g. triphenylphosphine or tributylphosphine) together with a diazocarbonyl reagent (e.g. DEAD, DIAD, ADDP) in a solvent (e.g. THF, dioxane, DCM) followed by standard alkaline hydrolysis (using a strong base such as NaH, NaOH and the like) affording acid (III) wherein $R^4$, $R^5$, and Y are defined as above.

| IUPAC | Molecule | LC-MS (m/z) |
|---|---|---|
| N-(5-Hydroxy-adamantan-2-yl)-N-methyl-3-phenethyloxy-benzamide | | 407 (M + 1) |

| IUPAC | Molecule | LC-MS (m/z) |
|---|---|---|
| N-(5-Hydroxy-adamantan-2-yl)-3-phenethyloxy-benzamide | | 393 (M + 1) |
| 3-Cyclohexylmethoxy-N-(5-hydroxy-adamantan-2-yl)-N-methyl-benzamide | | 399 (M + 1) |
| N-(5-Hydroxy-adamantan-2-yl)-N-methyl-3-(1-methyl-butoxy)-benzamide | | 373 (M + 1) |
| N-(5-Hydroxy-adamantan-2-yl)-3-methoxy-N-methyl-benzamide | | 316 (M + 1) |
| N-(5-Hydroxy-adamantan-2-yl)-N-methyl-3-(2-pyridin-2-yl-ethoxy)-benzamide | | 408 (M + 1) |
| N-(5-Hydroxy-adamantan-2-yl)-3-(2-pyridin-2-yl-ethoxy)-benzamide | | 394 (M + 1) |
| 3-Benzyloxy-N-(5-hydroxy-adamantan-2-yl)-benzamide | | 379 (M + 1) |

-continued

| IUPAC | Molecule | LC-MS (m/z) |
|---|---|---|
| N-(5-Hydroxy-adamantan-2-yl)-3-(2-morpholin-4-yl-ethoxy)-benzamide | | 402 (M + 1) |
| 4-{2-[3-(5-Hydroxy-adamantan-2-ylcarbamoyl)-phenoxy]-ethyl}-piperidine-1-carboxylic acid isopropylamide | | 485 (M + 1) |
| 3-[2-(1-Cyclopropanesulfonyl-piperidin-4-yl)-ethoxy]-N-(5-hydroxy-adamantan-2-yl)-benzamide | | 504 (M + 1) |
| 3-(6-Chloro-pyridin-3-ylmethoxy)-N-(5-hydroxy-adamantan-2-yl)-benzamide | | 413 (M) |
| N-(5-Hydroxy-adamantan-2-yl)-3-(tetrahydro-pyran-4-ylmethoxy)-benzamide | | 386 (M) |
| N-(5-Hydroxy-adamantan-2-yl)-3-[2-(tetrahydro-pyran-4-yl)-ethoxy]-benzamide | | 400 (M) |

| IUPAC | Molecule | LC-MS (m/z) |
|---|---|---|
| N-(5-Hydroxy-adamantan-2-yl)-3-[2-(2-oxo-pyrrolidin-1-yl)-ethoxy]-benzamide | | 400 (M + 1) |
| N-(5-Hydroxy-adamantan-2-yl)-N-methyl-3-(tetrahydro-pyran-4-yloxy)-benzamide | | 387 (M + 1) |
| (3-Hydroxy-8-aza-bicyclo[3.2.1]oct-8-yl)-[3-(tetrahydro-pyran-4-ylmethoxy)-phenyl]-methanone | | 346 (M + 1) |
| (3-Hydroxy-8-aza-bicyclo[3.2.1]oct-8-yl)-{3-[2-(tetrahydro-pyran-4-yl)-ethoxy]-phenyl}-methanone | | 360 (M) |
| (3-Hydroxy-8-aza-bicyclo[3.2.1]oct-8-yl)-[3-(4-hydroxy-cyclohexylmethoxy)-phenyl]-methanone | | 360 (M + 1) |

Example 1

Ethyl 3-cyclohexylmethoxy-benzoate

Cyclohexyl methanol (2.0 g, 17.5 mmol), ethyl 3-hydroxybenzoate (2.6 g, 15.8 mmol), tri-n-butyl phosphin (5.3 g, 26 mmol), and ADDP (6.6 g, 26 mmol) were dissolved in dry THF (100 ml) and stirred overnight at 20° C. under $N_2$. Water (100 ml) is added, and the resulting solution is extracted with DCM (3×100 ml). The combined organic layers were washed with water (100 ml), dried ($MgSO_4$) and evaporated. The crude mixture was purified by preparative HPLC to give 1.8 g of the title compound. LC-MS (m/z): 264 (M+2).

3-Cyclohexylmethoxy-benzoic acid

Ethyl 3-cyclohexylmethoxy benzoic acid (1.8 g, 6.7 mmol) was dissolved in ethanol (50 ml) and THF (50 ml), were upon NaOH (4 N, 10 ml) was added, and the solution was stirred overnight at 20° C. To the reaction mixture was added HCl (2 N, 200 ml), and the resulting solution was extracted with DCM (3×100 ml). The combined organic extracts were washed with water (100 ml), dried ($MgSO_4$) and evaporated to give 1.6 g of the title compound. LC-MS (m/z): 236 (M+2).

The following compounds were prepared by a method similar to Example 1

3-Phenethyloxy-benzoic acid

Prepared from 2-phenethylalcohol and ethyl 3-hydroxybenzoate. LC-MS (m/z): 265 (M+22 (Na)).

3-(Tetrahydro-pyran-4-ylmethoxy)-benzoic acid

Prepared from tetrahydro-2H-pyran-4-yl-methanol and ethyl 3-hydroxybenzoate.

3-[2-(Tetrahydro-pyran-4-yl)-ethoxy]-benzoic acid

Prepared from tetrahydro-2H-pyran-4-yl-ethanol and ethyl 3-hydroxybenzoate.

3-(Tetrahydro-pyran-4-yloxy)-benzoic acid

Prepared from 4-hydroxy-tetrahydropyrane and ethyl 3-hydroxybenzoate. LC-MS (m/z): 245 (M−23 (Na)).

Example 2

[4-(tert-Butyl-dimethyl-silanyloxy)-cyclohexyl]-methanol tert-Butyldimethylsilyl chloride (8.8 g, 58 mmol) was added to a solution of ethyl 4-hydroxycyclohexanecarboxylate (10 g, 58 mmol) and imidazole (4.3 g, 64 mmol) in DCM (300 ml), and the mixture was stirred overnight at 20° C. After washing with water (2×100 ml), the organic phase was dried (MgSO$_4$) and evaporated to dryness. The residue was dissolved in dry THF (300 ml) and cooled to −10° C. Dibal-H (1.0 M in toluene, 174 ml, 174 mmol) was added dropwise over a period of 60 min, while the temperature was kept at −10° C. After stirring for 2 hrs the reaction was quenched by slow addition of a saturated ammonium chloride solution (30 ml). The resulting suspension was filtered, and the filtrate was concentrated in vacuo to give 13 g of the title compound as a mixture of two isomers. LC-MS (m/z): 245 (M+1).

3-[4-(tert-butyl-dimethyl-silanyloxy)-cyclohexyl-methoxy]-benzoic acid

Prepared from [4-(tert-butyl-dimethyl-silanyloxy)-cyclohexyl]-methanol and ethyl 3-hydroxybenzoate by a method similar to Example 1.

Example 3

N-Boc-3-(2-piperidin-4-yl-ethoxy)-benzoic acid ethyl ester

N-Boc-4-piperidine ethanol (15 g, 65 mmol) and ethyl 3-hydroxybenzoate (11 g, 65 mmol) were dissolved in dry THF (750 ml) under N$_2$. To this was added tri-n-butylphosphin (24 ml, 98 mmol) and ADDP (25 g, 98 mmol) resulting in a suspension, which was stirred overnight at 20° C. The mixture was concentrated in vacuo to ~100 ml, filtered, and the filtrate was evaporated with silica gel. Flash chromatography (EtOAc/heptane 1:4) afforded 24 g of the title compound. LC-MS (m/z): 401 (M+23).

Ethyl 3-(2-piperidin-4-yl-ethoxy)-benzoate

TFA (25 ml) was added to a solution of N-Boc-3-(2-piperidin-4-yl-ethoxy)-benzoic acid ethyl ester (8.5 g, 22 mmol) in DCM (100 ml). Stirring overnight followed by evaporation of the solvents afforded 10 g of the title compound as the TFA salt. LC-MS (m/z): 279 (M+1).

Ethyl 3-[2-(1-isopropylcarbamoyl-piperidin-4-yl)-ethoxy]-benzoate

Ethyl 3-(2-piperidin-4-yl-ethoxy)-benzoate (1.0 g of the TFA salt, 2.6 mmol) was dissolved in DCM (10 ml), were upon DIPEA (1.3 ml, 7.7 mmol) and isopropyl isocyanate (0.33 g, 3.8 mmol) was added. The reaction mixture was shaken overnight at 20° C. Silica gel (10 ml) was added, and the solvent removed in vacuo. Flash chromatography (EtOAc/heptan 35:65 □ 55:45) provided 0.67 g of the title compound. LC-MS (m/z): 364 (M+2).

3-[2-(1-Isopropylcarbamoyl-piperidin-4-yl)-ethoxy]-benzoic acid

Ethyl 3-[2-(1-isopropylcarbamoyl-piperidin-4-yl)-ethoxy]-benzoate (0.67 g, 1.8 mmol) was dissolved in ethanol (25 ml), were upon NaOH (1 N, 10 ml) was added, and the solution was stirred overnight at 20° C. The reaction mixture was concentrated in vacuo, dissolved in HCl (1 N, 25 ml) and the resulting solution was extracted with EtOAc (3×25 ml). The combined organic extracts were dried (MgSO$_4$) and evaporated to give 0.62 of the title compound. LC-MS (m/z): 336 (M+2).

The following compound was prepared by a method similar to Example 3 with the variation stated.

3-[2-(1-cyclopropanesulfonyl-piperidin-4-yl)-ethoxy]-benzoic acid

Prepared from N-Boc-4-piperidine ethanol and ethyl 3-hydroxybenzoate, with the exception that ethyl 3-(2-piperidin-4-yl-ethoxy)-benzoate was converted to its corresponding sulfonamide as described below before the final alkaline hydrolysis to give the title compound. LC-MS (m/z): 377 (M+23 (Na)).

Sulfonamide Formation

DIPEA (1.3 ml, 7.7 mmol) was added to a solution of ethyl 3-(2-piperidin-4-yl-ethoxy)-benzoate (1.0 g of the TFA salt, 2.6 mmol) in DCM (10 ml). After shaking for 5 min cyclopropanesulfonyl chloride (0.54 g, 3.8 mmol) was added and the reaction mixture was shaken overnight at 20° C. After addition of silica gel (10 ml) the solvent was removed in vacuo, and flash chromatography (EtOAc/heptan 30:70 □ 50:50) gave 0.71 g of the desired sulfonamide.

Example 4

3-(6-Chloro-pyridin-3-ylmethoxy)-benzoic acid

NaH (55% suspension in mineral oil, 1.2 g, 28 mmol) was slowly added to a suspension of 2-chloro-5-chloromethylpyridine (3.0 g, 19 mmol), ethyl 3-hydroxybenzoate (3.1 g, 19 mmol), and potassium iodide (600 mg, 3.7 mmol) in DMF (20 ml). After stirring for 2 days at 20° C., water (10 ml) and NaOH (32.5%, 2 ml) was added. The dark mixture was stirred at 80° C. overnight, were upon it was concentrated in vacuo. The residue was purified by preparative LC-MS to give 0.80 g of the title compound. LC-MS (m/z): 264 (M+1).

The following compounds were prepared by a method similar to Example 4

3-(5-Chloro-pyridin-2-yloxy)-benzoic acid

Prepared from 2,5-dichloropyridine and ethyl 3-hydroxybenzoate. $^1$H NMR (400 MHz, DMSO-d$_6$) δ 13.17 (br. s., 1 H), 8.22 (d, 1 H), 8.00 (dd, 1 H), 7.81 (dd, 1 H), 7.60-7.64 (m, 1 H), 7.58 (t, 1 H), 7.43 (dd, 1 H), 7.18 (d, 1 H).

3-(6-Bromo-pyridin-3-yloxy)-benzoic acid

Prepared from 2-bromo-5-fluoropyridine and ethyl 3-hydroxybenzoate. $^1$H NMR (400 MHz, DMSO-d$_6$) δ 13.12 (br. s., 1 H), 8.28 (d, 1 H), 7.78 (d, 1 H), 7.69 (d, 1 H), 7.56 (t, 1 H), 7.48-7.54 (m, 2 H), 7.39 (dd, 1 H)

Example 5

4-Amino-1-hydroxyadamantane

Prepared as described in *Tetrahedron* 1968, 24, 5369

Example 6

(5-Hydroxyadamantan-2-yl)carbamic acid tert-butyl ester

Ammonium formate (10 g, 0.15 mol) was added to a solution of 5-hydroxyadamantan-2-one (4.5 g, 0.027 mol, prepared as described in *Tetrahedron* 1968, 24, 5369) in MeOH (50 ml). Then 10% Pd—C (500 mg) was added carefully and the solution heated under reflux for 1 h. It was then filtered through celite and to this filtrate at 0° C. was added triethylamine (11.2 ml, 0.081 mol) and Boc anhydride (7.06 g, 0.0324 mol). The solution was stirred for 4 h at 20° C. and then concentrated under reduced pressure. The residue was diluted with water and extracted with EtOAc. The organic layer was dried and concentrated to give (5-hydroxyadamantan-2-yl)carbamic acid tert-butyl ester (7 g, 96%). LC-MS (m/z): 168 (M+1). $^1$HNMR (300 MHz, DMSO-$d_6$): δ 6.8 (d, 1H), 6.7 (brs, 1H), 3.45 (d, 1H), 2.0 (s, 1H), 1.75-1.95 (m, 4H), 1.5-1.7 (m, 6H), 1.35 (s, 9H), 1.25 (t, 2H).

1-Hydroxy-4-methylamino-adamantane

Lithium aluminium hydride (0.711 g, 0.018 mol) was added to a solution of (5-hydroxy-adamantan-2-yl)carbamic acid tert-butyl ester (1 g, 0.0037 mol) in THF (50 ml) at 0° C. under a nitrogen atmosphere. The slurry was heated under reflux for 5 h. It was then cooled to 0° C. and quenched with 30% NaOH solution (12 ml) and filtered. The filtrate was concentrated to give 2-methylaminoadamantan-5-ol as a white solid (0.6 g, 90%). LC-MS (m/z): 181.9 (M+1). $^1$HNMR (300 MHz, DMSO-$d_6$): δ 4.3 (s, 1H), 4.2 (s, 1H), 2.4 (s, 0.7H), 2.3 (s, 0.3H), 2.2 (s, 3H), 1.8-2.0 (m, 5H), 1.5-1.6 (m, 5H), 1.4-1.5 (m, 2H), 1.2 (m, 2H).

Example 7

3-Oxo-8-azabicyclo[3.2.1]octane-8-carboxylic acid tert-butyl ester

Nortropinone (10 g, 0.062 mol) was dissolved in DCM (100 ml) and triethylamine (13.5 ml, 0.13 mol) was added followed by Boc anhydride (21.8 g, 0.10 mol). The reaction mixture was stirred at 20° C. for 3 h. It was then diluted with DCM (60 ml) and washed with 1N HCl, then twice with water and finally with brine. The organic layer was dried over anhydrous sodium sulphate and was concentrated under vacuum to give 15 g (86%) of 3-oxo-8-azabicyclo[3.2.1]octane-8-carboxylic acid tert-butyl ester. $^1$HNMR (300 MHz, DMSO-$d_6$): δ 4.2 (1H, s), 2.3 (2H, brs), 2.2 (2H, d), 2.0 (2H, brs), 1.6 (2H, d), 1.4 (9H, m).

3-Hydroxy-8-aza-bicyclo[3.2.1]octane-8-carboxylic acid tert-butyl ester

NaBH$_4$ (8.8 g, 0.23 mol) was added to a 0° C. solution of 3-oxo-8-azabicyclo[3.2.1]octane-8-carboxylic acid tert-butyl ester (35 g, 0.16 mol) in ethanol (200 ml). The reaction mixture was stirred for 45 min at 0° C., whereupon it was allowed to reach 20° C. After stirring overnight the suspension was evaporated to dryness. EtOAc (350 ml) was added, and the precipitate was filtered off. Water (200 ml) was added to the filtrate, and the layers were separated. The aqueous layer was extracted with EtOAc (100 ml) and the combined organic layers were dried (Na$_2$SO$_4$) and concentrated in vacuo to afford 29.5 g of an oil, which crystallised on standing. The two isomers were separated by flash chromatography (EtOAc/heptane 1:5 □ 1:1), affording 5 g of the title compound. LC-MS (m/z): 250 (M+23(Na)).

(1R,3S,5S)-8-Aza-bicyclo[3.2.1]octan-3-ol

HCl (conc. 10 ml) was added to a solution of 3-hydroxy-8-aza-bicyclo[3.2.1]octane-8-carboxylic acid tert-butyl ester (2.1 g, 9.2 mmol) in ethanol (30 ml). After stirring for 5 h the solvent was removed in vacuo to give 1.4 g of the title compound. LC-MS (m/z): 127 (M+1).

Example 8

3-Cyclohexylmethoxy-N-(5-hydroxy-adamantan-2-yl)-N-methyl-benzamide

3-Cyclohexylmethoxy-benzoic acid (300 mg, 1.3 mmol), HOBT (294 mg, 1.9 mmol), EDC (245 mg, 1.3 mmol), and 1-hydroxy-4-methylaminoadamantane (232 mg, 1.28 mmol) were suspended in DMF (2.5 ml) before DIPEA (0.44 ml, 2.6 mmol) was added. The reaction mixture was stirred at 20° C. overnight. The reaction mixture was purified directly by Preparative HPLC to give 199 mg of the title compound as a mixture of two isomers.

$^1$H NMR (400 MHz, CDCl$_3$) δ: 7.24-7.32 (m, 1 H), 6.88-6.98 (m, 3 H), 4.10-4.24 (m, 1 H), 3.76 (d, 1 H), 3.10 (s, 3 H), 2.51 (br. s., 2 H), 2.23 (br. s., 2 H), 1.63-2.02 (m, 14 H), 1.57 (d, 2 H), 1.16-1.36 (m, 3 H), 0.98-1.11 (m, 2 H).

The following compounds were prepared by a method similar to Example 8.

4-{2-[3-(5-Hydroxy-adamantan-2-ylcarbamoyl)-phenoxy]-ethyl}-piperidine-1-carboxylic acid isopropylamide Prepared from 3-[2-(1-isopropylcarbamoyl-piperidin-4-yl)-ethoxy]-benzoic acid and 4-amino-1-hydroxyadamantane. $^1$H NMR (400 MHz, CDCl$_3$): δ 7.31-7.37 (m, 2 H), 7.23-7.26 (m, 1 H), 7.04 (dd, 1 H), 6.37 (d, 1 H), 4.18-4.24 (m, 1 H), 4.06 (t, 2 H), 3.98 (septet, 1 H), 3.90 (d, 2 H), 2.82 (t, 2 H), 2.17-2.29 (m, 3 H), 1.92-1.99 (m, 2 H), 1.73-1.86 (m, 11 H), 1.59 (d, 2 H), 1.19-1.30 (m, 2 H), 1.16 (d, 6 H).

3-[2-(1-Cyclopropanesulfonyl-piperidin-4-yl)-ethoxy]-N-(5-hydroxy-adamantan-2-yl)-benzamide Prepared from 3-[2-(1-cyclopropanesulfonyl-piperidin-4-yl)-ethoxy]-benzoic acid and 4-amino-1-hydroxyadamantane. $^1$H NMR (400 MHz, CDCl$_3$): δ 7.32-7.38 (m, 2 H), 7.24-7.26 (m, 1 H), 7.03 (dd, 1 H), 6.32 (d, 1 H), 4.19-4.24 (m, 1 H), 4.07 (t, 2 H), 3.78-3.85 (m, 2 H), 2.81 (td, 2 H), 2.61 (br. s., 2 H), 2.22-2.29 (m, 3 H), 2.18-2.22 (m, 1 H), 1.95 (d, 2 H), 1.73-1.89 (m, 11 H), 1.65-1.73 (m, 1 H), 1.59 (d, 2 H), 1.41 (dd, 1 H), 1.35 (dd, 1 H), 1.14-1.20 (m, 2 H), 0.94-1.00 (m, 2 H).

3-(6-Chloro-pyridin-3-ylmethoxy)-N-(5-hydroxy-adamantan-2-yl)-benzamide

Prepared from 3-(6-chloro-pyridin-3-ylmethoxy)-benzoic acid and 4-amino-1-hydroxyadamantane. $^1$H NMR (400 MHz, CDCl$_3$): δ 8.49 (d, 1 H), 7.78 (dd, 1 H), 7.42-7.44 (m, 1 H), 7.38 (t, 2 H), 7.32 (d, 1 H), 7.10 (dd, 1 H), 6.32 (d, 1 H), 5.12 (s, 2 H), 4.19-4.24 (m, 1 H), 3.13 (br. s., 2 H), 2.26 (br. s., 2 H), 2.21 (br. s., 1 H), 1.95 (d, 2 H), 1.73-1.85 (m, 6 H), 1.59 (d, 2 H).

N-(5-Hydroxy-adamantan-2-yl)-3-(tetrahydro-pyran-4-ylmethoxy)-benzamide

Prepared from 3-(tetrahydro-pyran-4-ylmethoxy)-benzoic acid and 4-amino-1-hydroxyadamantane. LC-MS (m/z): 386 (M+1).

N-(5-Hydroxy-adamantan-2-yl)-3-[2-(tetrahydro-pyran-4-yl)-ethoxy]-benzamide

Prepared from 3-(tetrahydro-pyran-4-ylethoxy)-benzoic acid and 4-amino-1-hydroxyadamantane. LC-MS (m/z): 400 (M).

N-(5-Hydroxy-adamantan-2-yl)-3-[2-(2-oxo-pyrrolidin-1-yl)-ethoxy]-benzamide

Prepared from pyrrolidinoneethoxy-benzoic acid and 4-amino-1-hydroxyadamantane. LC-MS (m/z): 400 (M+1).

N-(5-Hydroxy-adamantan-2-yl)-N-methyl-3-(tetrahydro-pyran-4-yloxy)-benzamide Prepared from 3-(tetrahydro-pyran-4-yloxy)-benzoic acid and 1-hydroxy-4-methylaminoadamantane. LC-MS (m/z): 387 (M+2).

(3-Hydroxy-8-aza-bicyclo[3.2.1]oct-8-yl)-[3-(tetrahydro-pyran-4-ylmethoxy)-phenyl]-methanone Prepared from 3-(tetrahydro-pyran-4-yl-methoxy)-benzoic acid and 8-aza-bicyclo[3.2.1]octan-3-ol. LC-MS (m/z): 346 (M+1).

(3-Hydroxy-8-aza-bicyclo[3.2.1]oct-8-yl)-{3-[2-(tetrahydro-pyran-4-yl)-ethoxy]-phenyl}-methanone Prepared from 3-(tetrahydro-pyran-4-yl-ethoxy)-benzoic acid and 8-aza-bicyclo[3.2.1]octan-3-ol. LC-MS (m/z): 360 (M).

3-(4-Fluoro-benzyloxy)-N-(5-hydroxy-adamantan-2-yl)-benzamide

Prepared from 3-(4-fluoro-benzyloxy)-benzoic acid and 4-amino-1-hydroxyadamantane. LC-MS (m/z): 296 (M+1).

3-(5-Chloro-pyridin-2-yloxy)-N-(5-hydroxy-adamantan-2-yl)-benzamide

Prepared from 3-(5-chloro-pyridin-2-yloxy)-benzoic acid and 4-amino-1-hydroxyadamantane. $^1$H NMR (400 MHz, CDCl$_3$): δ 8.11 (s, 1 H), 7.68 (d, 1 H), 7.51-7.61 (m, 2 H), 7.47 (t, 1 H), 6.94 (d, 1 H), 6.23-6.36 (m, 1 H), 4.08-4.25 (m, 1 H), 2.24 (t, 3 H), 1.51-2.03 (m, 13 H).

3-(6-Bromo-pyridin-3-yloxy)-N-(5-hydroxy-adamantan-2-yl)-benzamide

Prepared from 3-(6-bromo-pyridin-3-yloxy)-benzoic acid and 4-amino-1-hydroxyadamantane. LC-MS (m/z): 444 (M+1).

(3-Hydroxy-8-aza-bicyclo[3.2.1]oct-8-yl)-[3-(4-hydroxy-cyclohexylmethoxy)-phenyl]-methanone Prepared from 3-[4-(tert-butyl-dimethyl-silanyloxy)-cyclohexylmethoxy]-benzoic acid and 8-Aza-bicyclo[3.2.1]octan-3-ol by a method similar to Example 8 followed by desilylation:

Desilylation

The partly desilylated product from the coupling reaction was dissolved in dry THF (20 ml), and after addition of TBAF (1.0 M in THF, 0.83 ml) the solution was allowed to stir overnight at 20° C. Addition of citric acid (5% in water, 25 ml) and extraction with EtOAc (3×25 ml), followed by drying (MgSO$_4$) and evaporation of the combined organic layers afforded the crude product. This was purified by preparative HPLC to give 170 mg of the title compound as a mixture of four isomers. $^1$H NMR (400 MHz, CDCl$_3$): δ 7.27-7.33 (m, 1 H), 6.93-7.03 (m, 3 H), 4.78-4.90 (m, 1 H), 4.03-4.24 (m, 2 H), 3.75-3.85 (m, 2 H), 2.81 (br. s., 4 H), 1.07-2.36 (m, 19 H).

Example 9

N-(5-Hydroxy-adamantan-2-yl)-N-methyl-3-phenethyloxy-benzamide

3-Phenethyloxy-benzoic acid (4.2 g, 17 mmol) was dissolved in thionylchloride (30 ml), and the mixture was stirred at 20° C. overnight. The solvent was removed, and 108 mg (0.41 mmol) of this acid chloride was added to a solution of 1-hydroxy-4-methylaminoadamantane (75 mg, 0.41 mmol) and DIPEA (0.14 ml, 0.83 mmol) in DCM/DMF (1:1, 4 ml). After stirring the reaction mixture at 20° C. overnight, the solution was concentrated in vacuo and purified by preparative LC-MS to give 95 mg of the title compound as a mixture of two isomers. $^1$H NMR (400 MHz, CDCl$_3$): δ 7.21-7.36 (m, 6 H), 6.89-7.00 (m, 3 H), 4.10-4.23 (m, 3 H), 3.05-3.16 (m, 5 H), 2.54 (d, 2 H), 2.24 (d, 1 H), 1.49-2.04 (m, 11 H).

The following compounds were prepared by a method similar to Example 9.

N-(5-Hydroxy-adamantan-2-yl)-3-phenethyloxy-benzamide

Prepared from 3-phenethyloxy-benzoic acid and 4-amino-1-hydroxyadamantane to give the title compound as a mixture of two isomers. $^1$H NMR (300 MHz, CDCl$_3$): δ 7.20-7.39 (m, 8 H), 7.13 (dd, 0.3 H), 7.02 (dd, 0.7 H), 6.22-6.38 (m, 1 H), 4.09-4.28 (m, 3 H), 3.11 (t, 2 H), 2.24 (t, 2 H), 1.47-2.00 (m, 9 H).

3-Benzyloxy-N-(5-hydroxy-adamantan-2-yl)-benzamide

Prepared from 3-(benzyloxy)benzoic acid and 4-amino-1-hydroxyadamantane to give the title compound as a mixture of two isomers. $^1$H NMR (300 MHz, CDCl$_3$): δ 7.69-7.74 (m, 1 H), 7.29-7.48 (m, 7 H), 7.20-7.24 (m, 0.5 H), 7.09-7.13 (m, 0.5 H), 6.27 (d, 1 H), 5.12 (s, 2 H), 4.18-4.23 (m, 1 H), 2.16-2.27 (m, 3 H), 1.91-1.98 (m, 2 H), 1.71-1.84 (m, 6 H), 1.54-1.61 (m, 2 H).

The compounds in examples 10-12 were prepared analogously as described above.

Examples 10

3-(6-Bromopyridin-3-yloxy)-N-(5-hydroxyadaman-tan-2-yl)benzamide

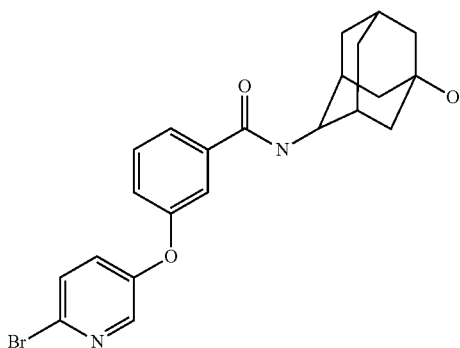 [SMILES: O=C(NC1C2CC3CC1CC(O)(C3)C2)c1cccc(Oc2ccc(Br)nc2)c1]

Example 11

4-Dimethylamino-N-(1,7,7-trimethylbicyclo[2.2.1]hept-2-yl)benzamide

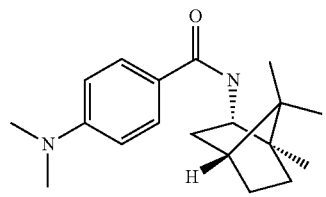

Example 12

4-Dimethylamino-N-(1,7,7-trimethylbicyclo[2.2.1]hept-2-yl)benzamide

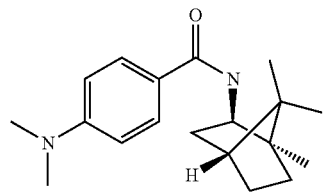

Pharmacological Methods
11βHSD1 Enzyme Assay
Materials

³H-cortisone and anti-rabbit Ig coated scintillation proximity assay (SPA) beads were purchased from Amersham Pharmacia Biotech, β-NADPH was from Sigma and rabbit anti-cortisol antibodies were from Fitzgerald. An extract of yeast transformed with h-11βHSD1 (Hutt et al., *FEBS Lett,* 441, 25 (1998)) was used as the source of enzyme. The test compounds were dissolved in DMSO (10 mM). All dilutions were performed in a buffer containing 50 mM TRIS-HCl (Sigma Chemical Co), 4 mM EDTA (Sigma Chemical Co), 0.1% BSA (Sigma Chemical Co), 0.01% Tween-20 (Sigma Chemical Co) and 0.005% bacitracin (Novo Nordisk A/S), pH=7.4. Optiplate 96 wells plates were supplied by Packard. The amount of ³H-cortisol bound to the SPA beads was measured on TopCount NXT, Packard.

Methods h-11βHSD1, 120 nM ³H-cortisone, 4 mM β-NADPH, antibody (1:200), serial dilutions of test compound and SPA particles (2 mg/well) were added to the wells. The reaction was initiated by mixing the different components and was allowed to proceed under shaking for 60 min at 30° C. The reaction was stopped be the addition of 10 fold excess of a stopping buffer containing 500 µM carbenoxolone and 1 µM cortisone. Data was analysed using GraphPad Prism software.

While the invention has been described and illustrated with reference to certain preferred embodiments thereof, those skilled in the art will appreciate that various changes, modifications, and substitutions can be made therein without departing from the spirit and scope of the present invention. For example, effective dosages other than the preferred dosages as set forth herein may be applicable as a consequence of variations in the responsiveness of the mammal being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Accordingly, the invention is not to be limited as by the appended claims.

The features disclosed in the foregoing description and/or in the claims may both separately and in any combination thereof be material for realising the invention in diverse forms thereof.

Preferred Features of the Invention:

1. A compound of the general formula (I):

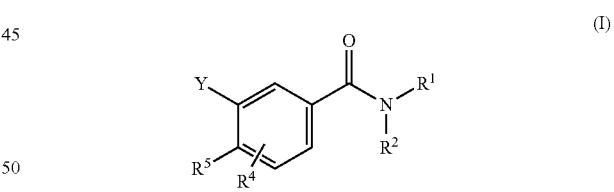

wherein $R^1$ is selected from the group consisting of hydrogen, methyl, ethyl, isopropyl and cyclopropyl and $R^2$ is selected from the group consisting of a monovalent radical having one of the following formulae, wherein the symbol * denotes the point of attachment:

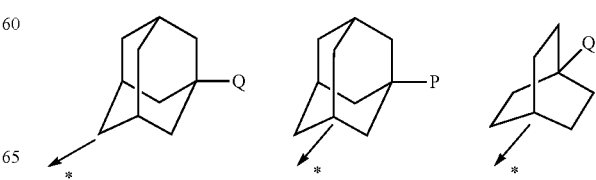

-continued

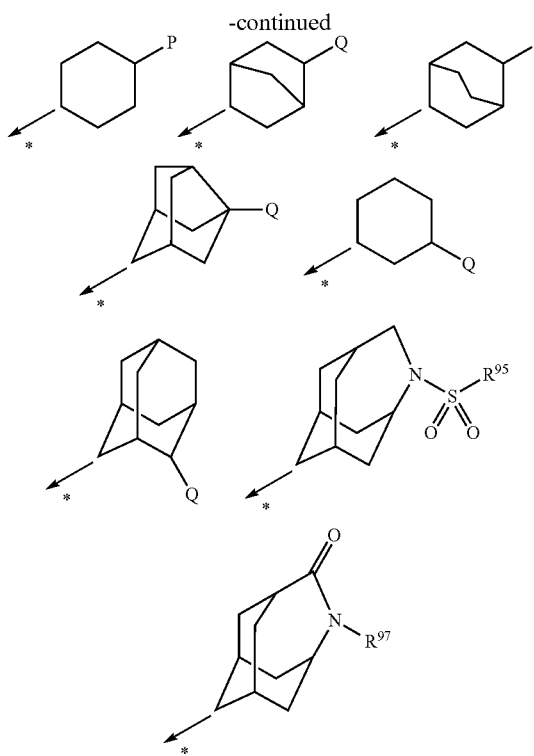

or R¹ and R² together with the nitrogen to which they are attached is selected from the group consisting of one of the following formulae wherein the symbol * denotes the point of attachment:

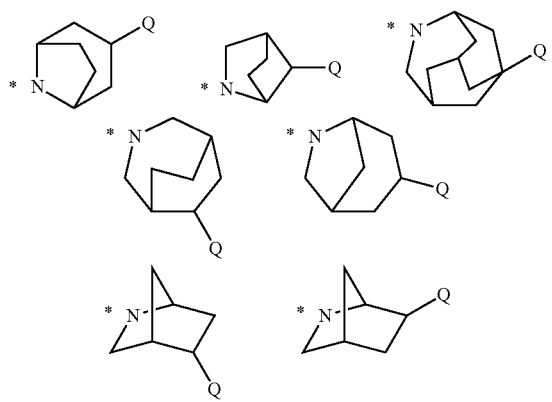

Q is selected is selected from the group consisting of hydroxy, carboxy, —S(=O)₂R⁶, and S(=O)₂NH₂;

P is selected from the group consisting of —S(=O)₂R⁶, carboxy and —S(=O)₂NH₂;

R⁶ is selected from the group consisting of $C_1$-$C_4$alkyl, phenyl, pyridine and $C_3$-$C_{10}$cycloalkyl, wherein said $C_1$-$C_4$alkyl, phenyl, pyridine and $C_3$-$C_{10}$cycloalkyl are optionally substituted with one or two independently selected R⁷;

R⁷ is selected from the group consisting of hydrogen, methyl, ethyl, cyclopropyl, —O—CH₃, —O-cyclopropyl, —O-isopropyl, hydroxy, and halogen, wherein said methyl, ethyl, cyclopropyl, —O—CH₃, —O-cyclopropyl and —O-isopropyl is optionally substituted with one substituent selected from the group consisting of hydroxy and halogen;

R⁴ is selected from the group consisting of hydrogen, $C_1$-$C_4$alkyl substituted with R¹² and R¹³, —O—($C_1$-$C_4$alkyl) substituted with R¹² and R¹³, trifluoromethyl, —CN, halogen, —S(=O)₂methyl, —S(=O)₂ethyl, —S(=O)₂cyclopropyl, —S(=O)₂NR¹⁰R¹¹ and —C(=O)NR¹⁰R¹¹;

R⁹⁵ is selected from the group consisting of $C_1$-$C_6$alkyl, phenyl, pyridine, pyrimidine, cyclopropyl, cyclobutyl and cyclohexyl, wherein said $C_1$-$C_6$alkyl, phenyl, pyridine, pyrimidine, cyclopropyl, cyclobutyl and cyclohexyl are optionally substituted with one or two independently selected R⁹⁶;

R⁹⁶ is selected from the group consisting of halogen, hydroxy, oxo, trifluoromethyl, $C_1$-$C_6$alkyl, and —S(=O)₂methyl;

R⁹⁷ is selected from the group consisting of hydrogen and $C_1$-$C_6$alkyl;

R¹² and R¹³ are each independently selected from the group consisting of hydrogen, —O—($C_1$-$C_4$alkyl), halogen, carboxy and hydroxy;

R⁵ is selected from the group consisting of hydrogen, $C_1$-$C_4$alkyl substituted with R¹⁶, trifluoromethyl, —CN, halogen, $C_1$-$C_4$alkylcarbonyl substituted with R¹⁸, —S(=O)₂R¹⁷, —S(=O)₂NR¹⁴R¹⁵, and —S—R¹⁷;

R¹⁰ and R¹¹ are each independently selected from the group consisting of hydrogen, and $C_1$-$C_4$alkyl; or R¹⁰ and R¹¹ together with the nitrogen to which they are attached form a 4 to 6 membered ring, wherein said $C_1$-$C_4$alkyl and each carbon atom in said 4 to 6 membered ring optionally is substituted with one or two substituents independently selected from the group consisting of hydroxy and halogen;

R¹⁴ and R¹⁵ are each independently selected from the group consisting of hydrogen, and $C_1$-$C_4$alkyl; or R¹⁴ and R¹⁵ together with the nitrogen to which they are attached form a 4 to 6 membered ring, wherein said $C_1$-$C_4$alkyl and each carbon atom in said 4 to 6 membered ring optionally is substituted with one or two substituents independently selected from the group consisting of hydroxy and halogen;

R¹⁶ and R¹⁸ are each independently selected from the group consisting of hydrogen, —O-methyl, methyl, cyclopropyl, halogen, —S(=O)₂-methyl, —S(=O)₂-ethyl, —C(=O)NH₂, —C(=O)N—CH₃CH₃, carboxy, and hydroxy;

R¹⁷ is selected from the group consisting of hydrogen and $C_1$-$C_6$alkyl, wherein said $C_1$-$C_6$alkyl is optionally substituted with one or two substituents selected from the group consisting of hydroxy and halogen;

Y is selected from the group consisting of —X¹—X²—X³—R³, —X¹⁰, —CR⁷²R⁷³—O—CR⁷⁰R⁷¹—R³, —CR⁷²R⁷³—S—CR⁷⁰R⁷¹—R³, —CR⁷²R⁷³—S(=O)₂—CR⁷⁰R⁷¹—R³, —CR⁷²R⁷³—NR²⁵—S(=O)₂—R³, —CR⁷²R⁷³—CR⁷⁰R⁷¹—S(=O)₂—R³, —CR⁷²R⁷³—CR⁷⁰R⁷¹—O—R³, —CR⁷²R⁷³—CR⁷⁰R⁷¹—S—R³, —CR⁷²R⁷³—CR⁷⁰R⁷¹—NR²⁵—R³, —O—CR⁴⁴R⁴⁵—S(=O)₂—R³, —CR⁷²R⁷³—O—R³, —CR⁷²R⁷³—S—R³, —CR⁷²R⁷³—S(=O)₂—R³, —CR⁷²R⁷³—NR²⁵—R³, —CR⁷²R⁷³—S(=O)₂—R³, —O—R¹⁰³, —O—CR⁴⁴R⁴⁵—R¹⁰³, —CR⁷²R⁷³—CR⁴⁴R⁴⁵—R¹⁰³, —O—CR⁴⁴R⁴⁵—CR⁷⁰R⁷¹—R¹⁰³, —CR⁷²R⁷³—CR⁴⁴R⁴⁵—CR⁷⁰R⁷¹—R¹⁰³, and —CH₂—R¹⁰³;

X¹ is selected from the group consisting of —S—, —S(=O)—, and —S(=O)₂—;

$X^2$ is absent or is selected from the group consisting of —O—, —$CR^{44}R^{45}$—, —S—, —S(=O)—, —S(=O)$_2$— and —$NR^{25}$—;

$X^3$ is absent or is selected from the group consisting of —O—, —$CR^{70}R^{71}$—, —S—, —S(=O)—, —S(=O)$_2$—, and —$NR^{125}$—;

$X^{10}$ is selected from the group consisting of $C_3$-$C_{10}$cycloalkyl substituted with $R^{19}$ and phenyl substituted with $R^{22}$;

each $R^{19}$ is independently selected from the group consisting of —CN, —C(=O)$R^{46}$, —CH(OH)—$R^{47}$, —$(CR^{44}R^{45})_m$—C(=O)—$NR^{48}R^{49}$, —$(CR^{44}R^{45})_m$—$OR^{49}$, —$(CR^{44}R^{45})_m$—$SR^{49}$, —$(CR^{44}R^{45})_m$—S(=O)$_2R^{50}$, —$(CR^{44}R^{45})_m$—S(=O)$_2NR^{48}R^{49}$, —$(CR^{44}R^{45})_m$—$NR^{48}$S(=O)$_2R^{50}$, —$(CR^{44}R^{45})_m$—$NR^{48}$C(=O)—$NR^{48}R^{49}$, —$(CR^{44}R^{45})_m$—C=C—$R^{51}R^{52}$, —$(CR^{44}R^{45})_m$—C≡C—$R^{53}$, —$(CR^{44}R^{45})_m$—$C_3$-$C_{10}$cycloalkyl substituted with $R^{55}$, and —$(CR^{44}R^{45})_m$-aryl substituted with $R^{56}$ and $R^{57}$.

each $R^{22}$ is independently selected from the group consisting of halogen, —CN, hydroxy, —C(=O)OH, —C(=O)$R^{46}$, —CH(OH)—$R^{47}$, hydroxy, —$(CR^{44}R^{45})_m$—C(=O)—$NR^{48}R^{49}$, —$(CR^{44}R^{45})_m$—$NR^{48}$C(=O)$R^{46}$, —$(CR^{44}R^{45})_m$—$OR^{49}$, —$(CR^{44}R^{45})_m$—$SR^{49}$, —$(CR^{44}R^{45})_m$—S(=O)$_2R^{50}$, —$(CR^{44}R^{45})_m$—S(=O)$_2NR^{48}R^{49}$, —$(CR^{44}R^{45})_m$—$NR^{48}$S(=O)$_2R^{50}$, —$(CR^{44}R^{45})_m$—$NR^{48}R^{49}$, —$(CR^{44}R^{45})_m$—$NR^{48}$C(=O)—$NR^{48}R^{49}$, —$(CR^{44}R^{45})_m$—C=C—$R^{51}R^{52}$, —$(CR^{44}R^{45})_m$—C≡C—$R^{53}$, —$(CR^{44}R^{45})_m$—$C_3$-$C_{10}$heterocyclyl substituted with $R^{54}$, —$(CR^{44}R^{45})_m$—$C_3$-$C_{10}$cycloalkyl substituted with $R^{55}$, —$(CR^{44}R^{45})_m$-aryl substituted with $R^{56}$ and $R^{57}$ and —$(CR^{44}R^{45})_m$-heteroaryl substituted with $R^{56}$ and $R^{57}$;

$R^{24}$ is selected from the group consisting of —C(=O)—$R^{26}$, —S(=O)$_2$—$R^{27}$, heteroaryl substituted with $R^{28}$, and aryl substituted with $R^{29}$;

$R^{25}$ is selected from the group consisting of hydrogen, methyl, ethyl, isobutyl, isopropyl and cyclopropyl;

$R^{125}$ is selected from the group consisting of hydrogen, methyl, ethyl, isobutyl, isopropyl and cyclopropyl;

$R^3$ is selected from the group consisting of $C_3$-$C_{10}$heterocyclyl substituted with $R^{30}$ and $R^{31}$, $C_3$-$C_{10}$cycloalkyl substituted with $R^{90}$ and $R^{91}$, aryl substituted with $R^{30}$ and $R^{31}$, heteroaryl substituted with $R^{90}$ and $R^{91}$, —C(=O)$R^{32}$, —CH(OH)—$R^{33}$, —$(CR^{44}R^{45})_n$—C(=O)—$NR^{34}R^{35}$, —$(CR^{44}R^{45})_n$—$NR^{36}$C(=O)$R^{37}$, —$(CR^{44}R^{45})_n$—$OR^{38}$, —$(CR^{44}R^{45})_n$—$SR^{38}$, —$(CR^{44}R^{45})_n$—S(=O)$_2R^{39}$, —$(CR^{44}R^{45})_n$—S(=O)$_2NR^{34}R^{35}$, —$(CR^{44}R^{45})_n$—$NR^{34}$S(=O)$_2$—$R^{40}$, —$(CR^{44}R^{45})_n$—$NR^{34}R^{35}$, —$(CR^{44}R^{45})_n$—$NR^{34}$C(=O)—$NR^{34}R^{35}$, —$(CR^{44}R^{45})_n$—C=C—$R^{41}R^{42}$, and —$(CR^{44}R^{45})_n$—C≡C—$R^{43}$, n is selected from the group consisting of 0, 1 and 2;

$R^{44}$ and $R^{45}$ are each independently selected from the group consisting hydrogen, halogen, $C_1$-$C_6$alkyl and $C_3$-$C_{10}$cycloalkyl, wherein said $C_1$-$C_6$alkyl and $C_3$-$C_{10}$cycloalkyl are optionally substituted with one or two substituents selected independently from the group consisting halogen, hydroxy and oxo; or $R^{44}$ and $R^{45}$ together with the carbon atom to which they are attached form a cyclopropyl or cyclobutyl ring, wherein said ring are optionally substituted with hydroxy or halogen;

$R^{70}$ and $R^{71}$ are each independently selected from the group consisting hydrogen, halogen, $C_1$-$C_6$alkyl and $C_3$-$C_{10}$cycloalkyl, wherein said $C_1$-$C_6$alkyl and $C_3$-$C_{10}$cycloalkyl are optionally substituted with one or two substituents selected independently from the group consisting halogen, hydroxy and oxo; or $R^{44}$ and $R^{45}$ together with the carbon atom to which they are attached form a cyclopropyl or cyclobutyl ring, wherein said ring are optionally substituted with hydroxy or halogen;

$R^{72}$ and $R^{73}$ are each independently selected from the group consisting hydrogen, halogen, $C_1$-$C_6$alkyl and $C_3$-$C_{10}$cycloalkyl, wherein said $C_1$-$C_6$alkyl and $C_3$-$C_{10}$cycloalkyl are optionally substituted with one or two substituents selected independently from the group consisting halogen, hydroxy and oxo; or $R^{44}$ and $R^{45}$ together with the carbon atom to which they are attached form a cyclopropyl or cyclobutyl ring, wherein said ring are optionally substituted with hydroxy or halogen;

$R^{30}$, $R^{31}$, $R^{42}$ and $R^{43}$ are each independently selected from the group consisting of hydrogen, halogen, —CN, —C(=O)OH, —C(=O)$R^{46}$, —CH(OH)—$R^{47}$, trifluoromethyl, hydroxy, —$(CR^{44}R^{45})_m$—C(=O)—$NR^{48}R^{49}$, —$(CR^{44}R^{45})_m$—$NR^{48}$C(=O)$R^{46}$, —$(CR^{44}R^{45})_m$—$OR^{49}$, —$(CR^{44}R^{45})_m$—$SR^{49}$, —$(CR^{44}—R^{45})_m$—S(=O)$_2R^{59}$, —$(CR^{44}R^{45})_m$—S(=O)$_2NR^{48}R^{49}$, —$(CR^{44}R^{45})_m$—$NR^{48}$S(=O)$_2R^{59}$, —$(CR^{44}R^{45})_m$—$NR^{48}R^{49}$, —$(CR^{44}R^{45})_m$—$NR^{48}$C(=O)—$NR^{48}R^{49}$, —$(CR^{44}R^{45})_m$—C=$CR^{51}R^{52}$, —$(CR^{44}R^{45})_m$—C≡C—$R^{53}$, —$(CR^{44}R^{45})_m$—$C_3$-$C_{10}$heterocyclyl substituted with $R^{54}$, —$(CR^{44}R^{45})_m$—$C_3$-$C_{10}$cycloalkyl substituted with $R^{55}$, —$(CR^{44}R^{45})_m$-aryl substituted with $R^{56}$ and $R^{57}$ and —$(CR^{44}R^{45})_m$-heteroaryl substituted with $R^{56}$ and $R^{57}$;

$R^{90}$ and $R^{91}$ are each independently selected from the group consisting of hydrogen, halogen, =O, —CN, —C(=O)OH, —C(=O)$R^{46}$, —CH(OH)—$R^{47}$, hydroxy, trifluoromethyl, —$(CR^{44}R^{45})_m$—C(=O)—$NR^{48}R^{49}$, —$(CR^{44}R^{45})_m$—$NR^{48}$C(=O)$R^{46}$, —$(CR^{44}R^{45})_m$—$OR^{49}$, —$(CR^{44}R^{45})_m$—$SR^{49}$, —$(CR^{44}R^{45})_m$—S(=O)$_2R^{59}$, —$(CR^{44}R^{45})_m$—S(=O)$_2NR^{48}R^{49}$, —$(CR^{44}R^{45})_m$—$NR^{48}$S(=O)$_2R^{59}$, —$(CR^{44}R^{45})_m$—$NR^{48}R^{49}$, —$(CR^{44}R^{45})_m$—$NR^{48}$C(=O)—$NR^{48}R^{49}$, —$(CR^{44}R^{45})_m$—C=$CR^{51}R^{52}$, —$(CR^{44}R^{45})_m$—C≡C—$R^{53}$, —$(CR^{44}R^{45})_m$—$C_3$-$C_{10}$heterocyclyl substituted with $R^{54}$, —$(CR^{44}R^{45})_m$—$C_3$-$C_{10}$cycloalkyl substituted with $R^{55}$, —$(CR^{44}R^{45})_m$-aryl substituted with $R^{56}$ and $R^{57}$ and —$(CR^{44}R^{45})_m$-heteroaryl substituted with $R^{56}$ and $R^{57}$;

m is 0 or 1;

$R^{32}$, $R^{33}$, $R^{37}$, $R^{38}$, $R^{39}$, $R^{40}$ and $R^{41}$ are each independently selected from the group consisting of hydrogen, $C_1$-$C_6$alkyl, $C_3$-$C_{10}$heterocyclyl, $C_3$-$C_{10}$cycloalkyl, aryl and heteroaryl, wherein said $C_1$-$C_6$alkyl, $C_3$-$C_{10}$heterocyclyl, $C_3$-$C_{10}$cycloalkyl, aryl and heteroaryl are optionally substituted with one, two or three independently selected $R^{58}$;

$R^{34}$, $R^{35}$, and $R^{36}$ are each independently selected from the group consisting of hydrogen, $C_1$-$C_6$alkyl, $C_3$-$C_{10}$cycloalkyl and heteroaryl, wherein said $C_1$-$C_6$alkyl, $C_3$-$C_{10}$cycloalkyl and heteroaryl are optionally substituted with one, two or three substituents independently selected from the group consisting of halogen, methyl, ethyl and hydroxy; or $R^{34}$ and $R^{35}$ together with the nitrogen to which they are attached form a 4 to 6 membered ring, wherein said 4 to 6 membered ring optionally is substituted with one or two substituents independently selected from the group consisting of hydroxy or halogen;

$R^{26}$, $R^{27}$, $R^{46}$, $R^{47}$, $R^{49}$, $R^{50}$, $R^{51}$, $R^{52}$ and $R^{53}$ are each independently selected from the group consisting of hydrogen, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy;

$R^{54}$, $R^{55}$, $R^{56}$ and $R^{57}$ are each independently selected from the group consisting of hydrogen, halogen, —CN, trifluoromethyl, —OCH$_2$CH$_2$OH, hydroxyl, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy;

$R^{48}$ and $R^{49}$ are each independently selected from the group consisting of hydrogen, $C_1$-$C_6$alkyl, tetrahydropyrane, cyclohexyl and cyclopentyl, wherein said $C_1$-$C_6$alkyl, tetrahydropyrane, cyclohexyl and cyclopentyl are optionally substituted with one or two substituents independently selected from the group consisting of halogen and hydroxy; or $R^{48}$ and $R^{49}$ together with the nitrogen to which they are attached form a 4 to 6 membered ring, wherein said 4 to 6 membered ring optionally is substituted with one or two substituents independently selected from the group consisting of hydroxy and halogen;

$R^{58}$ are each independently selected from the group consisting of halogen, —CN, hydroxy, oxo, —C(=O)OH, —S(=O)$_2$R$^{59}$, —S—NR$^{60}$R$^{61}$, S(=O)$_2$NR$^{60}$R$^{61}$, cyclopropyl, —OR$^{59}$, —SR$^{59}$, $C_1$-$C_6$alkyl, —C(=O)NR$^{60}$R$^{61}$, —NR$^{60}$C(=O)NR$^{61}$R$^{60}$, —NR$^{60}$S(=O)$_2$R$^{59}$ and —NC(=O)R$^{59}$;

$R^{59}$ is selected from the group consisting of hydrogen, $C_1$-$C_6$alkyl, $C_3$-$C_{10}$cycloalkyl, aryl and heteroaryl, wherein said $C_1$-$C_6$alkyl, $C_3$-$C_{10}$cycloalkyl, aryl and heteroaryl are optionally substituted with one, two or three substituents independently selected from the group consisting of halogen, methyl, ethyl, methoxy, ethoxy, trifluoromethyl, —CN and hydroxy;

$R^{60}$ and $R^{61}$ are each independently selected from the group consisting of hydrogen, $C_1$-$C_6$alkyl, $C_3$-$C_{10}$heterocyclyl, $C_3$-$C_{10}$cycloalkyl and heteroaryl, wherein said $C_1$-$C_6$alkyl, $C_3$-$C_{10}$heterocyclyl, $C_3$-$C_{10}$cycloalkyl and heteroaryl are optionally substituted with one or two substituents independently selected from the group consisting of halogen and hydroxy; or $R^{60}$ and $R^{61}$ together with the nitrogen to which they are attached form a 4 to 6 membered ring, wherein said 4 to 6 membered ring optionally is substituted with one or two substituents independently selected from the group consisting of hydroxy and halogen;

$R^{103}$ is selected from the group consisting of $C_3$-$C_{10}$heterocyclyl substituted with two substituents independently selected from the group consisting of $R^{62}$ and $R^{63}$, $C_3$-$C_{10}$cycloalkyl substituted with $R^{30}$ and $R^{31}$, aryl substituted with $R^{30}$ and $R^{31}$, heteroaryl substituted with two substituents independently selected from the group consisting of $R^{62}$ and $R^{63}$, —C(=O)R$^{93}$, —CH(OH)—R$^{33}$, —C(=O)—NR$^{94}$R$^{95}$, —NR$^{36}$C(=O)R$^{37}$, —OR$^{35}$, —SR$^{35}$, —S(=O)$_2$R$^{39}$, —S(=O)$_2$NR$^{34}$R$^{35}$, —NR$^{34}$S(=O)$_2$—R$^{40}$, —NR$^{24}$R$^{25}$—, —NR$^{34}$C(=O)—NR$^{34}$R$^{35}$, —C≡C substituted with $R^{41}$ and $R^{42}$, W and —C≡C substituted with $R^{43}$;

W is selected from the group consisting of pyrrolidinone, tetrahydropyrane, 1,4-dioxane, aziridinone, azetidinone, piperidinone, thiazole, imidazole, tetrahydrofurane and oxepane;

$R^{93}$ is selected from the group consisting of hydrogen, $C_3$-$C_{10}$heterocyclyl, $C_3$-$C_{10}$cycloalkyl, aryl and heteroaryl, wherein said $C_3$-$C_{10}$heterocyclyl, $C_3$-$C_{10}$cycloalkyl, aryl and heteroaryl are optionally substituted with one, two or three independently selected $R^{58}$;

$R^{94}$ and $R^{95}$ are each independently selected from the group consisting of hydrogen, $C_3$-$C_{10}$cycloalkyl and heteroaryl, wherein said $C_3$-$C_{10}$cycloalkyl and heteroaryl are optionally substituted with one, two or three substituents independently selected from the group consisting of halogen, methyl, ethyl and hydroxy; or $R^{94}$ and $R^{95}$ together with the nitrogen to which they are attached form a 4 to 6 membered ring, wherein said 4 to 6 membered ring optionally is substituted with one or two substituents independently selected from the group consisting of hydroxy or halogen;

$R^{62}$ is selected from the group consisting of halogen, —C(=O)OH, —CH(OH)—R$^{47}$, —C(=O)—NR$^{48}$R$^{49}$, —NR$^{48}$C(=O)R$^{46}$, —SR$^{49}$, —S(=O)$_2$R$^{50}$, —S(=O)$_2$NR$^{48}$R$^{49}$, —NR$^{45}$S(=O)$_2$R$^{50}$, —NR$^{45}$C(=O)—NR$^{48}$R$^{49}$, —C=C—R$^{51}$R$^{52}$, —C≡C—R$^{53}$, CH$_2$CH$_2$OH, —CH$_2$CH$_2$OH, $C_3$-$C_{10}$heterocyclyl substituted with $R^{54}$, $C_3$-$C_{10}$cycloalkyl substituted with $R^{55}$, aryl substituted with $R^{56}$ and $R^{57}$ and heteroaryl substituted with $R^{56}$ and $R^{57}$;

$R^{63}$ is selected from the group consisting of hydrogen, =O, halogen, hydroxy, trifluoromethyl, —CN, oxo, —C(=O)OH, —S(=O)$_2$R$^{59}$, —S(=O)$_2$NR$^{60}$R$^{61}$, —S(=O)NR$^{60}$R$^{61}$ cyclopropyl, —OR$^{59}$, —SR$^{59}$, $C_1$-$C_6$alkyl, —C(=O)NR$^{60}$R$^{61}$, —NR$^{60}$C(=O)NR$^{61}$R$^{60}$; —NR$^{60}$S(=O)$_2$R$^{59}$, and —N(C=O)R$^{59}$;

a salt thereof with a pharmaceutically acceptable acid or base, or any optical isomer or mixture of optical isomers, including a racemic mixture, or any tautomeric forms.

2. The compound according to clause 1, wherein Y is —X$^1$—X$^2$—X$^3$—R$^3$.

3. The compound according to clause 2, wherein X$^1$ is selected from the group consisting of —S— and —S(=O)$_2$—.

4. The compound according to clause 3, wherein X$^1$ is —S(=O)$_2$—.

5. The compound according to any one of clauses 2-4, wherein X$^2$ is absent or is selected from the group consisting of —CR$^{44}$R$^{45}$— and —NR$^{25}$—.

6. The compound according to clause 5, wherein X$^2$ is absent or is —CR$^{44}$R$^{45}$.

7. The compound according to any one of clauses 2-6, wherein X$^3$ is absent or is —CR$^{70}$R$^{71}$—.

8. The compound according to any one of clauses 2-7, wherein —X$^1$—X$^2$—X$^3$—R$^3$ is selected from the group consisting of —S—R$^3$, —S(=O)$_2$—R$^3$, —S(=O)$_2$—NR$^{25}$R$^3$, —S(=O)$_2$—CR$^{44}$R$^{45}$—R$^3$.

9. The compound according to clause 8, wherein —X$^1$—X$^2$—X$^3$—R$^3$ is selected from the group consisting of —S—R$^3$, —S(=O)$_2$—R$^3$.

10. The compound according to clause 8, wherein —X$^1$—X$^2$—X$^3$—R$^3$ is selected from the group consisting of —S(=O)$_2$—NR$^{25}$R$^3$, —S(=O)$_2$—CR$^{44}$R$^{45}$—R$^3$.

11. The compound according to clause 1, wherein Y is selected from the group consisting of —CR$^{72}$R$^{73}$—O—CR$^{70}$R$^{71}$—R$^3$, —CR$^{72}$R$^{73}$—S—CR$^{70}$R$^{71}$—R$^3$, —CR$^{72}$R$^{73}$—S(=O)$_2$—CR$^{70}$R$^{71}$—R$^3$, —CR$^{72}$R$^{73}$—NR$^{25}$—S(=O)$_2$—R$^3$, —CR$^{72}$R$^{73}$—CR$^{70}$R$^{71}$—S(=O)$_2$—R$^3$, —CR$^{72}$R$^{73}$—CR$^{70}$R$^{71}$—O—R$^3$, —CR$^{72}$R$^{73}$—CR$^{70}$R$^{71}$—S—R$^3$, —CR$^{72}$R$^{73}$—CR$^{70}$R$^{71}$—NR$^{25}$—R$^3$, —O—CR$^{44}$R$^{45}$—S(=O)$_2$—R$^3$, —CR$^{72}$R$^{73}$—O—R$^3$, —CR$^{72}$R$^{73}$—S—R$^3$, —CR$^{72}$R$^{73}$—S(=O)$_2$—R$^3$, —CR$^{72}$R$^{73}$—NR$^{25}$—R$^3$, —CR$^{72}$R$^{73}$—S(=O)$_2$—R$^3$, —O—R$^{103}$, —O—CR$^{44}$R$^{45}$—R$^{103}$, —CR$^{72}$R$^{73}$—CR$^{44}$R$^{45}$—R$^{103}$, —O—CR$^{44}$R$^{45}$—COR$^{71}$—R$^{103}$, —CR$^{72}$R$^{73}$—CR$^{44}$R$^{45}$—COR$^{71}$—R$^{103}$, and —CR$^{72}$R$^{73}$—R$^{103}$.

12. The compound according to clause 11, wherein Y is selected from the group consisting of —CR$^{72}$R$^{73}$—O—CR$^{70}$R$^{71}$—R$^3$, —CR$^{72}$R$^{73}$—S—CR$^{70}$R$^{71}$—R$^3$, —CR$^{72}$R$^{73}$—S(=O)$_2$—CR$^{70}$R$^{71}$—R$^3$, —CR$^{72}$R$^{73}$—

$NR^{25}-S(=O)_2-R^3$, $-CR^{72}R^{73}-CR^{70}R^{71}-S(=O)_2-R^3$, $-CR^{72}R^{73}-CR^{70}R^{71}-O-R^3$ and $-CR^{72}R^{73}-CR^{70}R^{71}-NR^{25}-R^3$.

13. The compound according to clause 12, wherein Y is selected from the group consisting of $-CR^{72}R^{73}-O-CR^{70}R^{71}-R^3$, $-CR^{72}R^{73}-S-CR^{70}R^{71}-R^3$, $-CR^{72}R^{73}-CR^{70}R^{71}-O-R^3$ and $-CR^{72}R^{73}-CR^{70}R^{71}-NR^{25}-R^3$.

14. The compound according to clause 11, wherein Y is selected from the group consisting of $-CR^{72}R^{73}-S(=O)_2-CR^{70}R^{71}-R^3$, $-CR^{72}R^{73}-CR^{70}R^{71}-S(=O)_2-R^3$ and $-CR^{72}R^{73}-NR^{25}-S(=O)_2-R^3$.

15. The compound according to clause 11, wherein Y is selected from the group consisting of $-CR^{72}R^{73}-O-CR^{70}R^{71}-R^3$, $-CR^{72}R^{73}-CR^{70}R^{71}-O-R^3$ and $-CR^{72}R^{73}-CR^{70}R^{71}-NR^{28}-R^3$.

16. The compound according to clause 1, wherein Y is selected from the group consisting of $C_3$-$C_{10}$cycloalkyl substituted with $R^{19}$ and phenyl substituted with $R^{22}$.

17. The compound according to clause 16, wherein Y is $C_3$-$C_{10}$cycloalkyl substituted with $R^{19}$.

18. The compound according to clause 16, wherein Y is phenyl substituted with $R^{22}$.

19. The compound according to any one of clauses 1-15, wherein $R^3$ is selected from the group consisting of $C_3$-$C_{10}$heterocyclyl substituted with $R^{30}$ and $R^{31}$, $C_3$-$C_{10}$cycloalkyl substituted with $R^{90}$ and $R^{91}$, aryl substituted with $R^{30}$ and $R^{31}$, heteroaryl substituted with $R^{90}$ and $R^{91}$.

20. The compound according to any one of clauses 1-15, wherein $R^3$ is selected from the group consisting of $-C(=O)R^{32}$, $-CH(OH)-R^{33}$, $-(CR^{44}R^{45})C(=O)-NR^{34}R^{35}$, $-(CR^{44}R^{45})_n-NR^{36}C(=O)R^{37}$, $-(CR^{44}R^{45})_n-OR^{38}$, $-(CR^{44}R^{45})_n-SR^{38}$, $-(CR^{44}R^{45})_n-S(=O)_2R^{39}$, $-(CR^{44}R^{45})_n-S(=O)_2NR^{34}R^{35}$, $-(CR^{44}R^{45})_n-NR^{34}S(=O)_2-R^{40}$, $-(CR^{44}R^{45})_n-NR^{34}R^{35}$, $-(CR^{44}R^{45})_n-NR^{34}C(=O)-NR^{34}R^{35}$, $-(CR^{44}R^{45})_n-C=C-R^{41}R^{42}$ and $-(CR^{44}R^{45})_n-C\equiv C-R^{43}$.

21. The compound according to any one of clauses 1-15, wherein $R^3$ is selected from the group consisting of $C_3$-$C_{10}$heterocyclyl substituted with $R^{30}$, $C_3$-$C_{10}$cycloalkyl substituted with $R^{90}$, aryl substituted with $R^{30}$, heteroaryl substituted with $R^{90}$, $-(CR^{44}R^{45})_n-C(=O)-NR^{34}R^{35}$, $-(CR^{44}R^{45})_n-NR^{36}C(=O)R^{37}$, $-(CR^{44}R^{45})_n-OR^{38}$, $-(CR^{44}R^{45})_n-S(=O)_2R^{39}$, $-(CR^{44}R^{45})_n-S(=O)_2NR^{34}R^{35}$, $-(CR^{44}R^{45})_n-NR^{34}S(=O)_2-R^{40}$, $-(CR^{44}R^{45})_n-NR^{34}C(=O)-NR^{34}R^{35}$, $-(CR^{44}R^{45})_n-C=CR^{41}R^{42}$ and $-(CR^{44}R^{45})_n-C\equiv C-R^{43}$.

22. The compound according to any one of clauses 1-15, wherein $R^3$ is selected from the group consisting of $C_3$-$C_{10}$heterocyclyl substituted with $R^{30}$, $C_3$-$C_{10}$cycloalkyl substituted with $R^{90}$, aryl substituted with $R^{30}$; heteroaryl substituted with $R^{90}$, $-C(=O)-NR^{34}R^{35}$, $-NR^{36}C(=O)R^{37}$, $-OR^{38}$, $-S(=O)_2R^{39}$, $-S(=O)_2NR^{34}R^{35}$, $-NR^{34}S(=O)_2-R^{40}$, $-NR^{34}C(=O)-NR^{34}R^{35}$, $-C=CR^{41}R^{42}$ and $-C\equiv C-R^{43}$.

23. The compound according to any one of clauses 1-15, wherein $R^3$ is selected from the group consisting of $C_3$-$C_{10}$heterocyclyl substituted with $R^{30}$, $C_3$-$C_{10}$cycloalkyl substituted with $R^{90}$, heteroaryl substituted with $R^{30}$, $-C(=O)-NR^{34}R^{35}$, $-NR^{36}C(=O)R^{37}$, $-OR^{38}$, $-S(=O)_2R^{39}$, $-S(=O)_2NR^{34}R^{35}$, $-NR^{34}S(=O)_2-R^{40}$, $-NR^{34}C(=O)-NR^{34}R^{35}$, $-C=CR^{41}R^{42}$ and $-C\equiv C-R^{43}$.

24. The compound according to any one of clauses 1-15, wherein $R^3$ is selected from the group consisting of piperidine substituted with $R^{30}$, pyrrolidine substituted with $R^{30}$, morpholine substituted with $R^{30}$, tetrahydropyranyl substituted with $R^{30}$, cyclohexyl substituted with $R^{30}$, cyclopropyl substituted with $R^{30}$, cyclobutyl substituted with $R^{30}$, cyclopentyl substituted with $R^{30}$, phenyl substituted with $R^{30}$; pyridazinyl substituted with $R^{30}$, pyrazinyl substituted with $R^{30}$, pyridine substituted with $R^{30}$, imidazolyl substituted with $R^{30}$, pyrazolyl substituted with $R^{30}$ and pyrimidinyl substituted with $R^{30}$, isoxazolyl substituted with $R^{30}$, pyridinyl substituted with $R^{30}$, $-C(=O)-NR^{34}R^{35}$, $-NR^{36}C(=O)R^{37}$, $-OR^{38}$, $-S(=O)_2R^{39}$, $-S(=O)_2NR^{34}R^{35}$, $-NR^{34}S(=O)_2-R^{40}$, $-NR^{34}C(=O)-NR^{34}R^{35}$ and $-C\equiv C-R^{43}$.

25. The compound according to any one clauses 1-15, wherein $R^3$ is selected from the group consisting of piperidine substituted with $R^{30}$, pyrrolidine substituted with $R^{30}$, morpholine substituted with $R^{30}$, tetrahydropyranyl substituted with $R^{30}$, cyclohexyl substituted with $R^{30}$, cyclopropyl substituted with $R^{30}$, cyclobutyl substituted with $R^{30}$, cyclopentyl substituted with $R^{30}$, phenyl substituted with $R^{30}$; pyridazinyl substituted with $R^{30}$, pyrazinyl substituted with $R^{30}$, pyridine substituted with $R^{30}$, imidazolyl substituted with $R^{30}$, pyrazolyl substituted with $R^{30}$ and pyrimidinyl substituted with $R^{30}$, isoxazolyl substituted with $R^{30}$, pyridinyl substituted with $R^{30}$.

26. The compound according to any one of clauses 1-15, wherein $R^3$ is selected from the group consisting of $-NR^{36}C(=O)R^{37}$, $-NR^{34}S(=O)_2-R^{40}$ and $-NR^{34}C(=O)-NR^{34}R^{35}$.

27. The compound according to any one of clauses 1-15, wherein $R^3$ is selected from the group consisting of $-C(=O)-NR^{34}R^{35}$, $-OR^{38}$, $-S(=O)_2R^{39}$, $-S(=O)_2NR^{34}R^{35}$ and $-C\equiv C-R^{43}$.

28. The compound according to any one of clauses 1-15, wherein n is selected from the group consisting of 0 or 1.

29. The compound according to clause 28, wherein n is 0.

30. The compound according to clause 11, wherein $R^{103}$ is selected from the group consisting of $-C(=O)R^{93}$, $-CH(OH)-R^{33}$, $-C(=O)-NR^{94}R^{95}$, $-NR^{36}C(=O)R^{37}$, $-OR^{38}$, $-SR^{38}$, $-S(=O)_2R^{39}$, $-S(=O)_2NR^{34}R^{35}$, $-NR^{34}S(=O)_2-R^{40}$, $-NR^{24}R^{25}-$, $-NR^{34}C(=O)-NR^{34}R^{35}$, $-C=C$ substituted with $R^{41}$ and $R^{42}$, W and $-C\equiv C$ substituted with $R^{43}$.

31. The compound according to clause 11, wherein $R^{103}$ is selected from the group consisting of $C_3$-$C_{10}$heterocyclyl substituted with two substitutions independently selected from the group consisting of $R^{62}$ and $R^{63}$, $C_3$-$C_{10}$cycloalkyl substituted with $R^{30}$ and $R^{31}$, aryl substituted with $R^{30}$ and $R^{31}$, heteroaryl substituted with two substitutions independently selected from the group consisting of $R^{62}$ and $R^{63}$.

32. The compound according to clause 11, wherein $R^{103}$ is selected from the group consisting of $C_3$-$C_{10}$heterocyclyl substituted with two substitutions independently selected from the group consisting of $R^{62}$ and $R^{63}$ and heteroaryl substituted with two substitutions independently selected from the group consisting of $R^{62}$ and $R^{63}$.

33. The compound according to clause 11, wherein $R^{103}$ is selected from the group consisting of cyclopropyl, cyclobutyl, cyclohexyl and cyclopentyl substituted with $R^{30}$ and $R^{31}$ and phenyl substituted with $R^{30}$ and $R^{31}$, tetrahydropyranyl, piperidinyl, pyrrolidinyl and morpholinyl substituted with two substitutions independently selected from the group consisting of $R^{62}$ and $R^{63}$ and imidazolyl, pyrazolyl, isoxazolyl, pyridazinyl, pyrazinyl pyrimidinyl and pyridinyl substituted with two substitutions independently selected from the group consisting of $R^{62}$ and $R^{63}$.

34. The compound according to clause 11, wherein $R^{103}$ is selected from the group consisting of tetrahydropyranyl, piperidinyl, pyrrolidinyl and morpholinyl substituted with two substitutions independently selected from the group consisting of $R^{62}$ and $R^{63}$ and imidazolyl, pyrazolyl, isoxazolyl, pyridazinyl, pyrazinyl pyrimidinyl and pyridinyl substituted with one or two substitutions independently selected from the group consisting of $R^{62}$ and $R^{63}$.

35. The compound according to any one of clauses 31-34, wherein $R^{103}$ comprises at least one $R^{62}$ group.

36. The compound according to clause 11, wherein $R^{103}$ is selected from the group consisting of $C_3$-$C_{10}$cycloalkyl substituted with $R^{30}$ and $R^{31}$ and aryl substituted with $R^{30}$ and $R^{31}$;

37. The compound according to clause 11, wherein $R^{103}$ is selected from the group consisting of cyclopropyl, cyclobutyl, cyclohexyl, phenyl and cyclopentyl substituted with $R^{30}$ and $R^{31}$;

38. The compound according to clause 11, wherein $R^{103}$ is selected from the group consisting of —C(=O)—NR$^{94}$R$^{95}$, —NR$^{36}$C(=O)R$^{37}$, —OR$^{38}$, —SR$^{38}$, —S(=O)$_2$R$^{39}$, —S(=O)$_2$NR$^{34}$R$^{35}$, —NR$^{34}$S(=O)$_2$—R$^{40}$, —NR$^{34}$C(=O)—NR$^{34}$R$^{35}$, W and —C≡C substituted with $R^{43}$.

39. The compound according to clause 11, wherein $R^{103}$ is selected from the group consisting of —C(=O)—NR$^{94}$R$^{95}$, —NR$^{36}$C(=O)R$^{37}$, —OR$^{38}$, —S(=O)$_2$R$^{39}$, —S(=O)$_2$NR$^{34}$R$^{35}$, —NR$^{34}$S(=O)$_2$—R$^{40}$, —NR$^{34}$C(=O)—NR$^{34}$R$^{35}$ and W.

40. The compound according to clause 11, wherein $R^{103}$ is selected from the group consisting of —NR$^{36}$C(=O)R$^{37}$, —NR$^{34}$S(=O)$_2$—R$^{40}$ and —NR$^{34}$C(=O)—NR$^{34}$R$^{35}$.

41. The compound according to clause 11, wherein $R^{103}$ is selected from the group consisting of —C(=O)—NR$^{94}$R$^{95}$, —OR$^{38}$, —S(=O)$_2$R$^{39}$, —S(=O)$_2$NR$^{34}$R$^{35}$ and W.

42. The compound according to clause 11, wherein $R^{103}$ is W selected from the group consisting of pyrrolidinone, tetrahydropyrane, 1,4-dioxane, piperidinone, thiazole, imidazole and tetrahydrofurane.

43. The compound according to clause 11, wherein $R^{103}$ is W selected from the group consisting of pyrrolidinone, tetrahydropyrane, piperidinone and imidazole.

44. The compound according to any one clauses 1-43, wherein $R^1$ is selected from the group consisting of hydrogen, methyl, ethyl, isopropyl and cyclopropyl and $R^2$ is selected from the group consisting of a monovalent radical having one of the following formulae, wherein the symbol * denotes the point of attachment:

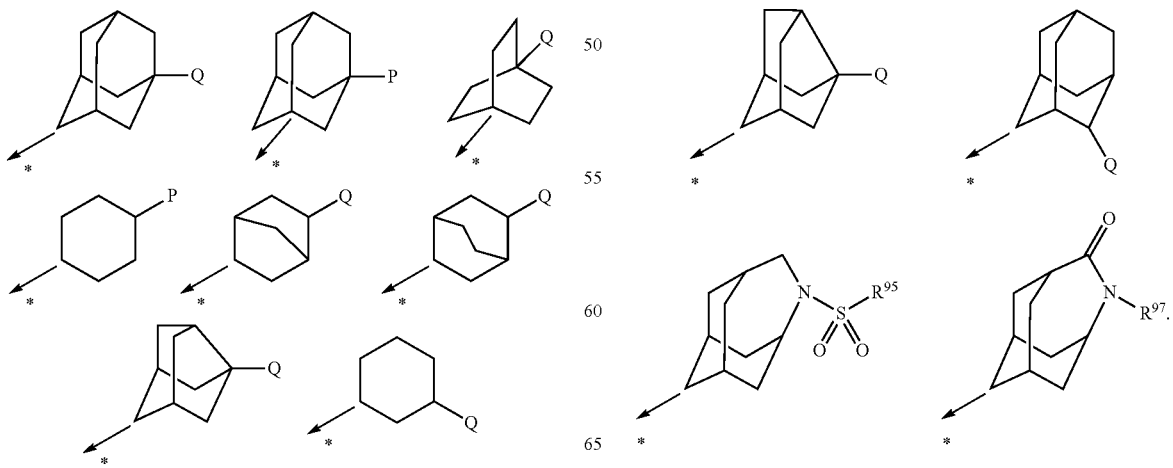

45. The compound according to clause 44, wherein $R^1$ is selected from the group consisting of hydrogen and methyl.

46. The compound according to clause 44, wherein $R^1$ is hydrogen.

47. The compound according to clause 44, wherein $R^1$ is methyl.

48. The compound according to any one of clauses 44-47, wherein $R^2$ is selected from the group consisting of:

49. The compound according to clause 48, wherein $R^2$ is selected from the group consisting of:

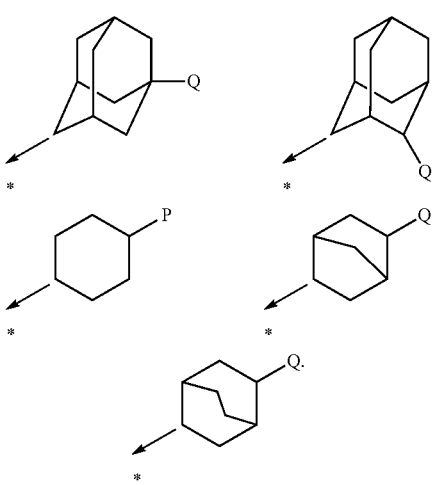

50. The compound according to clause 48, wherein $R^2$ is

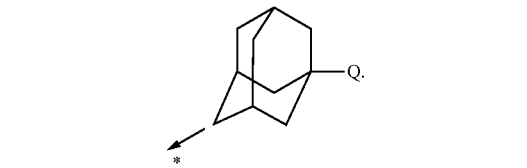

51. The compound according to clause 48, wherein $R^2$ is

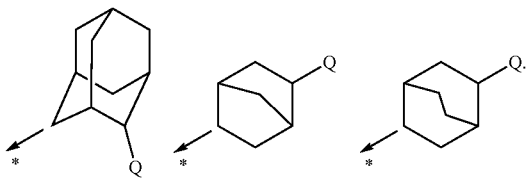

52. The compound according to clause 48, wherein $R^2$ is

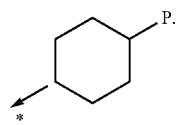

53. The compound according to clause 48, wherein $R^2$ is

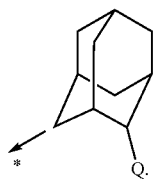

54. The compound according to clause 48, wherein $R^2$ is

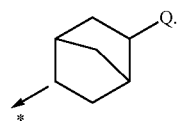

55. The compound according to clause 48, wherein $R^2$ is

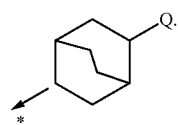

56. The compound according to any one of clauses 1-43, wherein $R^1$ and $R^2$ together with the nitrogen to which they are attached is selected from the group consisting of:

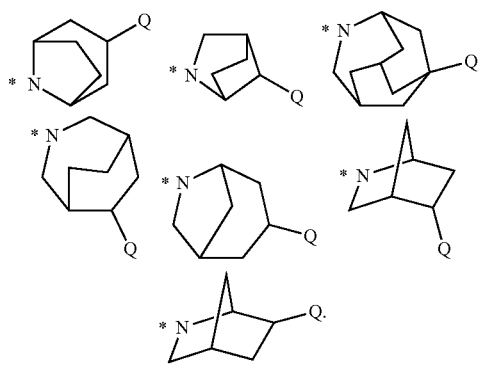

57. The compound according to clause 56, wherein $R^1$ and $R^2$ together with the nitrogen to which they are attached is

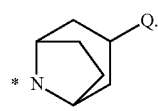

58. The compound according to any one any one of clauses 44-51 and 53-57, wherein Q is a hydroxyl group.

59. The compound according to any one of any one of clauses 44-51 and 53-57, wherein Q is a carboxy group.

60. The compound according to any one of clauses 44-51 and 53-57, wherein Q is a $-S(=O)_2R^6$ group.

61. The compound according to any one of clauses 44-51 and 53-57, wherein Q is selected is a $-S(=O)_2NH_2$ group.

62. The compound according to any one of clauses 44-52 wherein P is a $-S(=O)_2R^6$ group.

63. The compound according to any one of clauses 44-52, wherein P is a carboxy group.

64. The compound according to any one of clauses 44-52, wherein P is a $-S(=O)_2NH_2$ group.

65. The compound according to clause 60 or 62, wherein $R^6$ is selected from the group consisting of methyl, isopropyl, ethyl, phenyl, pyridine, cyclopropyl, cyclobutyl, cyclohexyl and cyclopentyl, wherein said methyl, isopropyl, ethyl, phenyl, pyridine, cyclopropyl, cyclobutyl, cyclohexyl and cyclopentyl are optionally substituted with one or two independently selected $R^7$.

66. The compound according to clause 60 or 62, wherein $R^6$ is selected from the group consisting of methyl, ethyl, isopropyl, phenyl, pyridine, cyclopropyl and cyclohexyl, wherein said methyl, isopropyl, phenyl, pyridine, cyclopropyl and cyclohexyl are optionally substituted with $R^7$.

67. The compound according to clauses 65 or 66, wherein $R^7$ is selected from the group consisting of hydrogen, methyl, cyclopropyl, —O—$CH_3$, —O-cyclopropyl, —O-isopropyl, hydroxy, fluoride and chloride, wherein said methyl, ethyl, cyclopropyl, —O—$CH_3$, —O-isopropyl and —O-cyclopropyl is optionally substituted with one substituent selected from the group consisting of hydroxy and halogen.

68. The compound according to clause 65 or 66, wherein $R^7$ is selected from the group consisting of hydrogen, methyl, cyclopropyl, —O-cyclopropyl, —O-isopropyl, hydroxy, fluoride and chloride, wherein said ethyl, cyclopropyl and —O-cyclopropyl is optionally substituted with one substituent selected from the group consisting of hydroxy and halogen.

69. The compound according to any one clauses 1-68, wherein $R^4$ is selected from the group consisting of hydrogen, methyl, isopropyl, ethyl, —O-methyl, —O-isopropyl, —O-ethyl, wherein said, methyl, isopropyl, ethyl, —O-methyl, —O-isopropyl, —O-ethyl are substituted with $R^{12}$ and $R^{13}$, trifluoromethyl, CN, fluorine, chlorine, —S($=$O)$_2$methyl, —S($=$O)$_2$ethyl, —S($=$O)$_2$cyclopropyl, —S($=$O)$_2$NHR$^{11}$ and —C($=$O)NHR$^{10}$.

70. The compound according to any one clauses 1-68, wherein $R^4$ is selected from the group consisting of hydrogen, methyl, isopropyl, ethyl, —O-methyl, —O-isopropyl, —O-ethyl, wherein said, methyl, isopropyl, ethyl, —O-methyl, —O-isopropyl, —O-ethyl are, substituted with $R^{12}$, trifluoromethyl, fluorine, chlorine, —S($=$O)$_2$(methyl)$_2$, —S($=$O)$_2$ methyl, —S($=$O)$_2$ethyl, —S($=$O)$_2$cyclopropyl, —S($=$O)$_2$Nmethyl, —S($=$O)$_2$Nisopropyl, —C($=$O)Nisopropyl, —C($=$O)N(methyl)$_2$ and —C($=$O)Nmethyl.

71. The compound according to any one clause 1-68, wherein $R^4$ is selected from the group consisting of hydrogen, methyl, isopropyl, —O-methyl, —O-isopropyl, —O-ethyl, trifluoromethyl, fluorine, chlorine, —S($=$O)$_2$methyl, —S($=$O)$_2$ethyl, —S($=$O)$_2$cyclopropyl, —S($=$O)$_2$Nmethyl, —S($=$O)$_2$Nisopropyl, —C($=$O)Nisopropyl and —C($=$O)Nmethyl.

72. The compound according to any one of clauses 69-71 wherein $R^4$ is in the ortho position.

73. The compound according to any one of clauses 69-71, wherein $R^4$ is in the meta position.

74. The compound according to any one of clauses 44-48 and 69-73, wherein $R^{95}$ is selected from the group consisting of methyl, isopropyl, ethyl, phenyl, pyridine, pyrimidine, cyclopropyl, cyclobutyl and cyclohexyl, wherein said ethyl, phenyl, pyridine, pyrimidine, cyclopropyl, cyclobutyl and cyclohexyl are optionally substituted with one or two independently selected $R^{96}$.

75. The compound according to any one of clauses 44-48 and 69-73 wherein $R^{95}$ is selected from the group consisting of methyl, isopropyl, phenyl, pyridine, pyrimidine, cyclopropyl and cyclohexyl, wherein said ethyl, phenyl, pyridine, pyrimidine, cyclopropyl and cyclohexyl are optionally substituted with one $R^{96}$.

76. The compound according to clauses 74 or 75, wherein $R^{96}$ is selected from the group consisting of fluorine, chlorine, hydroxy, oxo, trifluoromethyl, methyl, isopropyl, ethyl and —S($=$O)$_2$methyl.

77. The compound according clauses 74 or 75, wherein $R^{96}$ is selected from the group consisting of fluorine, chlorine, hydroxy, trifluoromethyl, methyl, isopropyl and —S($=$O)$_2$methyl.

78. The compound according to any one of clauses 44-48 and 69-73, wherein $R^{97}$ is selected from the group consisting of hydrogen, methyl, isopropyl and ethyl.

79. The compound according to any one of clauses 44-48 and 69-73, wherein $R^{97}$ is selected from the group consisting of hydrogen, methyl and isopropyl.

80. The compound according to any one of clauses 1-79, wherein $R^{12}$ is selected from the group consisting of hydrogen, —O-(methyl, isopropyl, ethyl), fluorine, chlorine, carboxy and hydroxy.

81. The compound according to any one of clauses 1-79, wherein $R^{12}$ is selected from the group consisting of hydrogen, —O-methyl, —O-isopropyl, fluorine and hydroxy.

82. The compound according to any one of clauses 1-81, wherein $R^{13}$ is selected from the group consisting of hydrogen, —O-(methyl, isopropyl, ethyl), fluorine, chlorine, carboxy and hydroxy.

83. The compound according to any one of clauses 1-79, wherein $R^{13}$ is selected from the group consisting of hydrogen, —O-methyl, —O-isopropyl, fluorine and hydroxy.

84. The compound according to any one of clauses 1-83, wherein $R^5$ is selected from the group consisting of hydrogen, methyl, isopropyl, ethyl, trifluoromethyl, CN, fluorine, chlorine, acetyl, ethy, carbonyl, —S($=$O)$_2$R$^{17}$, S($=$O)$_2$NR$^{14}$R$^{15}$, S-methyl, S-isopropyl, and S-ethyl; wherein said methyl, isopropyl, ethyl are substituted with $R^{16}$ and; wherein said ethyl and carbonyl are substituted with $R^{18}$.

85. The compound according to any one of clauses 1-83, wherein $R^5$ is selected from the group consisting of hydrogen, methyl, isopropyl, ethyl, trifluoromethyl, fluorine, chlorine, acetyl, —S($=$O)$_2$methyl, —S($=$O)$_2$ isopropyl, S($=$O)$_2$NH$_2$, S($=$O)$_2$N(CH$_3$)$_2$, S-methyl, S-isopropyl, and S-ethyl; wherein said methyl, isopropyl, and ethyl are optionally substituted with fluorine or hydroxyl.

86. The compound according to any one clauses 1-83, wherein $R^5$ is selected from the group consisting of hydrogen, methyl, isopropyl, trifluoromethyl, fluorine, chlorine, acetyl, —S($=$O)$_2$methyl and —S($=$O)$_2$ isopropyl.

87. The compound according to any one of clauses 1-86, wherein $R^{10}$ and $R^{11}$ are each independently selected from the group consisting of hydrogen, and $C_1$-$C_4$alkyl.

88. The compound according to any one of clauses 1-86, wherein $R^{10}$ and $R^{11}$ are each independently selected from the group consisting of hydrogen, methyl, ethyl and isopropyl.

89. The compound according to any one clauses 1-86, wherein $R^{10}$ and $R^{11}$ together with the nitrogen to which they are attached form a piperidinyl, pyrrolidinyl and morpholinyl ring, wherein said ring optionally is substituted with one or two substituents independently selected from the group consisting of hydroxy and fluoride.

90. The compound according to any one clauses 1-86, wherein $R^{10}$ and $R^{11}$ together with the nitrogen to which they are attached form a piperidinyl, ring, wherein said ring optionally is substituted with one or two substituents independently selected from the group consisting of hydroxy and fluoride.

91. The compound according to any one of clauses 1-90, wherein $R^{14}$ and $R^{15}$ are each independently selected from the group consisting of hydrogen, and $C_1$-$C_4$alkyl.

92. The compound according to any one of clauses 1-90, wherein $R^{14}$ and $R^{15}$ are each independently selected from the group consisting of hydrogen, methyl, ethyl and isopropyl.

93. The compound according to any one of clauses 1-90, wherein $R^{14}$ and $R^{15}$ together with the nitrogen to which they are attached form a piperidinyl, pyrrolidinyl and morpholinyl ring wherein said ring optionally is substituted with one or two substituents independently selected from the group consisting of hydroxy and fluoride.

94. The compound according to any one of clauses 1-90, wherein $R^{14}$ and $R^{15}$ together with the nitrogen to which they are attached form a piperidinyl ring, wherein said ring optionally is substituted with one or two substituents independently selected from the group consisting of hydroxy and fluoride 95. The compound according to any one of clauses 1-94, wherein $R^{16}$ is selected from the group consisting of hydrogen —O-methyl, methyl, cyclopropyl, fluorine, chlorine, —S(=O)$_2$-methyl, —S(=O)$_2$-ethyl, —C(=O)NH$_2$, —C(=O)N—CH$_3$CH$_3$, carboxy, and hydroxy.

96. The compound according to any one of clauses 1-94, wherein $R^{16}$ is selected from the group consisting of hydrogen, methyl, cyclopropyl, fluorine, —S(=O)$_2$-methyl, —C(=O)N—(CH$_3$)$_2$ and hydroxy.

97. The compound according to any one of clauses 1-96, wherein $R^{18}$ is selected from the group consisting of hydrogen —O-methyl, methyl, cyclopropyl, fluorine, chlorine, —S(=O)$_2$-methyl, —S(=O)$_2$-ethyl, —C(=O)NH$_2$, —C(=O)N—CH$_3$CH$_3$, carboxy, and hydroxy.

98. The compound according to any one of clauses 1-96, wherein $R^{18}$ is selected from the group consisting of hydrogen, methyl, cyclopropyl, fluoride, —S(=O)$_2$-methyl, —C(=O)N—(CH$_3$)$_2$ and hydroxy.

99. The compound according to any one clauses 1-98, wherein $R^{17}$ is selected from the group consisting of hydrogen, methyl, ethyl and isopropyl, wherein said ethyl and isopropyl is optionally substituted with one or two substituents selected from the group consisting of hydroxyl, fluorine and chlorine.

100. The compound according to any one of clauses 1-98, wherein $R^{17}$ is selected from the group consisting of hydrogen, methyl, ethyl and isopropyl, wherein said ethyl is optionally substituted with one substituents selected from the group consisting of hydroxy and fluorine.

101. The compound according to any one of clauses 1-100, wherein $R^{19}$ is selected from the group consisting of halogen, —CN, —C(=O)$R^{46}$, —CH(OH)—$R^{47}$, —(C), —$R^{44}R^{45}$—C(=O)—NR$^{48}R^{49}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}R^{49}$, —(CR$^{44}$R$^{45}$)$_m$—NR$^{48}$S(=O)$_2$R$^{50}$, —(CR$^{44}$R$^{45}$)$_m$—NR$^{48}$C(=O)—NR$^{48}R^{49}$, —(CR$^{44}$R$^{45}$)$_m$—C=C—R$^{51}R^{52}$, and —(CR$^{44}$R$^{45}$)$_m$—C≡C—R$^{53}$.

102. The compound according to any one of clauses 1-100, wherein $R^{19}$ is selected from the group consisting of, —(CR$^{44}$R$^{45}$)$_m$—C$_3$-C$_{10}$cycloalkyl substituted with $R^{55}$, and —(CR$^{44}$R$^{45}$)$_m$-aryl substituted with $R^{56}$ and $R^{57}$.

103. The compound according to any one of clauses 1-100, wherein $R^{19}$ is selected from the group consisting of —CN, —(CR$^{44}$R$^{45}$)$_m$—C(=O)—NR$^{48}R^{49}$, —(CR$^{44}$R$^{45}$)$_m$—OR$^{49}$, —(CR$^{44}$R$^{45}$)$_m$—S(=O)$_2$R$^{59}$, —(CR$^{44}$R$^{45}$)$_m$—S(=O)$_2$NR$^{48}R^{49}$, —(CR$^{44}$R$^{45}$), —NR$^{48}$S(=O)$_2$R$^{59}$, —(CR$^{44}$R$^{45}$)$_m$—NR$^{48}$C(=O)—NR$^{48}R^{49}$.

104. The compound according to any one of clauses 1-100, wherein $R^{19}$ is selected from the group consisting of, —C$_3$-C$_{10}$cycloalkyl substituted with $R^{55}$, and -phenyl substituted with $R^{56}$.

105. The compound according to any one of clauses 1-100, wherein $R^{19}$ is selected from the group consisting of —CN, —C(=O)—NR$^{48}R^{49}$, —NR$^{48}$C(=O)R$^{46}$, —OR$^{49}$, —S(=O)$_2$R$^{50}$, —S(=O)$_2$NR$^{48}R^{49}$, —NR$^{48}$S(=O)$_2$R$^{50}$, —NR$^{48}$C(=O)—NR$^{48}R^{49}$.

106. The compound according to any one of clauses 1-105, wherein $R^{22}$ is selected from the group consisting of halogen, —CN, hydroxy, —C(=O)OH, —C(=O)R$^{46}$, —CH(OH)—R$^{47}$, hydroxy, —(CR$^{44}$R$^{45}$)$_m$—C(=O)—NR$^{48}R^{49}$, —(CR$^{44}$R$^{45}$)$_m$—NR$^{48}$C(=O)R$^{46}$, —(CR$^{44}$R$^{45}$)$_m$—OR$^{49}$, —(CR$^{44}$R$^{45}$)$_m$—SR$^{49}$, —(CR$^{44}$R$^{45}$)$_m$—S(=O)$_2$R$^{50}$, —(CR$^{44}$R$^{45}$)$_m$—S(=O)$_2$NR$^{48}R^{49}$, —(CR$^{44}$R$^{45}$)$_m$—NR$^{48}$S(=O)$_2$R$^{50}$, —(CR$^{44}$—R$^{45}$)$_m$—NR$^{48}R^{49}$, —(CR$^{44}$R$^{45}$)$_m$—NR$^{48}$C(=O)—NR$^{48}R^{49}$, —(CR$^{44}$R$^{45}$)$_m$—C=C—R$^{51}R^{52}$, —(CR$^{44}$R$^{45}$)$_m$—C≡C—R$^{53}$.

107. The compound according to any one of clauses 1-105 wherein $R^{22}$ is selected from the group consisting of —(CR$^{44}$R$^{45}$)$_m$—C$_3$-C$_{10}$heterocyclyl substituted with $R^{54}$, —(CR$^{44}$R$^{45}$)$_m$—C$_3$-C$_{10}$cycloalkyl substituted with $R^{55}$, —(CR$^{44}$R$^{45}$)$_m$-aryl substituted with $R^{56}$ and $R^{57}$ and —(CR$^{44}$R$^{45}$)$_m$-heteroaryl substituted with $R^{56}$ and $R^{57}$.

108. The compound according to any one of clauses 1-105, wherein $R^{22}$ is selected from the group consisting of fluorine, chlorine, —CN, hydroxy, —C(=O)OH, CR$^{44}$R$^{45}$)$_m$—C(=O)—NR$^{48}R^{49}$, —(CR$^{44}$R$^{45}$)$_m$—NR$^{48}$C(=O)R$^{46}$, —(CR$^{44}$R$^{45}$)$_m$—OR$^{49}$, —(CR$^{44}$R$^{45}$)$_m$—S(=O)$_2$R$^{50}$, —(CR$^{44}$R$^{45}$)$_m$—S(=O)$_2$NR$^{48}R^{49}$, —(CR$^{44}$R$^{45}$)$_m$—NR$^{48}$S(=O)$_2$R$^{59}$, —(CR$^{44}$R$^{45}$)$_m$—NR$^{48}$C(=O)—NR$^{48}R^{49}$.

109. The compound according to any one of clauses 1-105 wherein $R^{22}$ is selected from the group consisting of —C$_3$-C$_{10}$heterocyclyl substituted with $R^{54}$, —C$_3$-C$_{10}$cycloalkyl substituted with $R^{55}$, -phenyl substituted with $R^{56}$ and -heteroaryl substituted with $R^{56}$.

110. The compound according to any one clauses 1-105, wherein $R^{22}$ is selected from the group consisting of fluorine, chlorine, —CN, hydroxy, —C(=O)OH, —C(=O)—NR$^{48}R^{49}$, —NR$^{48}$C(=O)R$^{46}$, —OR$^{49}$, —S(=O)$_2$R$^{50}$, —S(=O)$_2$NR$^{48}R^{49}$, —NR$^{48}$S(=O)$_2$R$^{59}$, —NR$^{48}$C(=O)—NR$^{48}R^{49}$.

111. The compound according to any one of clauses 1-105, wherein $R^{22}$ is selected from the group consisting of tetrahydropyranyl, piperidinyl, pyrrolidinyl and morpholinyl substituted with $R^{54}$, cyclopropyl, cyclobutyl, cyclohexyl and cyclopentyl substituted with $R^{55}$, -phenyl substituted with $R^{56}$ and imidazolyl, pyrazolyl, isoxazolyl, pyridazinyl, pyrazinyl pyrimidinyl and pyridinyl substituted with $R^{56}$.

112. The compound according to any one of clauses 1-105, wherein $R^{22}$ is selected from the group consisting of tetrahydropyranyl, piperidinyl and morpholinyl substituted with $R^{54}$, cyclopropyl, cyclobutyl, cyclohexyl and cyclopentyl substituted with $R^{55}$, phenyl substituted with $R^{56}$ and pyridazinyl, pyrazinyl pyrimidinyl and pyridinyl substituted with $R^{56}$.

113. The compound according to any one of clauses 1-105, wherein $R^{22}$ is selected from the group consisting of C=C—R$^{51}R^{52}$, —C≡C—R$^{53}$ and —CH$_2$CH$_2$OH.

114. The compound according to any one of clauses 1-113, wherein $R^{24}$ is selected from the group consisting of —C(=O)—R$^{26}$, —S(=O)$_2$—R$^{27}$, imidazolyl, pyrazolyl, isoxazolyl, pyridazinyl, pyrazinyl pyrimidinyl and pyridinyl substituted with $R^{28}$, and phenyl substituted with $R^{29}$.

115. The compound according to any one of clauses 1-113, wherein $R^{24}$ is selected from the group consisting of —C(=O)—R$^{26}$, —S(=O)$_2$—R$^{27}$, pyridazinyl, pyrazinyl pyrimidinyl and pyridinyl substituted with $R^{28}$, and phenyl substituted with $R^{29}$.

116. The compound according to any one of clauses 1-115, wherein $R^{25}$ is selected from the group consisting of hydrogen, methyl, ethyl, isopropyl and cyclopropyl.

117. The compound according to any one of clauses 1-115, wherein $R^{25}$ is selected from the group consisting of hydrogen, methyl, isopropyl and cyclopropyl.

118. The compound according to any one of clauses 1-117, wherein $R^{125}$ is selected from the group consisting of hydrogen, methyl, ethyl, isopropyl and cyclopropyl.

119. The compound according to any one of clauses 1-118, wherein $R^{125}$ is selected from the group consisting of hydrogen, methyl, isopropyl and cyclopropyl.

120. The compound according to any one of clauses 1-119, wherein $R^{44}$ and $R^{45}$ are each independently selected from the group consisting hydrogen, fluorine, chlorine, methyl, ethyl, isopropyl, cyclopropyl, cyclobutyl, cyclohexyl and cyclopentyl, wherein said ethyl, isopropyl, cyclopropyl, cyclobutyl, cyclohexyl and cyclopentyl are optionally substituted with one substituent selected independently from the group consisting of fluorine, chlorine, hydroxy and oxo.

121. The compound according to any one of clauses 1-119, wherein $R^{44}$ and $R^{45}$ are each independently selected from the group consisting hydrogen, fluorine, chlorine, methyl, ethyl, isopropyl, cyclopropyl, cyclobutyl, cyclohexyl and cyclopentyl, wherein said ethyl, cyclopropyl, cyclobutyl, cyclohexyl and cyclopentyl are optionally substituted with one substituent selected independently from the group consisting of fluorine and hydroxyl.

122. The compound according to any one of clauses 1-121, wherein $R^{44}$ and $R^{45}$ together with the carbon atom to which they are attached form a cyclopropyl ring, wherein said ring are optionally substituted with hydroxy or fluorine.

123. The compound according to any one of clauses 1-122, wherein $R^{44}$ and $R^{45}$ together with the carbon atom to which they are attached form a cyclobutyl ring, wherein said ring are optionally substituted with hydroxy or fluorine.

124. The compound according to any one of clauses 1-123, wherein $R^{70}$ and $R^{71}$ are each independently selected from the group consisting hydrogen, fluorine, chlorine, methyl, ethyl, isopropyl, cyclopropyl, cyclobutyl, cyclohexyl and cyclopentyl, wherein said ethyl, isopropyl, cyclopropyl, cyclobutyl, cyclohexyl and cyclopentyl are optionally substituted with one substituent selected independently from the group consisting of fluorine, chlorine, hydroxy and oxo.

125. The compound according to any one of clauses 1-123, wherein $R^{70}$ and $R^{71}$ are each independently selected from the group consisting hydrogen, fluorine, chlorine, methyl, ethyl, isopropyl, cyclopropyl, cyclobutyl, cyclohexyl and cyclopentyl, wherein said ethyl, cyclopropyl, cyclobutyl, cyclohexyl and cyclopentyl are optionally substituted with one substituent selected independently from the group consisting of fluorine and hydroxyl.

126. The compound according to any one of clauses 1-123, wherein $R^{70}$ and $R^{71}$ together with the carbon atom to which they are attached form a cyclopropyl ring, wherein said ring are optionally substituted with hydroxy or fluorine.

127. The compound according to any one of clauses 1-123, wherein $R^{70}$ and $R^{71}$ together with the carbon atom to which they are attached form a cyclobutyl ring, wherein said ring are optionally substituted with hydroxy or fluorine.

128. The compound according to any one of clauses 1-123, wherein $R^{72}$ and $R^{73}$ are each independently selected from the group consisting hydrogen, fluorine, chlorine, methyl, ethyl, isopropyl, cyclopropyl, cyclobutyl, cyclohexyl and cyclopentyl, wherein said ethyl, isopropyl, cyclopropyl, cyclobutyl, cyclohexyl and cyclopentyl are optionally substituted with one substituent selected independently from the group consisting of fluorine, chlorine, hydroxy and oxo.

129. The compound according to any one of clauses 1-123, wherein $R^{72}$ and $R^{73}$ are each independently selected from the group consisting hydrogen, fluorine, chlorine, methyl, ethyl, isopropyl, cyclopropyl, cyclobutyl, cyclohexyl and cyclopentyl, wherein said ethyl, cyclopropyl, cyclobutyl, cyclohexyl and cyclopentyl are optionally substituted with one substituent selected independently from the group consisting of fluorine and hydroxyl.

130. The compound according to any one of clauses 1-123, wherein $R^{72}$ and $R^{73}$ together with the carbon atom to which they are attached form a cyclopropyl ring, wherein said ring are optionally substituted with hydroxy or fluorine.

131. The compound according to any one clauses 1-123, wherein $R^{72}$ and $R^{73}$ together with the carbon atom to which they are attached form a cyclobutyl ring, wherein said ring are optionally substituted with hydroxy or fluorine.

132. The compound according to any one of clauses 1-131, wherein $R^{30}$ and $R^{31}$ are each independently selected from the group consisting of hydrogen, halogen, CN, —C(=O)OH, —C(=O)$R^{46}$, —CH(OH)—$R^{47}$, hydroxy, —$(CR^{44}R^{45})_m$—C(=O)—$NR^{48}R^{49}$, —$(CR^{44}R^{45})_m$—$NR^{45}C(=O)R^{46}$, —$(CR^{44}R^{45})_m$—$OR^{49}$, —$(CR^{44}R^{45})_m$—$SR^{49}$, —$(CR^{44}R^{45})_m$—S(=O)$_2R^{50}$, —$(CR^{44}R^{45})_m$—S(=O)$_2NR^{48}R^{49}$, —$(CR^{44}R^{45})_m$—$NR^{45}S(=O)_2R^{50}$, —$(CR^{44}R^{45})_m$—$NR^{48}R^{49}$, —$(CR^{44}R^{45})_m$—$NR^{45}C(=O)$—$NR^{48}R^{49}$, —$(CR^{44}R^{45})_m$—C=C—$R^{51}R^{52}$, and —$(CR^{44}R^{45})_m$—C≡C—$R^{53}$.

133. The compound according to any one of clauses 1-131, wherein $R^{30}$ and $R^{31}$ are each independently selected from the group consisting of hydrogen, halogen, CN, —C(=O)OH, hydroxy, —$(CR^{44}R^{45})_m$—C(=O)—$NR^{48}R^{49}$, —$(CR^{44}R^{45})_m$—$NR^{48}C(=O)R^{46}$, —$(CR^{44}R^{45})_m$—$OR^{49}$, —$(CR^{44}R^{45})_m$—$SR^{49}$, —$(CR^{44}R^{45})_m$—S(=O)$_2R^{50}$, —$(CR^{44}R^{45})_m$—S(=O)$_2NR^{48}R^{49}$, —$(CR^{44}R^{45})_m$—$NR^{48}S(=O)_2R^{50}$, —$(CR^{44}R^{45})_m$—$NR^{45}C(=O)$—$NR^{48}R^{49}$, and —$(CR^{44}R^{45})_m$—C≡C—$R^{53}$.

134. The compound according to any one of clauses 1-131, wherein $R^{30}$ ad $R^{31}$ are each independently selected from the group consisting of hydrogen, halogen, CN, —C(=O)OH, hydroxy, —C(=O)—$NR^{48}R^{49}$, —$NR^{45}C(=O)R^{46}$, —$OR^{49}$, —S(=O)$_2R^{50}$, —S(=O)$_2NR^{48}R^{49}$, —$NR^{45}S(=O)_2R^{50}$, —$NR^{48}C(=O)$—$NR^{48}R^{49}$ and —C≡C—$R^{53}$.

135. The compound according to any one clauses 1-131, wherein $R^{30}$ ad $R^{31}$ are each independently selected from the group consisting of hydrogen, halogen, CN, —C(=O)OH, hydroxy, —C(=O)—$NR^{48}R^{49}$, —S(=O)$_2R^{50}$ and —S(=O)$_2NR^{48}R^{49}$.

136. The compound according to any one of clauses 1-131, wherein $R^{30}$ ad $R^{31}$ are each independently selected from the group consisting of hydrogen, halogen, CN, —C(=O)OH, hydroxy, —$NR^{48}C(=O)R^{46}$, —$OR^{49}$, —$NR^{45}S(=O)_2R^{50}$ and —$NR^{45}C(=O)$—$NR^{48}R^{49}$.

137. The compound according to any one of clauses 1-131, wherein $R^{30}$ ad $R^{31}$ are each independently selected from the group consisting of hydrogen, chlorine, fluorine, CN, —C(=O)OH, hydroxy, —NHC(=O)$C_{1-4}$alkyl, —$OC_{1-4}$alkyl, —OCH$_2$CH$_2$OH, —NHS(=O)$_2C_{1-4}$alkyl and —NHC(=O)—N($C_{1-4}$alkyl)$_2$.

138. The compound according to any one of clauses 1-137, wherein $R^{30}$, $R^{31}$, $R^{42}$ and $R^{43}$ are each independently selected from the group consisting of —$(CR^{44}R^{45})_m$—$C_3$-$C_{10}$heterocyclyl substituted with $R^{54}$, —$(CR^{44}R^{45})_m$—$C_3$-$C_{10}$cycloalkyl substituted with $R^{55}$, —$(CR^{44}R^{45})_m$-aryl substituted with $R^{56}$ and $R^{57}$ and —$(CR^{44}R^{45})_m$-heteroaryl substituted with $R^{56}$ and $R^{57}$.

139. The compound according to any one of clauses 1-137, wherein $R^{30}$, $R^{31}$, $R^{42}$ and $R^{43}$ are each independently selected from the group consisting of —$C_3$-$C_{10}$heterocyclyl substituted with $R^{54}$, —$C_3$-$C_{10}$cycloalkyl substituted with $R^{55}$, -phenyl substituted with $R^{56}$ and $R^{57}$ and -heteroaryl substituted with $R^{56}$ and $R^{57}$.

140. The compound according to any one of clauses 1-137, wherein $R^{30}$, $R^{31}$, $R^{42}$ and $R^{43}$ are each independently selected from the group consisting of tetrahydropyranyl, piperidinyl, pyrrolidinyl and morpholinyl substituted with $R^{54}$, cyclopropyl, cyclobutyl, cyclohexyl and cyclopentyl substituted with $R^{55}$, phenyl substituted with $R^{56}$ and $R^{57}$ and imidazolyl, pyrazolyl, isoxazolyl, pyridazinyl, pyrazinyl pyrimidinyl and pyridinyl substituted with $R^{56}$ and $R^{57}$.

141. The compound according to any one of clauses 1-137, wherein $R^{30}$, $R^{31}$, $R^{42}$ and $R^{43}$ are each independently selected from the group consisting of tetrahydropyranyl, piperidinyl, pyrrolidinyl and morpholinyl substituted with $R^{54}$, cyclopropyl, cyclobutyl and cyclohexyl substituted with $R^{55}$, phenyl substituted with $R^{56}$ and $R^{57}$ and pyridazinyl, pyrazinyl pyrimidinyl and pyridinyl substituted with $R^{56}$ and $R^{57}$.

142. The compound according to any one of clauses 1-141, wherein $R^{90}$ and $R^{91}$ are each independently selected from the group consisting of hydrogen, halogen, $=O$, $-CN$, $-C(=O)OH$, $-C(=O)R^{46}$, $-CH(OH)-R^{47}$, hydroxy, trifluoromethyl, $-(CR^{44}R^{45})_m-C(=O)-NR^{48}R^{49}$, $-(CR^{44}R^{45})_m-NR^{48}C(=O)R^{46}$, $-(CR^{44}R^{45})_m-OR^{49}$, $-(CR^{44}R^{45})_m-SR^{49}$, $-(CR^{44}R^{45})_m-S(=O)_2R^{50}$, $-(CR^{44}R^{45})_m-S(=O)_2NR^{48}R^{49}$, $-(CR^{44}R^{45})_m-NR^{45}S(=O)_2R^{50}$, $-(CR^{44}R^{45})_m-NR^{48}R^{49}$, $-(CR^{44}R^{45})_m-NR^{45}C(=O)-NR^{48}R^{49}$, $-(CR^{44}R^{45})_m-C=CR^{51}R^{52}$, and $-(CR^{44}R^{45})_m-C\equiv C-R^{53}$.

143. The compound according to any one of clauses 1-141, wherein $R^{90}$ and $R^{91}$ are each independently selected from the group consisting of hydrogen, fluorine, chlorine, $=O$, $-CN$, $-C(=O)OH$, hydroxy, $-(CR^{44}R^{45})_m-C(=O)-NR^{48}R^{49}$, $-(CR^{44}R^{45})_m-NR^{48}C(=O)R^{46}$, $-(CR^{44}R^{45})_m-OR^{49}$, $-(CR^{44}R^{45})_m-SR^{49}$, $-(CR^{44}R^{45})_m-S(=O)_2R^{50}$, $-(CR^{44}R^{45})_m-S(=O)_2NR^{48}R^{49}$, $-(CR^{44}R^{45})_m-NR^{48}S(=O)_2R^{50}$, $-(CR^{44}R^{45})_m-NR^{48}C(=O)-NR^{48}R^{49}$, $-(CR^{44}R^{45})_m-C=CR^{51}R^{52}$, and $-(CR^{44}R^{45})_m-C\equiv-R^{53}$.

144. The compound according to any one of clauses 1-141, wherein $R^{90}$ and $R^{91}$ are each independently selected from the group consisting of hydrogen, fluorine, chlorine, $-CN$, $-C(=O)OH$, $-NR^{48}C(=O)R^{46}$, $-NR^{48}S(=O)_2R^{50}$ and $-NR^{48}C(=O)-NR^{48}R^{49}$.

145. The compound according to any one of clauses 1-141, wherein $R^{90}$ and $R^{91}$ are each independently selected from the group consisting of hydrogen, fluorine, chlorine, $=O$, $-CN$, $-C(=O)OH$, $-C(=O)-NR^{48}R^{49}$, $-OR^{49}$, $-SR^{49}$, $-S(=O)_2R^{50}$, $-S(=O)_2NR^{48}R^{49}$, $-C=CR^{51}R^{52}$ and $-C\equiv C-R^{53}$.

146. The compound according to any one of clauses 1-141, wherein $R^{90}$ and $R^{91}$ are each independently selected from the group consisting of hydrogen, $-(CR^{44}R^{45})_m-C_3-C_{10}$heterocyclyl substituted with $R^{54}$, $-(CR^{44}R^{45})_m-C_3-C_{10}$cycloalkyl substituted with $R^{55}$, $-(CR^{44}R^{45})_m$-aryl substituted with $R^{56}$ and $R^{57}$ and $-(CR^{44}R^{45})_m$-heteroaryl substituted with $R^{56}$ and $R^{57}$.

147. The compound according to any one of clauses 1-141, wherein $R^{90}$ and $R^{91}$ are each independently selected from the group consisting of hydrogen, tetrahydropyranyl, piperidinyl, pyrrolidinyl and morpholinyl substituted with $R^{54}$, cyclopropyl, cyclobutyl, cyclohexyl and cyclopentyl substituted with $R^{55}$, phenyl substituted with $R^{56}$ and $R^{57}$ and -imidazolyl, pyrazolyl, isoxazolyl, pyridazinyl, pyrazinyl pyrimidinyl and pyridinyl substituted with $R^{56}$ and $R^{57}$.

148. The compound according to any one of clauses 1-141, wherein $R^{90}$ and $R^{91}$ are each independently selected from the group consisting of hydrogen, tetrahydropyranyl, piperidinyl and morpholinyl substituted with $R^{54}$, cyclopropyl, cyclobutyl and cyclohexyl substituted with $R^{55}$, phenyl substituted with $R^{56}$ and $R^{57}$ and pyridazinyl, pyrazinyl pyrimidinyl and pyridinyl substituted with $R^{56}$ and $R^{57}$.

149. The compound according to any one of clauses 1-148, wherein m is 0.

150. The compound according to any one of clauses 1-148, wherein m is 1.

151. The compound according to any one of clauses 1-150, wherein $R^{32}$, $R^{33}$, $R^{37}$, $R^{38}$, $R^{39}$, $R^{49}$ and $R^{41}$ are each independently selected from the group consisting of hydrogen, $C_1-C_6$alkyl and $C_3-C_{10}$cycloalkyl, wherein said $C_1-C_6$alkyl and $C_3-C_{10}$cycloalkyl are optionally substituted with one or two independently selected $R^{58}$.

152. The compound according to clause 150, wherein $R^{32}$, $R^{33}$, $R^{37}$, $R^{38}$, $R^{39}$, $R^{49}$ and $R^{41}$ are each independently selected from the group consisting of hydrogen, $C_1-C_6$alkyl and $C_3-C_{10}$cycloalkyl, wherein said $C_1-C_6$alkyl and $C_3-C_{10}$cycloalkyl are optionally substituted with one $R^{58}$.

153. The compound according to clause 150, wherein $R^{32}$, $R^{33}$, $R^{37}$, $R^{38}$, $R^{39}$, $R^{49}$ and $R^{41}$ are each independently selected from the group consisting of hydrogen, methyl, ethyl and isopropyl, trifluoromethyl and cyclopropyl, cyclobutyl, cyclohexyl and cyclopentyl, wherein said methyl, ethyl and isopropyl, trifluoromethyl and cyclopropyl, cyclobutyl, cyclohexyl and cyclopentyl are optionally substituted with one $R^{58}$.

154. The compound according to clause 150, wherein $R^{32}$, $R^{33}$, $R^{37}$, $R^{38}$, $R^{39}$, $R^{49}$ and $R^{41}$ are each independently selected from the group consisting of hydrogen, $C_3-C_{10}$heterocyclyl, aryl and heteroaryl, wherein said $C_3-C_{10}$heterocyclyl, aryl and heteroaryl are optionally substituted with one or two independently selected $R^{58}$.

155. The compound according to clause 150, wherein $R^{32}$, $R^{33}$, $R^{37}$, $R^{38}$, $R^{39}$, $R^{49}$ and $R^{41}$ are each independently selected from the group consisting of hydrogen, $C_3-C_{10}$heterocyclyl, aryl and heteroaryl, wherein said $C_3-C_{10}$heterocyclyl, aryl and heteroaryl are optionally substituted with one or two independently selected $R^{58}$.

156. The compound according to clause 150, wherein $R^{32}$, $R^{33}$, $R^{37}$, $R^{38}$, $R^{39}$, $R^{49}$ and $R^{41}$ are each independently selected from the group consisting of hydrogen, tetrahydropyranyl, piperidinyl, pyrrolidinyl, morpholinyl, phenyl, imidazolyl, pyrazolyl, isoxazolyl, pyridazinyl, pyrazinyl, pyrimidinyl and pyridinyl wherein said tetrahydropyranyl, piperidinyl, pyrrolidinyl, morpholinyl, phenyl, imidazolyl, pyrazolyl, isoxazolyl, pyridazinyl, pyrazinyl pyrimidinyl and pyridinyl are optionally substituted with one or two independently selected $R^{58}$.

157. The compound according to clause 150, wherein $R^{32}$, $R^{33}$, $R^{37}$, $R^{38}$, $R^{39}$, $R^{49}$ and $R^{41}$ are each independently selected from the group consisting of hydrogen, tetrahydropyranyl, piperidinyl, morpholinyl, phenyl, pyridazinyl, pyrazinyl, pyrimidinyl and pyridinyl wherein said tetrahydropyranyl, piperidinyl, morpholinyl, phenyl, pyridazinyl, pyrazinyl, pyrimidinyl and pyridinyl are optionally substituted with one $R^{58}$.

158. The compound according to any one of clauses 1-157, wherein $R^{34}$, $R^{35}$, and $R^{36}$ are each independently selected from the group consisting of hydrogen, $C_1-C_6$alkyl, $C_3-C_{10}$cycloalkyl and heteroaryl, wherein said $C_1-C_6$alkyl, $C_3-C_{10}$cycloalkyl and heteroaryl are optionally substituted with one, two or three substituents independently selected from the group consisting of halogen, methyl, ethyl and hydroxyl.

159. The compound according to any one clauses 1-158, wherein $R^{34}$ and $R^{35}$ together with the nitrogen to which they are attached form a piperidinyl, pyrrolidinyl and morpholinyl ring, wherein said ring optionally is substituted with one or two substituents independently selected from the group consisting of hydroxy or fluorine.

160. The compound according to any one of clauses 1-157, wherein $R^{34}$, $R^{35}$, and $R^{36}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, methyl, ethyl and hydroxyl.

161. The compound according to any one of clauses 1-157, wherein $R^{34}$, $R^{35}$, and $R^{36}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one substituent independently selected from the group consisting of fluorine, methyl, ethyl and hydroxyl.

162. The compound according to any one of clauses 1-161, wherein $R^{26}$, $R^{27}$, $R^{46}$, $R^{47}$, $R^{49}$, $R^{50}$, $R^{51}$, $R^{53}$ and $R^{52}$ are each independently selected from the group consisting of hydrogen, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy.

163. The compound according to any one of clauses 1-162, wherein $R^{54}$, $R^{55}$, $R^{56}$ and $R^{57}$ are each independently selected from the group consisting of hydrogen, $C_1$-$C_6$alkyl, heteroaryl and $C_3$-$C_{10}$cycloalkyl, wherein said $C_1$-$C_6$alkyl, heteroaryl and $C_3$-$C_{10}$cycloalkyl are optionally substituted with one, two or three substituents independently selected from the group consisting of halogen, methyl, ethyl, methoxy, ethoxy, —OCH$_2$CH$_2$OH, carboxy and hydroxy.

164. The compound according to any one of clauses 1-163, wherein $R^{26}$, $R^{27}$, $R^{46}$, $R^{47}$, $R^{49}$, $R^{50}$, $R^{51}$, $R^{53}$ and $R^{52}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine, methyl, ethyl, methoxy, ethoxy, —OCH$_2$CH$_2$OH, carboxy and hydroxy.

165. The compound according to any one of clauses 1-164, wherein $R^{54}$, $R^{55}$, $R^{56}$ and $R^{57}$ are each independently selected from the group consisting of hydrogen, halogen, —CN, trifluoromethyl, —OCH$_2$CH$_2$OH, hydroxyl.

166. The compound according to any one of clauses 1-164, wherein $R^{54}$, $R^{55}$, $R^{56}$ and $R^{57}$ are each independently selected from the group consisting of hydrogen, methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine methyl, ethyl, methoxy, ethoxy, —OCH$_2$CH$_2$OH, carboxy and hydroxy.

167. The compound according to any one of clauses 1-166, wherein $R^{48}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

168. The compound according to any one of clauses 1-167, wherein $R^{49}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

169. The compound according to any one of clauses 1-167, wherein $R^{49}$ is H and $R^{48}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

170. The compound according to any one of clauses 1-167, wherein $R^{48}$ is H and $R^{49}$ is selected from the group consisting of hydrogen, methyl, ethyl and isopropyl, tetrahydropyrane, cyclohexyl and cyclopentyl wherein said methyl, ethyl and isopropyl, tetrahydropyrane, cyclohexyl and cyclopentyl are optionally substituted with one or two substituents independently selected from the group consisting of fluorine and hydroxy.

171. The compound according to any one of clauses 1-167, wherein $R^{48}$ and $R^{49}$ together with the nitrogen to which they are attached form a piperidinyl, pyrrolidinyl and morpholinyl ring, wherein said ring optionally is substituted with one or two substituents independently selected from the group consisting of hydroxy and fluoride.

172. The compound according to any one of clauses 1-171, wherein $R^{58}$ are each independently selected from selected from the group consisting of halogen, —CN, hydroxy, oxo, —C(=O)OH, —S(=O)$_2$R$^{59}$, —S—NR$^{60}$R$^{61}$, S(=O)$_2$NR$^{60}$R$^{61}$, cyclopropyl, —OR$^{59}$, —SR$^{59}$, $C_1$-$C_6$alkyl, —C(=O)NR$^{60}$R$^{61}$, —NR$^{60}$C(=O)NR$^{61}$R$^{60}$, —NR$^{60}$S(=O)$_2$R$^{59}$ and —NC(=O)R$^{59}$.

173. The compound according to any one of clauses 1-171, wherein $R^{58}$ is selected from the group consisting of fluorine, chlorine, —CN, hydroxy, oxo, —C(=O)OH, —S(=O)$_2$R$^{59}$, —S(=O)$_2$NR$^{60}$R$^{61}$, cyclopropyl, —OR$^{59}$, —SR$^{59}$, methyl, ethyl, isopropyl, —C(=O)NR$^{60}$R$^{61}$, —NR$^{60}$C(=O)NR$^{61}$R$^{60}$, —NR$^{60}$S(=O)$_2$R$^{59}$ and —NC(=O)R$^{59}$.

174. The compound according to any one of clauses 1-171, wherein $R^{58}$ are each independently selected from selected from the group consisting of fluorine, chlorine, —CN, hydroxy, oxo, —C(=O)OH, —S(=O)$_2$R$^{59}$, cyclopropyl, —OR$^{59}$, methyl, ethyl, isopropyl and —C(=O)NR$^{60}$R$^{61}$.

175. The compound according to any one of clauses 1-171, wherein $R^{58}$ are each independently selected from selected from the group consisting of —S(=O)$_2$NR$^{60}$R$^{61}$, —SR$^{59}$, —NR$^{60}$C(=O)NR$^{61}$R$^{60}$, —NR$^{60}$S(=O)$_2$R$^{59}$ and —NC(=O)R$^{59}$.

176. The compound according to any one of clauses 1-175, wherein $R^{59}$ is selected from the group consisting of hydrogen, $C_1$-$C_6$alkyl and $C_3$-$C_{10}$cycloalkyl wherein said —$C_6$alkyl, $C_3$-$C_{10}$cycloalkyl are optionally substituted with one, two or three substituents independently selected from the group consisting of halogen, methyl, ethyl, methoxy, ethoxy trifluoromethyl and hydroxy.

177. The compound according to any one of clauses 1-175, wherein $R^{59}$ is selected from the group consisting of hydrogen, phenyl and heteroaryl, wherein said, phenyl and heteroaryl are optionally substituted with one, two or three substituents independently selected from the group consisting of halogen, methyl, ethyl, methoxy, ethoxy and hydroxy.

178. The compound according to any one of clauses 1-175, wherein $R^{59}$ is selected from the group consisting of hydrogen, methyl, ethyl and isopropyl, cyclopropyl, cyclobutyl, cyclohexyl, cyclopentyl, phenyl, imidazolyl, pyrazolyl, isoxazolyl, pyridazinyl, pyrazinyl, pyrimidinyl and pyridinyl, wherein said methyl, ethyl and isopropyl, cyclopropyl, cyclobutyl, cyclohexyl, cyclopentyl, phenyl, imidazolyl, pyrazolyl, isoxazolyl, pyridazinyl, pyrazinyl, pyrimidinyl and pyridinyl are optionally substituted with one, two or three substituents independently selected from the group consisting of halogen, methyl, ethyl, methoxy, ethoxy and hydroxy.

179. The compound according to any one of clauses 1-178, wherein $R^{60}$ are each independently selected from the group consisting of hydrogen, methyl, ethyl, isopropyl, tetrahydropyranyl, piperidinyl, pyrrolidinyl, morpholinyl, cyclopropyl, cyclobutyl, cyclohexyl, cyclopentyl, and heteroaryl, wherein said methyl, ethyl, isopropyl, tetrahydropyranyl, piperidinyl, pyrrolidinyl, morpholinyl, cyclopropyl, cyclobutyl, cyclohexyl, cyclopentyl, and heteroaryl are optionally substituted with one or two substituents independently selected from the group consisting of fluorine, chlorine and hydroxy.

180. The compound according to any one of clauses 1-178, wherein $R^{60}$ are each independently selected from the group consisting of hydrogen, methyl, ethyl, isopropyl, cyclopropyl, wherein said methyl, ethyl, isopropyl and cyclopropyl are optionally substituted with one or two substituents independently selected from the group consisting of fluorine, chlorine and hydroxy.

181. The compound according to any one of clauses 1-180, wherein $R^{61}$ are each independently selected from the group consisting of hydrogen, $C_1$-$C_6$alkyl, $C_3$-$C_{10}$heterocyclyl, $C_3$-$C_{10}$cycloalkyl and heteroaryl, wherein said $C_1$-$C_6$alkyl, $C_3$-$C_{10}$heterocyclyl, $C_3$-$C_{10}$cycloalkyl and heteroaryl are optionally substituted with one or two substituents independently selected from the group consisting of halogen and hydroxy.

182. The compound according to any one clauses 1-181, wherein $R^{61}$ are each independently selected from the group consisting of hydrogen, methyl, ethyl, isopropyl, tetrahydropyranyl, piperidinyl, pyrrolidinyl, morpholinyl, cyclopropyl, cyclobutyl, cyclohexyl, cyclopentyl, and heteroaryl, wherein said methyl, ethyl, isopropyl, tetrahydropyranyl, piperidinyl, pyrrolidinyl, morpholinyl, cyclopropyl, cyclobutyl, cyclohexyl, cyclopentyl, and heteroaryl are optionally substituted with one or two substituents independently selected from the group consisting of fluorine, chlorine and hydroxy.

183. The compound according to any one of clauses 1-182, wherein $R^{93}$ is selected from the group consisting of hydrogen, methyl, ethyl, isopropyl, cyclopropyl, cyclobutyl, cyclohexyl, cyclopentyl, tetrahydropyranyl, piperidinyl, pyrrolidinyl, morpholinyl, phenyl, imidazolyl, pyrazolyl, isoxazolyl, pyridazinyl, pyrazinyl, pyrimidinyl and pyridinyl, wherein said methyl, ethyl, isopropyl, cyclopropyl, cyclobutyl, cyclohexyl, cyclopentyl, tetrahydropyranyl, piperidinyl, pyrrolidi- nyl, morpholinyl, phenyl, imidazolyl, pyrazolyl, isoxazolyl, pyridazinyl, pyrazinyl, pyrimidinyl and pyridinyl are optionally substituted with one, two or three independently selected $R^{58}$.

184. The compound according to any one of clauses 1-182, wherein $R^{93}$ is selected from the group consisting of hydrogen, methyl, ethyl, isopropyl, cyclopropyl, cyclobutyl, cyclohexyl, cyclopentyl, tetrahydropyranyl, piperidinyl, morpholinyl, phenyl, pyrimidinyl and pyridinyl, wherein said methyl, ethyl, isopropyl, cyclopropyl, cyclobutyl, cyclohexyl, cyclopentyl, tetrahydropyranyl, piperidinyl, morpholinyl, phenyl, pyrimidinyl and pyridinyl are optionally substituted with one, two or three independently selected $R^{58}$.

185. The compound according to any one of clauses 1-184, wherein $R^{94}$ and $R^{95}$ are each independently selected from the group consisting of hydrogen, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine, methyl, ethyl and hydroxy.

186. The compound according to any one of clauses 1-184, wherein $R^{94}$ is hydrogen and $R^{95}$ are selected from the group consisting of hydrogen, cyclopropyl, cyclobutyl, cyclohexyl, cyclopentyl, imidazolyl, pyrazolyl, isoxazolyl, pyridazinyl, pyrazinyl, pyrimidinyl and pyridinyl, wherein said cyclopropyl, cyclobutyl, cyclohexyl, cyclopentyl, imidazolyl, pyrazolyl, isoxazolyl, pyridazinyl, pyrazinyl, pyrimidinyl and pyridinyl are optionally substituted with one, two or three substituents independently selected from the group consisting of fluorine, chlorine, methyl, ethyl and hydroxy.

187. The compound according to any one of clauses 1-184, wherein $R^{94}$ and $R^{95}$ together with the nitrogen to which they are attached form a piperidinyl, pyrrolidinyl and morpholinyl ring, wherein said ring optionally is substituted with one or two substituents independently selected from the group consisting of hydroxy or fluorine.

188. The compound according to any one of clauses 1-184, wherein $R^{94}$ and $R^{95}$ together with the nitrogen to which they are attached form a piperidinyl and pyrrolidinyl ring, wherein said ring optionally is substituted with one or two substituents independently selected from the group consisting of hydroxy or fluorine.

189. The compound according to any one of clauses 1-188, wherein $R^{62}$ is selected from the group consisting of fluoride, chloride, —C(=O)OH, —CH(OH)—$R^{47}$, —C(=O)—$NR^{48}R^{49}$, —$NR^{48}C(=O)R^{46}$, —$SR^{49}$, —$S(=O)_2R^{50}$, —$S(=O)_2NR^{48}R^{49}$, —$NR^{48}S(=O)_2R^{50}$, —$NR^{48}C(=O)$—$NR^{48}R^{49}$, —C≡C—$R^{51}R^{52}$, —C≡C—$R^{53}$, and $CH_2CH_2OH$, —$CH_2CH_2OH$.

190. The compound according to any one of clauses 1-188, wherein $R^{62}$ is selected from the group consisting of $C_3$-$C_{10}$heterocyclyl substituted with $R^{54}$, $C_3$-$C_{10}$cycloalkyl substituted with $R^{55}$, aryl substituted with $R^{56}$ and $R^{57}$ and heteroaryl substituted with $R^{56}$ and $R^{57}$.

191. The compound according to any one clauses 1-188, wherein $R^{62}$ is selected from the group consisting of fluorine, chlorine, —CH(OH)-cyclopropyl, —C(=O)—$NR^{48}R^{49}$, —$NR^{48}C(=O)R^{46}$, —$S(=O)_2R^{50}$, —$S(=O)_2NR^{48}R^{49}$, —$NR^{48}S(=O)_2R^{59}$, —$NR^{48}C(=O)$—$NR^{48}R^{49}$, $CH_2CH_2OH$, —$CH_2CH_2OH$.

192. The compound according to any one of clauses 1-188, wherein $R^{62}$ is selected from the group consisting of tetrahydropyranyl, piperidinyl, pyrrolidinyl, morpholinyl substituted with $R^{54}$, cyclopropyl, cyclobutyl, cyclohexyl, cyclopentyl substituted with $R^{55}$, phenyl substituted with $R^{56}$ and $R^{57}$ and imidazolyl, pyrazolyl, isoxazolyl, pyridazinyl, pyrazinyl, pyrimidinyl and pyridinyl substituted with $R^{56}$ and $R^{57}$.

193. The compound according to any one of clauses 1-192, wherein $R^{63}$ is selected from the group consisting of hydrogen, fluoride, chloride, hydroxy, oxo, —S($=$O)$_2$R$^{59}$, —S($=$O)$_2$NR$^{60}$R$^{61}$, —S($=$O)NR$^{60}$R$^{61}$ cyclopropyl, —OR$^{59}$, methyl, ethyl, isopropyl, —C($=$O)NR$^{60}$R$^{61}$, —NR$^{60}$C($=$O)NR$^{61}$R$^{60}$; —NR$^{60}$S($=$O)$_2$R$^{59}$, and —N(C$=$O)R$^{59}$.

194. The compound according to any one of clauses 1-192, wherein $R^{63}$ is selected from the group consisting of hydrogen, fluoride, chloride, hydroxy, oxo, —S($=$O)$_2$R$^{59}$, —S($=$O)$_2$NR$^{60}$R$^{61}$, —S($=$O)NR$^{60}$R$^{61}$ cyclopropyl, —OR$^{59}$, methyl, ethyl, isopropyl and —C($=$O)NR$^{60}$R$^{61}$.

195. The compound according to any one of clauses 1-192, wherein $R^{63}$ is selected from the group consisting of hydrogen, fluoride, chloride, trifluoromethyl, hydroxy, oxo, —S($=$O)$_2$cyclopropyl, —S($=$O)$_2$methyl, cyclopropyl, —OR$^{59}$, methyl, ethyl and isopropyl.

196. A compound according to any one of clauses 1-195, wherein said compound is selected from the group consisting of N-(5-Hydroxy-adamantan-2-yl)-N-methyl-3-phenethyloxy-benzamide, N-(5-Hydroxy-adamantan-2-yl)-3-phenethyloxy-benzamide, 3-Cyclohexylmethoxy-N-(5-hydroxy-adamantan-2-yl)-N-methyl-benzamide, N-(5-Hydroxy-adamantan-2-yl)-N-methyl-3-(1-methyl-butoxy)-benzamide, N-(5-Hydroxy-adamantan-2-yl)-3-methoxy-N-methyl-benzamide, N-(5-Hydroxy-adamantan-2-yl)-N-methyl-3-(2-pyridin-2-yl-ethoxy)-benzamide, N-(5-Hydroxy-adamantan-2-yl)-3-(2-pyridin-2-yl-ethoxy)-benzamide, 3-Benzyloxy-N-(5-hydroxy-adamantan-2-yl)-benzamide, N-(5-Hydroxy-adamantan-2-yl)-3-(2-morpholin-4-yl-ethoxy)-benzamide, 4-{2-[3-(5-Hydroxy-adamantan-2-ylcarbamoyl)-phenoxy]-ethyl}-piperidine-1-carboxylic acid isopropylamide, 3-[2-(1-Cyclopropanesulfonyl-piperidin-4-yl)-ethoxy]-N-(5-hydroxy-adamantan-2-yl)-benzamide, 3-(6-Chloro-pyridin-3-ylmethoxy)-N-(5-hydroxy-adamantan-2-yl)-benzamide, N-(5-Hydroxy-adamantan-2-yl)-3-(tetrahydro-pyran-4-yl-methoxy)-benzamide, N-(5-Hydroxy-adamantan-2-yl)-3-[2-(tetrahydro-pyran-4-yl)-ethoxy]-benzamide, N-(5-Hydroxy-adamantan-2-yl)-3-[2-(2-oxo-pyrrolidin-1-yl)-ethoxy]-benzamide, N-(5-Hydroxy-adamantan-2-yl)-N-methyl-3-(tetrahydro-pyran-4-yloxy)-benzamide', (3-Hydroxy-8-aza-bicyclo[3.2.1]oct-8-yl)-[3-(tetrahydro-pyran-4-ylmethoxy)-phenyl]-methanone, (3-Hydroxy-8-aza-bicyclo[3.2.1]oct-8-yl)-{3-[2-(tetrahydro-pyran-4-yl)-ethoxy]-phenyl}-methanone, (3-Hydroxy-8-aza-bicyclo[3.2.1]oct-8-yl)-[3-(4-hydroxy-cyclohexylmethoxy)-phenyl]-methanone.

197. A compound according to any one of clauses 1-196, which is an agent useful for the treatment, prevention and/or prophylaxis of any conditions, disorders and diseases wherein a modulation or an inhibition of the activity of 11βHSD1 is beneficial.

198. A compound according to any one of the clauses 1-196, which is an agent useful for the treatment, prevention and/or prophylaxis of any conditions, disorders and diseases that are influenced by intracellular glucocorticoid levels.

199. A compound according to any one of the clauses 1-196, which is an agent useful for the treatment, prevention and/or prophylaxis of conditions, disorders or diseases selected from the group consisting of the metabolic syndrome, insulin resistance, dyslipidemia, hypertension and obesity.

200. A compound according to any one of the clauses 1-196, which is an agent useful for the treatment, prevention and/or prophylaxis of type 2 diabetes, impaired glucose tolerance (IGT), impaired fasting glucose (IFG).

201. A compound according to any one of the clauses 1-196, which is an agent useful for the delaying or prevention of the progression from IGT into type 2 diabetes.

202. A compound according to any one of the clauses 1-196, which is an agent useful for delaying or prevention of the progression of the metabolic syndrome into type 2 diabetes.

203. A compound according to any one of the clauses 1-196, which is an agent useful for the treatment, prevention and/or prophylaxis of adverse effects of glucocorticoid receptor agonist treatment or therapy.

204. A pharmaceutical composition comprising, as an active ingredient, at least one compound according to any one of the clauses 1-196 together with one or more pharmaceutically acceptable carriers or excipients.

205. The pharmaceutical composition according to clause 204 which is for oral, nasal, buccal, transdermal, pulmonal or parenteral administration.

206. The pharmaceutical composition according to clause 204 or 205 in unit dosage form, comprising from 0.05 mg to 2000 mg/day, from 0.1 mg to 1000 mg or from 0.5 mg to 500 mg per day of the compound according to anyone of the clauses 1-196.

207. A use of a compound according to any of the clauses 1-196, for the preparation of a pharmaceutical composition for the treatment, prevention and/or prophylaxis of any conditions, disorders and diseases wherein a modulation or an inhibition of the activity of 11βHSD1 is beneficial.

208. A use of a compound according to any of the clauses 1-196, for the preparation of a pharmaceutical composition for the treatment, prevention and/or prophylaxis of any conditions, disorders and diseases that are influenced by intracellular glucocorticoid levels.

209. A use of a compound according to any of the clauses 1-196, for the preparation of a pharmaceutical composition for the treatment, prevention and/or prophylaxis of conditions, disorders or diseases selected from the group consisting of the metabolic syndrome, insulin resistance, dyslipidemia, hypertension and obesity.

210. A use of a compound according to any of the clauses 1-196, for the preparation of a pharmaceutical composition for the treatment, prevention and/or prophylaxis of type 2 diabetes, impaired glucose tolerance (IGT), impaired fasting glucose (IFG).

211. A use of a compound according to any of the clauses 1-196, for the preparation of a pharmaceutical composition for the delaying or prevention of the progression from IGT to type 2 diabetes.

212. A use of a compound according to any of the clauses 1-196, for the preparation of a pharmaceutical composition for the delaying or prevention of the progression of the metabolic syndrome into type 2 diabetes.

213. A use of a compound according to any of the clauses 1-196, for the preparation of a pharmaceutical composition for the treatment, prevention and/or prophylaxis of adverse effects of glucocorticoid receptor agonist treatment or therapy.

214. A method for the treatment, prevention and/or prophylaxis of any conditions, disorders or diseases wherein a modulation or an inhibition of the activity of 11βHSD1 is beneficial, the method comprising administering to a subject in need thereof an effective amount of a compound according to any one of clauses 1-196.

215. The method according to clause 214 wherein the conditions, disorders or diseases are selected from the group consisting of the metabolic syndrome, insulin resistance, dyslipidemia, hypertension and obesity.

The invention claimed is:
1. A compound of Formula (I) or a pharmaceutically acceptable salt thereof:

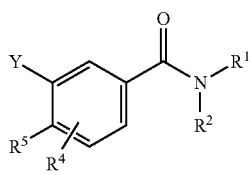

wherein:
$R^1$ is hydrogen;
$R^2$ is 5-hydroxy-adamantan-2-yl;
$R^4$ is hydrogen;
$R^5$ is hydrogen; and
Y is selected from the group consisting of 2-[1-(carboxylic acid isopropylamide)-piperidin-4-yl]-ethoxy, 6-chloropyridin-3-ylmethoxy, tetrahydropyran-4-yl-methoxy, 2-(2-oxo-pyrrolidin-1-yl)-ethoxy, 5-chloro-pyridin-2-yloxy, 6-bromo-pyridin-3-yloxy, phenethyloxy, 2-(tetrahydropyran-4-yl)-ethoxy, benzyloxy, 2-(1-cyclopropane-sulfonyl-piperidin-4-yl)-ethoxy, and 4-fluorobenzyloxy.

2. 4-{2-[3-(5-Hydroxy-adamantan-2-ylcarbamoyl)-phenoxy]-ethyl}-piperidine-1-carboxylic acid isopropylamide, or a pharmaceutically acceptable salt thereof.

3. The compound of claim 2, where the compound is 4-{2-[3-(5-hydroxy-adamantan-2-ylcarbamoyl)-phenoxy]-ethyl}-piperidine-1-carboxylic acid isopropylamide.

4. 3-(6-Chloro-pyridin-3-ylmethoxy)-N-(5-hydroxy-adamantan-2-yl)-benzamide, or a pharmaceutically acceptable salt thereof.

5. The compound of claim 4, where the compound is 3-(6-chloro-pyridin-3-ylmethoxy)-N-(5-hydroxy-adamantan-2-yl)-benzamide.

6. N-(5-Hydroxy-adamantan-2-yl)-3-(tetrahydro-pyran-4-ylmethoxy)-benzamide, or a pharmaceutically acceptable salt thereof.

7. The compound of claim 6, where the compound is N-(5-hydroxy-adamantan-2-yl)-3-(tetrahydro-pyran-4-yl-methoxy)-benzamide.

8. N-(5-Hydroxy-adamantan-2-yl)-3-[2(2-oxo-pyrrolidin-1-yl)-ethoxy]-benzamide, or a pharmaceutically acceptable salt thereof.

9. The compound of claim 8, where the compound is N-(5-hydroxy-adamantan-2-yl)-3-[2-(2-oxo-pyrrolidin-1-yl)-ethoxy]-benzamide.

10. 3-(5-Chloro-pyridin-2-yloxy)-N-(5-hydroxy-adamantan-2-yl)-benzamide, or a pharmaceutically acceptable salt thereof.

11. The compound of claim 10, where the compound is 3-(5-chloro-pyridin-2-yloxy)-N-(5-hydroxy-adamantan-2-yl)-benzamide.

12. 3-(6-Bromo-pyridin-3-yloxy)-N-(5-hydroxy-adamantan-2-yl)-benzamide, or a pharmaceutically acceptable salt thereof.

13. The compound of claim 12, where the compound is 3-(6-bromo-pyridin-3-yloxy)-N-(5-hydroxy-adamantan-2-yl)-benzamide.

14. N-(5-Hydroxy-adamantan-2-yl)-3-phenethyloxy-benzamide, or a pharmaceutically acceptable salt thereof.

15. The compound of claim 14, where the compound is N-(5-hydroxy-adamantan-2-yl)-3-phenethyloxy-benzamide.

16. N-(5-Hydroxy-adamantan-2-yl)-3-[2-(tetrahydro-pyran-4-yl)-ethoxy]-benzamide, or a pharmaceutically acceptable salt thereof.

17. The compound of claim 16, where the compound is N-(5-hydroxy-adamantan-2-yl)-3-[2-(tetrahydro-pyran-4-yl)-ethoxy]-benzamide.

18. 3-Benzyloxy-N-(5-hydroxy-adamantan-2-yl)-benzamide, or a pharmaceutically acceptable salt thereof.

19. The compound of claim 18, where the compound is 3-benzyloxy-N-(5- hydroxy-adamantan-2-yl)-benzamide.

20. 3-[2-(1-Cyclopropane-sulfonyl-piperidin-4-yl)-ethoxy]-N-(5-hydroxy-adamantan-2-yl)-benzamide, or a pharmaceutically acceptable salt thereof.

21. The compound of claim 20, where the compound is 3-[2(1-cyclopropane-sulfonyl-piperidin-4-yl)-ethoxy]-N-(5-hydroxy-adamantan-2-yl)-benzamide.

22. 3-(4-Fluoro-benzyloxy)-N-(5-hydroxy-adamantan-2-yl)-benzamide, or a pharmaceutically acceptable salt thereof.

23. The compound of claim 22, where the compound is 3-(4-fluoro-benzyloxy)-N-(5-hydroxy-adamantan-2-yl)-benzamide.

24. A pharmaceutical composition comprising a compound of claim 1 and a pharmaceutically acceptable carrier or excipient.

25. A pharmaceutical composition comprising a compound of claim 2 and a pharmaceutically acceptable carrier or excipient.

26. A pharmaceutical composition comprising a compound of claim 3 and a pharmaceutically acceptable carrier or excipient.

27. A pharmaceutical composition comprising a compound of claim 4 and a pharmaceutically acceptable carrier or excipient.

28. A pharmaceutical composition comprising a compound of claim 5 and a pharmaceutically acceptable carrier or excipient.

29. A pharmaceutical composition comprising a compound of claim 6 and a pharmaceutically acceptable carrier or excipient.

30. A pharmaceutical composition comprising a compound of claim 7 and a pharmaceutically acceptable carrier or excipient.

31. A pharmaceutical composition comprising a compound of claim 8 and a pharmaceutically acceptable carrier or excipient.

32. A pharmaceutical composition comprising a compound of claim 9 and a pharmaceutically acceptable carrier or excipient.

33. A pharmaceutical composition comprising a compound of claim 10 and a pharmaceutically acceptable carrier or excipient.

34. A pharmaceutical composition comprising a compound of claim 11 and a pharmaceutically acceptable carrier or excipient.

35. A pharmaceutical composition comprising a compound of claim 12 and a pharmaceutically acceptable carrier or excipient.

36. A pharmaceutical composition comprising a compound of claim 13 and a pharmaceutically acceptable carrier or excipient.

37. A pharmaceutical composition comprising a compound of claim 14 and a pharmaceutically acceptable carrier or excipient.

38. A pharmaceutical composition comprising a compound of claim 15 and a pharmaceutically acceptable carrier or excipient.

39. A pharmaceutical composition comprising a compound of claim 16 and a pharmaceutically acceptable carrier or excipient.

40. A pharmaceutical composition comprising a compound of claim 17 and a pharmaceutically acceptable carrier or excipient.

41. A pharmaceutical composition comprising a compound of claim 18 and a pharmaceutically acceptable carrier or excipient.

42. A pharmaceutical composition comprising a compound of claim 19 and a pharmaceutically acceptable carrier or excipient.

43. A pharmaceutical composition comprising a compound of claim 20 and a pharmaceutically acceptable carrier or excipient.

44. A pharmaceutical composition comprising a compound of claim 21 and a pharmaceutically acceptable carrier or excipient.

45. A pharmaceutical composition comprising a compound of claim 22 and a pharmaceutically acceptable carrier or excipient.

46. A pharmaceutical composition comprising a compound of claim 23 and a pharmaceutically acceptable carrier or excipient.

* * * * *

UNITED STATES PATENT AND TRADEMARK OFFICE
CERTIFICATE OF CORRECTION

PATENT NO. : 8,383,820 B2  
APPLICATION NO. : 12/528229  
DATED : February 26, 2013  
INVENTOR(S) : Soren Ebdrup Page 1 of 1

It is certified that error appears in the above-identified patent and that said Letters Patent is hereby corrected as shown below:

In the Claims:

In column 87, line 50, in claim 8, delete "3-[2(2-oxo-pyrrolidin-" and insert
-- 3-[2-(2-oxo-pyrrolidin- --, therefor.

In column 88, line 21, in claim 21, delete "3-[2(1-cyclopropane-sulfonyl-" and insert
-- 3-[2-(1-cyclopropane-sulfonyl- --, therefor.

Signed and Sealed this  
Seventeenth Day of December, 2013

Margaret A. Focarino  
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,383,820 B2 | Page 1 of 1 |
| APPLICATION NO. | : 12/528229 | |
| DATED | : February 26, 2013 | |
| INVENTOR(S) | : Ebdrup | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this
Sixteenth Day of December, 2014

Michelle K. Lee
*Deputy Director of the United States Patent and Trademark Office*